(12) United States Patent
Evans et al.

(10) Patent No.: US 8,158,388 B2
(45) Date of Patent: Apr. 17, 2012

(54) REPAIR OF NUCLEIC ACIDS FOR IMPROVED AMPLIFICATION

(75) Inventors: Thomas C. Evans, Topsfield, MA (US); Lixin Chen, Beverly, MA (US); Chudi Guan, Wenham, MA (US); Rebecca Kucera, Hamilton, MA (US); Barton Slatko, Ipswich, MA (US); Romualdas Vaisvila, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 11/401,826

(22) Filed: Apr. 11, 2006

(65) Prior Publication Data

US 2006/0177867 A1 Aug. 10, 2006

Related U.S. Application Data

(63) Continuation-in-part of application No. 11/255,290, filed on Oct. 20, 2005.

(60) Provisional application No. 60/620,896, filed on Oct. 21, 2004, provisional application No. 60/646,728, filed on Jan. 24, 2005, provisional application No. 60/673,925, filed on Apr. 21, 2005.

(51) Int. Cl.
*C12P 19/34* (2006.01)
(52) U.S. Cl. ..................................... 435/91.2
(58) Field of Classification Search .................. 435/91.2
See application file for complete search history.

(56) References Cited

U.S. PATENT DOCUMENTS

| | | | |
|---|---|---|---|
| 5,035,996 A | 7/1991 | Hartley | |
| 5,455,166 A | 10/1995 | Walker | |
| 5,459,039 A | 10/1995 | Modrich et al. | |
| 5,470,723 A | 11/1995 | Walker et al. | |
| 6,046,036 A * | 4/2000 | Kelley et al. | 435/69.7 |
| 6,060,288 A * | 5/2000 | Adams et al. | 435/91.2 |
| 6,872,552 B2 * | 3/2005 | Ensley | 435/91.2 |
| 2003/0077581 A1 | 4/2003 | Ensley | |
| 2003/0119150 A1 | 6/2003 | Ankenbauer et al. | |
| 2004/0058378 A1 | 3/2004 | Kong et al. | |
| 2004/0067559 A1 | 4/2004 | McCarthy et al. | |
| 2005/0069991 A1 * | 3/2005 | Hyman | 435/91.2 |
| 2006/0014154 A1 * | 1/2006 | Eshoo | 435/6 |
| 2006/0115838 A1 * | 6/2006 | Bazar et al. | 435/6 |

FOREIGN PATENT DOCUMENTS

| | | |
|---|---|---|
| WO | WO 0151656 | 7/2001 |
| WO | WO 2005017173 | 2/2005 |
| WO | WO 2006019784 | 2/2006 |
| WO | WO 2006047461 | 5/2006 |

OTHER PUBLICATIONS

Nicholl et al., "Reconstitution of Human Base Excision Repair with Purified Proteins," Biochemistry, 1997, vol. 36, pp. 7557-7566.*
Dianov, et al., "Reconstitution of the DNA base excision-repair pathway," Current Biology, 1994, vol. 4, No. 12, pp. 1069-1076.*
Karam et al., Genetics, vol. 91, pp. 177-189, 1979.*
Barnes, et al., *Gene* 112:29-35 (1992).
Barnes, W. M., *Proc. Natl. Acad. Sci. USA* 91:2216-2220 (1994).
Bowater, R. P., et. al., *Biochemistry* 33:9266-9275 (1994).
Bucklin, A. & Allen, L. D., *Mol. Phylogenet. Evol.* 30(3):879-882 (2004).
Costa et al., *Biochimie* 85(11):1083-1099 (2003).
Di Bernardo et al., *Nucl. Acids Res.* 30(4):e16 (2002).
Eisen, J.A. and Hanawalt, P.C., *Mutat. Res.* 435(3):171-213 (1999).
Fire and Xu, *Proc. Natl. Acad Sci. USA* 92:4641-4645 (1995).
Fromenty, B., et al., *Nucl. Acids Res.* 28(11):e50 (2000).
Ghadessy et al., *Nature Biotechnol.* 22(6):755-9 (2004).
Gilbert, et al., *Am. J. Hum. Gen.* 72:48-61 (2003).
Guan, C., et.al., *Biochemistry* 43:4313-4322 (2004).
Guatelli et al., *Proc. Natl. Acad. Sci. USA* 87:1874-1878 (1990).
Hofreiter et al., *Nucl. Acids. Res.* 29:4793-9 (2001).
Ide, H., et al., *Biochemistry* 32(32):8276-83 (1993).
Kayser,K, *Origins Sigma-Aldrich* 14:4-5 (2004).
Kermekchiev, M. B. et al., *Nucl. Acids Res.* 31:6139-47 (2003).
Lizardi, et al.,, *Nature Genetics* 19:225-232 (1998).
Liu, et al.,, *J. Am. Chem. Soc.* 118:1587-1594 (1996).
Liu, Y., et al.,, *Annu. Rev. Biochem.* 73:589-615 (2004).
Lowell, J. L. & Klein, D. A., *Biotechniques* 28:676-681 (2000).
Minko et al., *Biochemistry* 44:3000-3009 (2005).
Moolenar et al., *Proc. Nati Acad. Sci USA* 99:1467-72 (2002).
Parkinson, M. J. & Lilley, D. M., *J. Mol. Biol.* 270:169-178 (1997).
Pusch, et al.,, *Nucl. Acids Res.* 26:857 (1998). Eds. Sambrook and Russell, Molecular Cloning: A Laboratory Manual, $3^{rd}$ ed., Cold Spring Harbor Press, Cold Spring Harbor, NY, 2001, Chs. 1,5,8,11,12,15 pp. 6.25, A8.12-A8.24.

(Continued)

*Primary Examiner* — Gary Benzion
*Assistant Examiner* — Cynthia Wilder
(74) *Attorney, Agent, or Firm* — New England Biolabs, Inc; Harriet M. Strimpel

(57) ABSTRACT

Methods and compositions are provided for repairing a polynucleotide so that it can be copied with improved fidelity and/or yield in, for example, an amplification reaction. This involves the use of a reaction mixture that includes a ligase and a cofactor selected from $NAD^+$ or ATP and incubating the polynucleotide with the reaction mixture in the absence of Endonuclease VI.

The reaction mixture may further contain an AP endonuclease and a polymerase. If used, these enzymes may be selected according to their ability to withstand high temperatures. For example, the reaction mixture may be used prior to a polynucleotide synthesis reaction in which case enzymes that are not thermophilic may be used. The repair reaction is not time sensitive with respect to seconds, minutes or hours of incubation in the enzyme mixture in as much as the repair is effected rapidly and prolonged incubation is not generally adverse.

15 Claims, 35 Drawing Sheets

OTHER PUBLICATIONS

Sancar, *Ann. Rev. Biochem* 65:43-81 (1996).
Sattler, et al., *Arch. Biochem Biophys.* 376(1):26-3 (2000).
Smith, J. & Modrich, P., *Proc. Natl. Acad. Sci. USA* 94:6847-6850 (1997).
Thompson, J. R., et al., *Nucl. Acids Res.* 30(9):2083-2088 (2002).
Vande Berg, et al., *J. Biol. Chem.* 273(32):20276-20284 (1998).
Wellinger, et al., *Nucleic Acids Res:* 24(8):1578-79 (1996).
Wood, R.D., et al., *Mutat. Res.* 577(1-2):275-83 (2005).
Xu, Y., et al., *J. Biol. Chem.* 275(27):20949-20955 (2000).
Zou, Y., et al., *Biochemistry* 43:4196-4205 (2004).
Kow, Y et al., *Free Radical Biology and Medicine* 33(7): 886-893 (2002).

\* cited by examiner

Figure 6A-1

```
gi|89109225|ref|AP_003005.1|    DNA ligase, NAD(+)-dependent [Es...    1291    0.0
gi|146615|gb|AAA24071.1|    lig peptide                                1289    0.0
gi|74312947|ref|YP_311366.1|    DNA ligase [Shigella sonnei Ss04...    1289    0.0
gi|75255082|ref|ZP_00726982.1|    COG0272: NAD-dependent DNA lig...    1289    0.0
gi|75196424|ref|ZP_00706494.1|    COG0272: NAD-dependent DNA lig...    1287    0.0
gi|26248787|ref|NP_754827.1|    DNA ligase [Escherichia coli CFT...    1285    0.0
gi|15832537|ref|NP_311310.1|    DNA ligase [Escherichia coli O15...    1285    0.0
gi|75235881|ref|ZP_00720026.1|    COG0272: NAD-dependent DNA lig...    1283    0.0
gi|24052834|gb|AAN43973.1|    DNA ligase [Shigella flexneri 2a s...    1282    0.0
gi|82544871|ref|YP_408818.1|    DNA ligase [Shigella boydii Sb22...    1282    0.0
gi|82777805|ref|YP_404154.1|    DNA ligase [Shigella dysenteriae...    1281    0.0
gi|12516784|gb|AAG57530.1|    DNA ligase [Escherichia coli O157:...    1274    0.0
gi|56126943|gb|AAV76449.1|    DNA ligase [Salmonella enterica su...    1217    0.0
gi|29140957|ref|NP_804299.1|    DNA ligase [Salmonella enterica ...    1215    0.0
gi|16420966|gb|AAL21321.1|    DNA ligase [Salmonella typhimurium...    1214    0.0
gi|16503646|emb|CAD07659.1|    DNA ligase [Salmonella enterica s...    1214    0.0
gi|62180995|ref|YP_217412.1|    DNA ligase [Salmonella enterica ...    1212    0.0
gi|83568882|ref|ZP_00920360.1|    COG0272: NAD-dependent DNA lig...    1110    0.0
gi|77979158|ref|ZP_00834579.1|    COG0272: NAD-dependent DNA lig...    1049    0.0
gi|77974567|ref|ZP_00830106.1|    COG0272: NAD-dependent DNA lig...    1044    0.0
gi|51590312|emb|CAH21949.1|    DNA ligase [Yersinia pseudotuberc...    1041    0.0
gi|45437255|gb|AAS62807.1|    DNA ligase [Yersinia pestis biovar...    1040    0.0
gi|77629760|ref|ZP_00792346.1|    COG0272: NAD-dependent DNA lig...    1040    0.0
gi|36784781|emb|CAE13691.1|    DNA ligase (polydeoxyribonucleoti...    1040    0.0
gi|77960935|ref|ZP_00824787.1|    COG0272: NAD-dependent DNA lig...    1031    0.0
gi|49613030|emb|CAG76481.1|    DNA ligase [Erwinia carotovora su...    1022    0.0
gi|77956838|ref|ZP_00820914.1|    COG0272: NAD-dependent DNA lig...    1000    0.0
gi|85059656|ref|YP_455358.1|    DNA ligase [Sodalis glossinidius...     923    0.0
gi|28805786|dbj|BAC59063.1|    DNA ligase [Vibrio parahaemolytic...     861    0.0
gi|75818305|ref|ZP_00748487.1|    COG0272: NAD-dependent DNA lig...     861    0.0
gi|9655431|gb|AAF94133.1|    DNA ligase [Vibrio cholerae O1 biov...     858    0.0
gi|59712497|ref|YP_205273.1|    DNA ligase [Vibrio fischeri ES11...     855    0.0
gi|75826282|ref|ZP_00755717.1|    COG0272: NAD-dependent DNA lig...     853    0.0
gi|75814172|ref|ZP_00744801.1|    COG0272: NAD-dependent DNA lig...     853    0.0
gi|27359804|gb|AAO08743.1|    NAD-dependent DNA ligase [Vibrio v...     845    0.0
gi|90579891|ref|ZP_01235699.1|    DNA ligase [Vibrio angustum S1...     844    0.0
gi|37679166|ref|NP_933775.1|    DNA ligase [Vibrio vulnificus YJ...     843    0.0
gi|89075460|ref|ZP_01161871.1|    DNA ligase [Photobacterium sp....     843    0.0
gi|84393803|ref|ZP_00992550.1|    DNA ligase [Vibrio splendidus ...     838    0.0
gi|86148411|ref|ZP_01066703.1|    DNA ligase [Vibrio sp. MED222]...     838    0.0
gi|75429820|ref|ZP_00732457.1|    DNA ligase (NAD+) [Actinobacil...     837    0.0
gi|1169385|sp|P43813|DNLJ_HAEIN    DNA ligase (Polydeoxyribonucl...     833    0.0
gi|46133287|ref|ZP_00156942.2|    COG0272: NAD-dependent DNA lig...     833    0.0
gi|52307873|gb|AAU38373.1|    Lig protein [Mannheimia succinicip...     831    0.0
gi|68057854|gb|AAX88107.1|    DNA ligase [Haemophilus influenzae...     828    0.0
gi|42630088|ref|ZP_00155632.1|    COG0272: NAD-dependent DNA lig...     828    0.0
gi|53728415|ref|ZP_00132847.2|    COG0272: NAD-dependent DNA lig...     828    0.0
gi|23466524|ref|ZP_00122112.1|    COG0272: NAD-dependent DNA lig...     828    0.0
gi|88861394|ref|ZP_01136024.1|    NAD-dependent DNA ligase [Pseu...     823    0.0
gi|90410985|ref|ZP_01218999.1|    DNA ligase [Photobacterium pro...     823    0.0
gi|12722128|gb|AAK03800.1|    Lig [Pasteurella multocida subsp. ...     820    0.0
gi|46143448|ref|ZP_00135242.2|    COG0272: NAD-dependent DNA lig...     818    0.0
gi|46912488|emb|CAG19280.1|    putative NAD-dependent DNA ligase...     818    0.0
gi|76874937|emb|CAI86158.1|    NAD-dependent DNA ligase [Pseudoa...     815    0.0
gi|5733399|gb|AAD49562.1|    NAD-dependent DNA ligase [Pseudoaltero     810    0.0
gi|24374425|ref|NP_718468.1|    DNA ligase, NAD-dependent [Shewa...     796    0.0
gi|78691747|ref|ZP_00856345.1|    NAD-dependent DNA ligase [Shew...     796    0.0
gi|78685944|ref|ZP_00850717.1|    NAD-dependent DNA ligase [Shew...     795    0.0
gi|82498323|ref|ZP_00883827.1|    NAD-dependent DNA ligase [Shew...     793    0.0
```

Figure 6A-2

```
gi|90021526|ref|YP_527353.1|   DNA ligase (NAD+) [Saccharophagu...    790   0.0
gi|82743297|ref|ZP_00905952.1|   NAD-dependent DNA ligase [Shew...    789   0.0
gi|77815048|ref|ZP_00814293.1|   NAD-dependent DNA ligase [Shew...    787   0.0
gi|89094416|ref|ZP_01167356.1|   DNA ligase [Oceanospirillum sp...    781   0.0
gi|56179811|gb|AAV82533.1|   NAD-dependent DNA ligase [Idiomari...    779   0.0
gi|69952864|ref|ZP_00640212.1|   NAD-dependent DNA ligase [Shew...    776   0.0
gi|83647417|ref|YP_435852.1|   DNA ligase, NAD-dependent [Hahel...    772   0.0
gi|75233892|ref|ZP_00718355.1|   COG0272: NAD-dependent DNA lig...    765   0.0
gi|69157116|gb|EAN69375.1|   NAD-dependent DNA ligase [Shewanel...    764   0.0
gi|33151983|ref|NP_873336.1|   DNA ligase [Haemophilus ducreyi ...    762   0.0
gi|67676935|ref|ZP_00473679.1|   NAD-dependent DNA ligase [Chro...    756   0.0
gi|88800009|ref|ZP_01115580.1|   DNA ligase, NAD-dependent [Rei...    749   0.0
gi|73541575|ref|YP_296095.1|   NAD-dependent DNA ligase [Ralsto...    748   0.0
gi|68559661|ref|ZP_00598993.1|   NAD-dependent DNA ligase [Rals...    743   0.0
gi|77954826|ref|ZP_00819212.1|   NAD-dependent DNA ligase [Mari...    738   0.0
gi|90416525|ref|ZP_01224456.1|   DNA ligase, NAD-dependent [mar...    737   0.0
gi|84362198|ref|ZP_00986832.1|   COG0272: NAD-dependent DNA lig...    734   0.0
gi|52210187|emb|CAH36166.1|   DNA ligase [Burkholderia pseudoma...    734   0.0
gi|48787700|ref|ZP_00283679.1|   COG0272: NAD-dependent DNA lig...    733   0.0
gi|52427167|gb|AAU47760.1|   DNA ligase, NAD-dependent [Burkhol...    732   0.0
gi|67666067|ref|ZP_00463321.1|   NAD-dependent DNA ligase [Burk...    732   0.0
gi|84355004|ref|ZP_00979896.1|   COG0272: NAD-dependent DNA lig...    732   0.0
gi|83616883|ref|ZP_00927451.1|   COG0272: NAD-dependent DNA lig...    732   0.0
gi|71146748|gb|AAZ27221.1|   DNA ligase, NAD-dependent [Colwell...    732   0.0
gi|76580236|gb|ABA49711.1|   DNA ligase, NAD-dependent [Burkhol...    731   0.0
gi|82533924|ref|ZP_00892975.1|   hypothetical protein Bpsel10_0...    731   0.0
gi|67734853|ref|ZP_00485927.1|   COG0272: NAD-dependent DNA lig...    731   0.0
gi|67549103|ref|ZP_00426977.1|   NAD-dependent DNA ligase [Burk...    727   0.0
gi|74017855|ref|ZP_00688478.1|   NAD-dependent DNA ligase [Burk...    726   0.0
gi|77967548|gb|ABB08928.1|   DNA ligase (NAD+) [Burkholderia sp...    726   0.0
gi|83720010|ref|YP_442546.1|   DNA ligase, NAD-dependent [Burkh...    724   0.0
gi|29541145|gb|AAO90088.1|   DNA ligase, NAD-dependent [Coxiell...    710   0.0
gi|88703478|ref|ZP_01101194.1|   DNA ligase [gamma proteobacter...    706   0.0
gi|87119444|ref|ZP_01075341.1|   NAD-dependent DNA ligase [Mari...    704   0.0
gi|90408119|ref|ZP_01216289.1|   DNA ligase [Psychromonas sp. C...    704   0.0
gi|53803401|ref|YP_114852.1|   DNA ligase, NAD-dependent [Methy...    699   0.0
gi|76883484|gb|ABA58165.1|   DNA ligase (NAD+) [Nitrosococcus o...    697   0.0
gi|33574305|emb|CAE38638.1|   DNA ligase [Bordetella parapertus...    694   0.0
gi|33577221|emb|CAE35778.1|   DNA ligase [Bordetella bronchisep...    694   0.0
gi|78363869|gb|ABB41834.1|   DNA ligase, NAD-dependent [Thiomic...    694   0.0
gi|33564504|emb|CAE43819.1|   DNA ligase [Bordetella pertussis ...    692   0.0
gi|52628304|gb|AAU27045.1|   DNA ligase [Legionella pneumophila...    687   0.0
gi|71907364|ref|YP_284951.1|   NAD-dependent DNA ligase [Dechlo...    687   0.0
gi|74316642|ref|YP_314382.1|   NAD-dependent DNA ligase [Thioba...    687   0.0
gi|53750764|emb|CAH12171.1|   DNA ligase [Legionella pneumophil...    684   0.0
gi|53753763|emb|CAH15221.1|   DNA ligase [Legionella pneumophil...    684   0.0
gi|78701901|ref|ZP_00866347.1|   NAD-dependent DNA ligase [Alka...    680   0.0
gi|56315126|emb|CAI09771.1|   NAD-dependent DNA ligase [Azoarcu...    679   0.0
gi|30249713|ref|NP_841783.1|   NAD-dependent DNA ligase [Nitros...    678   0.0
gi|82701780|ref|YP_411346.1|   DNA ligase, NAD-dependent [Nitro...    674   0.0
gi|67908878|ref|ZP_00507276.1|   NAD-dependent DNA ligase [Pola...    673   0.0
gi|71550594|ref|ZP_00670695.1|   NAD-dependent DNA ligase [Nitr...    671   0.0
gi|68213713|ref|ZP_00565543.1|   NAD-dependent DNA ligase [Meth...    668   0.0
gi|89900985|ref|YP_523456.1|   DNA ligase, NAD-dependent [Rhodo...    666   0.0
gi|84713236|ref|ZP_01021022.1|   NAD-dependent DNA ligase [Pola...    663   0.0
gi|82739903|ref|ZP_00902683.1|   NAD-dependent DNA ligase [Pseu...    653   0.0
gi|88810628|ref|ZP_01125885.1|   DNA ligase, NAD-dependent [Nit...    652   0.0
gi|75177822|ref|ZP_00697884.1|   COG0272: NAD-dependent DNA lig...    652   0.0
gi|26990965|ref|NP_746390.1|   DNA ligase [Pseudomonas putida K...    649   0.0
gi|70729275|ref|YP_259012.1|   DNA ligase [Pseudomonas fluoresc...    641   0.0
```

Figure 6A-3

```
gi|77382031|gb|ABA73544.1|    NAD-dependent DNA ligase [Pseudomo...    640    0.0
gi|71558494|gb|AAZ37705.1|    DNA ligase, NAD-dependent [Pseudom...    640    0.0
gi|66045063|ref|YP_234904.1|    DNA ligase [Pseudomonas syringae...    637    0.0
gi|28870811|ref|NP_793430.1|    DNA ligase [Pseudomonas syringae...    636    0.0
gi|49530036|emb|CAG67748.1|    DNA ligase [Acinetobacter sp. ADP...    635    1e-180
gi|67154662|ref|ZP_00416407.1|    NAD-dependent DNA ligase [Azot...    635    1e-180
gi|32041572|ref|ZP_00139155.1|    COG0272: NAD-dependent DNA lig...    632    2e-179
gi|75177823|ref|ZP_00697885.1|    COG0272: NAD-dependent DNA lig...    632    2e-179
gi|9947487|gb|AAG04918.1|    DNA ligase [Pseudomonas aeruginosa ...    631    3e-179
gi|84321716|ref|ZP_00970070.1|    COG0272: NAD-dependent DNA lig...    630    6e-179
gi|47575578|ref|ZP_00245613.1|    COG0272: NAD-dependent DNA lig...    629    1e-178
gi|84328443|ref|ZP_00976450.1|    COG0272: NAD-dependent DNA lig...    629    2e-178
gi|89097084|ref|ZP_01169975.1|    DNA ligase [Bacillus sp. NRRL ...    628    3e-178
gi|88948654|ref|ZP_01151417.1|    NAD-dependent DNA ligase [Halo...    627    4e-178
gi|71362759|ref|ZP_00653910.1|    NAD-dependent DNA ligase [Psyc...    621    3e-176
gi|88936719|ref|ZP_01142320.1|    NAD-dependent DNA ligase [Geob...    609    1e-172
gi|2632976|emb|CAB12482.1|    DNA ligase [Bacillus subtilis subs...    609    1e-172
gi|56378653|dbj|BAD74561.1|    DNA ligase (polydeoxyribonucleoti...    608    2e-172
gi|88796019|ref|ZP_01111705.1|    DNA ligase, NAD-dependent [Alt...    606    9e-172
gi|71037881|gb|AAZ18189.1|    probable NAD dependent DNA ligase ...    606    1e-171
gi|78195179|gb|ABB32946.1|    NAD-dependent DNA ligase C4-type [...    605    2e-171
gi|52002360|gb|AAU22302.1|    DNA ligase [Bacillus licheniformis...    605    3e-171
gi|3688229|emb|CAA09732.1|    DNA ligase [Geobacillus stearother...    600    9e-170
gi|27262356|gb|AAN87459.1|    NAD-dependent DNA ligase [Heliobacill    598    2e-169
gi|52313150|emb|CAH55605.1|    DNA ligase (NAD dependent) [Bacillus   597    4e-169
gi|56909098|dbj|BAD63625.1|    DNA ligase [Bacillus clausii KSM-...    597    7e-169
gi|77919807|ref|YP_357622.1|    DNA ligase, NAD-dependent [Pelob...    594    5e-168
gi|85859410|ref|YP_461612.1|    NAD-dependent DNA ligase [Syntro...    593    8e-168
gi|10173263|dbj|BAB04368.1|    DNA ligase (polydeoxyribonucleoti...    593    1e-167
gi|89200069|ref|ZP_01178825.1|    NAD-dependent DNA ligase [Baci...    591    3e-167
gi|39982761|gb|AAR34220.1|    DNA ligase, NAD-dependent [Geobact...    590    9e-167
gi|39936579|ref|NP_948855.1|    DNA ligase [Rhodopseudomonas pal...    589    1e-166
gi|75700263|gb|ABA19939.1|    NAD-dependent DNA ligase [Anabaena...    588    3e-166
gi|71545854|ref|ZP_00666752.1|    NAD-dependent DNA ligase [Synt...    587    8e-166
gi|22776440|dbj|BAC12716.1|    DNA ligase (polydeoxyribonucleoti...    586    1e-165
gi|21112648|gb|AAM40865.1|    DNA ligase [Xanthomonas campestris...    586    1e-165
gi|83592275|ref|YP_426027.1|    DNA ligase (NAD+) [Rhodospirillu...    586    1e-165
gi|10038755|dbj|BAB12790.1|    DNA ligase (NAD+) [Buchnera aphid...    585    2e-165
gi|82523924|emb|CAI78646.1|    NAD-dependent DNA ligase [uncultured   585    3e-165
gi|77688133|ref|ZP_00803318.1|    NAD-dependent DNA ligase [Rhod...    584    4e-165
gi|49330634|gb|AAT61280.1|    DNA ligase(NAD+) (NAD-dependent DN...    583    6e-165
gi|51978410|gb|AAU19960.1|    DNA ligase(NAD+) (NAD-dependent DN...    583    6e-165
gi|75759916|ref|ZP_00739987.1|    NAD-dependent DNA ligase [Baci...    583    6e-165
gi|29894090|gb|AAP07381.1|    NAD-dependent DNA ligase [Bacillus...    583    8e-165
gi|50082973|gb|AAT70114.1|    DNA ligase, NAD-dependent [Bacillu...    583    1e-164
gi|56708436|ref|YP_170332.1|    DNA ligase [Francisella tularens...    582    2e-164
gi|42779416|ref|NP_976663.1|    DNA ligase [Bacillus cereus ATCC...    582    2e-164
gi|76260005|ref|ZP_00767647.1|    NAD-dependent DNA ligase [Chlo...    582    2e-164
gi|68054840|ref|ZP_00538990.1|    NAD-dependent DNA ligase [Exig...    581    3e-164
gi|69928974|ref|ZP_00625988.1|    NAD-dependent DNA ligase [Nitr...    581    3e-164
gi|78047224|ref|YP_363399.1|    DNA ligase [Xanthomonas campestr...    581    4e-164
gi|89204794|ref|ZP_01183370.1|    DNA ligase, NAD-dependent [Baci...   580    7e-164
gi|89256066|ref|YP_513428.1|    DNA ligase [Francisella tularens...    579    2e-163
gi|86749131|ref|YP_485627.1|    DNA ligase, NAD-dependent [Rhodo...    579    2e-163
gi|85714986|ref|ZP_01045971.1|    NAD-dependent DNA ligase [Nitr...    578    2e-163
gi|83858905|ref|ZP_00952427.1|    NAD-dependent DNA ligase [Ocea...    578    3e-163
gi|21107814|gb|AAM36495.1|    DNA ligase [Xanthomonas axonopodis...    578    4e-163
gi|89358992|ref|ZP_01196814.1|    NAD-dependent DNA ligase [Xant...    578    4e-163
gi|17135537|dbj|BAB78083.1|    DNA ligase [Nostoc sp. PCC 7120] ...    577    5e-163
gi|23126503|ref|ZP_00108396.1|    COG0272: NAD-dependent DNA lig...    576    1e-163
```

Figure 6A-4

```
gi|77741190|ref|ZP_00809674.1|    NAD-dependent DNA ligase [Rhod...    576    1e-162
gi|83953544|ref|ZP_00962265.1|    DNA ligase, NAD-dependent [Sul...    576    1e-162
gi|77995308|gb|ABB14207.1|    DNA ligase, NAD-dependent [Carboxy...    575    2e-162
gi|78696034|ref|ZP_00860544.1|    NAD-dependent DNA ligase [Brad...    575    2e-162
gi|74420125|gb|ABA04324.1|    NAD-dependent DNA ligase [Nitrobac...    573    7e-162
gi|46449435|gb|AAS96086.1|    DNA ligase, NAD-dependent [Desulfo...    572    1e-161
gi|83942325|ref|ZP_00954786.1|    DNA ligase, NAD-dependent [Sul...    572    1e-161
gi|76796059|ref|ZP_00778428.1|    NAD-dependent DNA ligase [Ther...    572    2e-161
gi|27381702|ref|NP_773231.1|    DNA ligase [Bradyrhizobium japon...    571    3e-161
gi|23348266|gb|AAN30333.1|    DNA ligase, NAD-dependent [Brucell...    571    4e-161
gi|68195064|gb|EAN09526.1|    NAD-dependent DNA ligase [Enteroco...    571    4e-161
gi|17982511|gb|AAL51770.1|    NAD-DEPENDENT DNA LIGASE [Brucella...    570    6e-161
gi|47095684|ref|ZP_00233291.1|    DNA ligase, NAD-dependent [Lis...    570    7e-161
gi|16411212|emb|CAC99836.1|    lmo1758 [Listeria monocytogenes] ...    569    1e-160
gi|78219541|gb|ABB38890.1|    DNA ligase, NAD-dependent [Desulfo...    569    2e-160
gi|7379580|emb|CAB84145.1|    putative DNA ligase [Neisseria men...    569    2e-160
gi|16414371|emb|CAC97100.1|    lin1870 [Listeria innocua] >gi|16...    569    2e-160
gi|59800688|ref|YP_207400.1|    putative DNA ligase [Neisseria g...    568    4e-160
gi|47092911|ref|ZP_00230693.1|    DNA ligase, NAD-dependent [Lis...    568    4e-160
gi|88945246|ref|ZP_01148460.1|    NAD-dependent DNA ligase [Desu...    568    4e-160
gi|46907988|ref|YP_014377.1|    DNA ligase [Listeria monocytogen...    566    1e-159
gi|67916669|ref|ZP_00510369.1|    NAD-dependent DNA ligase [Clos...    566    1e-159
gi|7225892|gb|AAF41084.1|    DNA ligase [Neisseria meningitidis ...    566    1e-159
gi|67920947|ref|ZP_00514466.1|    NAD-dependent DNA ligase [Croc...    564    5e-159
gi|85708859|ref|ZP_01039925.1|    DNA ligase [Erythrobacter sp. ...    564    5e-159
gi|29342778|gb|AAO80542.1|    DNA ligase, NAD-dependent [Enteroc...    563    7e-159
gi|90418183|ref|ZP_01226095.1|    DNA ligase [Aurantimonas sp. S...    563    9e-159
gi|71492817|gb|EAO25119.1|    NAD-dependent DNA ligase [Syntroph...    562    2e-158
gi|68193724|gb|EAN08376.1|    NAD-dependent DNA ligase [Mesorhiz...    561    3e-158
gi|89210598|ref|ZP_01188986.1|    NAD-dependent DNA ligase [Halo...    561    3e-158
gi|15075186|emb|CAC46743.1|    PROBABLE DNA LIGASE PROTEIN [Sino...    561    3e-158
gi|73662196|ref|YP_300977.1|    NAD-dependent DNA ligase [Staphy...    561    3e-158
gi|34499358|ref|NP_903573.1|    DNA ligase [Chromobacterium viol...    558    2e-157
gi|51857652|dbj|BAD41810.1|    NAD-dependent DNA ligase [Symbiob...    558    3e-157
gi|68206302|ref|ZP_00558492.1|    NAD-dependent DNA ligase [Desu...    558    3e-157
gi|49284|emb|CAA77966.1|    DNA ligase [Zymomonas mobilis] >gi|1...    557    5e-157
gi|20515592|gb|AAM23875.1|    NAD-dependent DNA ligase (contains...    556    8e-157
gi|89896634|ref|YP_520121.1|    hypothetical protein DSY3888 [De...    556    8e-157
gi|86282540|gb|ABC91603.1|    DNA ligase (NAD+) protein [Rhizobi...    556    8e-157
gi|83312957|ref|YP_423221.1|    NAD-dependent DNA ligase [Magnet...    556    1e-156
gi|86157121|ref|YP_463906.1|    DNA ligase, NAD-dependent [Anaer...    555    2e-156
gi|17428413|emb|CAD15100.1|    PUTATIVE DNA LIGASE (POLYDEOXYRIB...    555    3e-156
gi|87308785|ref|ZP_01090924.1|    DNA ligase [Blastopirellula ma...    555    3e-156
gi|59802648|sp|P28719|DNLJ_ZYMMO  DNA ligase (Polydeoxyribonuc...      554    4e-156
gi|17740541|gb|AAL43073.1|    DNA ligase [Agrobacterium tumefaci...    554    5e-156
gi|39574234|emb|CAE77738.1|    DNA ligase [Bdellovibrio bacterio...    553    7e-156
gi|81299088|ref|YP_399296.1|    DNA ligase, NAD-dependent [Synec...    553    7e-156
gi|1651660|dbj|BAA16588.1|    DNA ligase [Synechocystis sp. PCC ...    553    1e-155
gi|23013561|ref|ZP_00053441.1|    COG0272: NAD-dependent DNA lig...    553    1e-155
gi|27316054|gb|AAO05188.1|    DNA ligase [Staphylococcus epiderm...    551    4e-155
gi|57867376|ref|YP_189011.1|    DNA ligase, NAD-dependent [Staph...    551    4e-155
gi|85374270|ref|YP_458332.1|    DNA ligase [Erythrobacter litora...    550    8e-155
gi|57284841|gb|AAW36935.1|    DNA ligase, NAD-dependent [Staphyl...    550    1e-154
gi|68560458|ref|ZP_00599771.1|    NAD-dependent DNA ligase [Rubr...    550    1e-154
gi|88195803|ref|YP_500613.1|    DNA ligase, NAD-dependent [Staph...    549    1e-154
gi|49484145|ref|YP_041369.1|    DNA ligase [Staphylococcus aureu...    549    1e-154
gi|14247676|dbj|BAB58066.1|    DNA ligase [Staphylococcus aureus...    549    2e-154
gi|83748812|ref|ZP_00945825.1|    NAD-dependent DNA ligase [Rals...    548    3e-154
gi|49238653|emb|CAF27899.1|    DNA ligase [Bartonella henselae s...    548    4e-154
gi|1352292|sp|P49421|DNLJ_RHOMR  DNA ligase (Polydeoxyribonucl...      547    5e-154
```

Figure 6A-5

```
gi|68446772|dbj|BAE04356.1|   DNA ligase [Staphylococcus haemol...    546    9e-154
gi|82751560|ref|YP_417301.1|   DNA ligase [Staphylococcus aureu...    546    9e-154
gi|75854998|ref|ZP_00762664.1|   COG0272: NAD-dependent DNA lig...    546    1e-153
gi|71275191|ref|ZP_00651478.1|   NAD-dependent DNA ligase [Xyle...    544    4e-153
gi|71899829|ref|ZP_00681979.1|   NAD-dependent DNA ligase [Xyle...    544    4e-153
gi|58426627|gb|AAW75664.1|   DNA ligase [Xanthomonas oryzae pv. or    544    6e-153
gi|77760702|ref|YP_201049.2|   DNA ligase [Xanthomonas oryzae pv.    544    6e-153
gi|49239950|emb|CAF26355.1|   DNA ligase [Bartonella quintana s...    543    7e-153
gi|84623945|ref|YP_451317.1|   DNA ligase [Xanthomonas oryzae p...    543    7e-153
gi|83751525|ref|ZP_00947938.1|   COG0272: NAD-dependent DNA lig...    543    7e-153
gi|90573086|ref|ZP_01229606.1|   hypothetical protein CdifQ_020...    542    2e-152
gi|9107768|gb|AAF85353.1|   DNA ligase [Xylella fastidiosa 9a5c]    542    2e-152
gi|77747612|ref|NP_299833.2|   DNA ligase [Xylella fastidiosa 9a5c    542    2e-152
gi|87199755|ref|YP_497012.1|   DNA ligase, NAD-dependent [Novos...    541    4e-152
gi|28199807|ref|NP_780121.1|   DNA ligase [Xylella fastidiosa T...    541    4e-152
gi|84686905|ref|ZP_01014789.1|   DNA ligase, NAD-dependent [Rho...    541    5e-152
gi|35211289|dbj|BAC88668.1|   DNA ligase [Gloeobacter violaceus...    540    1e-151
gi|85713360|ref|ZP_01044373.1|   NAD-dependent DNA ligase [Idio...    540    1e-151
gi|71898271|ref|ZP_00680445.1|   NAD-dependent DNA ligase [Xyle...    539    1e-151
gi|82499709|ref|ZP_00885148.1|   NAD-dependent DNA ligase [Cald...    539    2e-151
gi|88930689|ref|ZP_01136384.1|   DNA ligase (NAD+) [Acidothermu...    538    3e-151
gi|86605509|ref|YP_474272.1|   DNA ligase, NAD-dependent [Synec...    537    7e-151
gi|82523684|emb|CAI78466.1|   NAD-dependent DNA ligase [uncultu...    537    7e-151
gi|58001067|gb|AAW59961.1|   NAD-dependent DNA ligase [Gluconob...    536    1e-150
gi|86680809|ref|YP_477571.1|   DNA ligase, NAD-dependent [Synec...    536    1e-150
gi|83371245|ref|ZP_00916063.1|   NAD-dependent DNA ligase [Rhod...    536    1e-150
gi|7674019|sp|Q9ZHI0|DNLJ_THEFI   DNA ligase (Polydeoxyribonucl...    535    2e-150
gi|83590843|ref|YP_430852.1|   DNA ligase, NAD-dependent [Moore...    535    3e-150
gi|33639520|emb|CAE08904.1|   Putative DNA ligase [Synechococcu...    535    3e-150
gi|68539257|ref|ZP_00579030.1|   NAD-dependent DNA ligase [Sphi...    535    3e-150
gi|609276|emb|CAA82645.1|   DNA ligase [Thermus scotoductus] >g...    535    3e-150
gi|52216559|dbj|BAD49152.1|   DNA ligase [Bacteroides fragilis ...    534    4e-150
gi|60493399|emb|CAH08185.1|   putative DNA ligase [Bacteroides ...    534    6e-150
gi|57225054|gb|AAW40111.1|   DNA ligase, NAD-dependent [Dehaloc...    534    6e-150
gi|47569950|ref|ZP_00240615.1|   DNA ligase, NAD-dependent [Bac...    532    2e-149
gi|46199040|ref|YP_004707.1|   NAD-dependent DNA ligase [Thermu...    531    3e-149
gi|22294579|dbj|BAC08409.1|   DNA ligase [Thermosynechococcus e...    531    4e-149
gi|21646383|gb|AAM71700.1|   DNA ligase, NAD-dependent [Chlorob...    531    4e-149
gi|7674018|sp|Q9ZFY8|DNLJ_THESK   DNA ligase (Polydeoxyribonucl...    531    5e-149
gi|86742328|ref|YP_482728.1|   DNA ligase, NAD-dependent [Frank...    530    6e-149
gi|68247019|gb|EAN29109.1|   NAD-dependent DNA ligase [Magnetoc...    530    1e-148
gi|55772479|dbj|BAD70920.1|   DNA ligase [NAD+] [Thermus thermo...    530    1e-148
gi|78198515|gb|ABB36280.1|   DNA ligase, NAD-dependent [Synecho...    529    1e-148
gi|90821514|gb|ABE00153.1|   NAD-dependent DNA ligase [Lactobac...    529    2e-148
gi|73660152|emb|CAI82759.1|   DNA ligase, NAD-dependent [Dehalo...    529    2e-148
gi|14022280|dbj|BAB48890.1|   DNA ligase [Mesorhizobium loti MA...    528    2e-148
gi|81429164|ref|YP_396165.1|   NAD-dependent DNA ligase [Lactob...    528    2e-148
gi|83816597|ref|YP_445022.1|   DNA ligase, NAD-dependent [Salin...    528    3e-148
gi|88933690|ref|ZP_01139360.1|   NAD-dependent DNA ligase [Deha...    528    4e-148
gi|88809499|ref|ZP_01125007.1|   DNA ligase [Synechococcus sp. ...    526    1e-147
gi|68230474|ref|ZP_00569657.1|   NAD-dependent DNA ligase [Fran...    526    1e-147
gi|78170066|gb|ABB27163.1|   DNA ligase (NAD+) [Synechococcus s...    526    2e-147
gi|12723294|gb|AAK04517.1|   DNA ligase (EC 6.5.1.2) [Lactococc...    525    2e-147
gi|48855095|ref|ZP_00309255.1|   COG0272: NAD-dependent DNA lig...    525    2e-147
gi|89069525|ref|ZP_01156869.1|   DNA ligase, NAD-dependent [Oce...    525    4e-147
gi|83373955|ref|ZP_00918731.1|   NAD-dependent DNA ligase [Rhod...    523    1e-146
gi|77387594|gb|ABA78779.1|   DNA ligase [Rhodobacter sphaeroide...    522    2e-146
gi|28270757|emb|CAD63662.1|   DNA ligase (NAD+) [Lactobacillus ...    522    2e-146
gi|62527031|ref|ZP_00388332.1|   COG0272: NAD-dependent DNA lig...    521    3e-146
gi|29338199|gb|AAO76001.1|   DNA ligase [Bacteroides thetaiotao...    521    5e-146
```

Figure 6A-6

```
gi|71796383|gb|AAZ41134.1|   DNA ligase [Candidatus Blochmannia...    519    2e-145
gi|55739443|gb|AAV63084.1|   DNA ligase [Streptococcus thermoph...    518    3e-145
gi|87123447|ref|ZP_01079298.1|   BRCT domain:NAD-dependent DNA ...    518    3e-145
gi|90587401|ref|ZP_01243054.1|   DNA ligase (NAD+) [Flavobacter...    517    6e-145
gi|48870998|ref|ZP_00323715.1|   COG0272: NAD-dependent DNA lig...    516    1e-144
gi|84516174|ref|ZP_01003534.1|   DNA ligase [Loktanella vestfol...    516    2e-144
gi|76562591|gb|ABA45175.1|   DNA ligase, NAD-dependent [Strepto...    514    4e-144
gi|88941349|ref|ZP_01146768.1|   DNA ligase, NAD-dependent [Aci...    514    5e-144
gi|68548842|ref|ZP_00588311.1|   NAD-dependent DNA ligase [Pelo...    514    5e-144
gi|22537014|ref|NP_687865.1|   DNA ligase [Streptococcus agalac...    514    6e-144
gi|84703858|ref|ZP_01017686.1|   NAD-dependent DNA ligase [Parv...    514    6e-144
gi|77410701|ref|ZP_00787060.1|   DNA ligase, NAD-dependent [Str...    512    2e-143
gi|34540958|ref|NP_905437.1|   DNA ligase, NAD-dependent [Porph...    511    4e-143
gi|23095302|emb|CAD46512.1|   Unknown [Streptococcus agalactiae...    511    4e-143
gi|78167455|gb|ABB24553.1|   DNA ligase (NAD+) [Pelodictyon lut...    511    4e-143
gi|76791606|ref|ZP_00774112.1|   DNA ligase (NAD+) [Pseudoalter...    511    5e-143
gi|78170455|gb|ABB27551.1|   NAD-dependent DNA ligase [Chlorobi...    509    1e-142
gi|72383117|ref|YP_292472.1|   NAD-dependent DNA ligase [Prochl...    509    2e-142
gi|77414096|ref|ZP_00790264.1|   DNA ligase, NAD-dependent [Str...    508    3e-142
gi|89091099|ref|ZP_01164124.1|   NAD-dependent DNA ligase [Lact...    508    3e-142
gi|66797379|ref|ZP_00396139.1|   NAD-dependent DNA ligase [Dein...    506    1e-141
gi|86131748|ref|ZP_01050345.1|   putative DNA ligase [Celluloph...    506    2e-141
gi|89891625|ref|ZP_01203129.1|   DNA  ligase [Flavobacteria bac...    505    2e-141
gi|77409440|ref|ZP_00786135.1|   DNA ligase, NAD-dependent [Str...    505    2e-141
gi|84519006|ref|ZP_01006355.1|   NAD-dependent DNA ligase [Proc...    505    2e-141
gi|34581289|ref|ZP_00142769.1|   DNA ligase [Rickettsia sibiric...    505    3e-141
gi|88805870|ref|ZP_01121389.1|   DNA ligase [Robiginitalea bifo...    504    4e-141
gi|81096636|ref|ZP_00874973.1|   NAD-dependent DNA ligase [Stre...    504    6e-141
gi|53732315|ref|ZP_00154070.2|   COG0272: NAD-dependent DNA lig...    503    1e-140
gi|3800758|gb|AAC68862.1|   thermostable DNA ligase [Thermus filif    502    2e-140
gi|71482342|ref|ZP_00662037.1|   NAD-dependent DNA ligase [Pros...    502    2e-140
gi|11513387|pdb|1DGS|B   Chain B, Crystal Structure Of Nad+-Dep...    502    2e-140
Related structures
gi|15620219|gb|AAL03634.1|   DNA ligase [EC:6.5.1.2] [Rickettsi...    501    4e-140
gi|67458584|ref|YP_246208.1|   DNA ligase [Rickettsia felis URR...    501    4e-140
gi|32447124|emb|CAD76950.1|   DNA ligase [Rhodopirellula baltic...    499    2e-139
gi|87301433|ref|ZP_01084273.1|   DNA ligase [Synechococcus sp. ...    499    2e-139
gi|86142854|ref|ZP_01061293.1|   DNA ligase [Flavobacterium sp....    499    2e-139
gi|86135717|ref|ZP_01054298.1|   DNA ligase [Tenacibaculum sp. ...    499    2e-139
gi|62463022|ref|ZP_00382379.1|   COG0272: NAD-dependent DNA lig...    497    8e-139
gi|19747987|gb|AAL97474.1|   putative DNA ligase [Streptococcus...    496    1e-138
gi|71853168|gb|AAZ51191.1|   NAD-dependent DNA ligase [Streptoc...    496    1e-138
gi|50903010|gb|AAT86725.1|   NAD-dependent DNA ligase [Streptoc...    496    2e-138
gi|33641228|emb|CAE22358.1|   NAD-dependent DNA ligase [Prochlo...    496    2e-138
gi|71802312|gb|AAX71665.1|   NAD-dependent DNA ligase [Streptoc...    496    2e-138
gi|52699305|ref|ZP_00340713.1|   COG0272: NAD-dependent DNA lig...    496    2e-138
gi|62514545|ref|ZP_00386045.1|   COG0272: NAD-dependent DNA lig...    496    2e-138
gi|21904217|gb|AAM79098.1|   putative DNA ligase [Streptococcus...    495    3e-138
gi|27903967|gb|AAO26801.1|   DNA ligase [Buchnera aphidicola st...    495    3e-138
gi|89337972|ref|ZP_01190750.1|   Helix-hairpin-helix motif:BRCT...    494    4e-138
gi|15458641|gb|AAK99828.1|   DNA ligase [Streptococcus pneumoni...    494    5e-138
gi|68551934|ref|ZP_00591327.1|   NAD-dependent DNA ligase [Pros...    494    5e-138
gi|69933469|ref|ZP_00628671.1|   NAD-dependent DNA ligase [Para...    493    1e-137
gi|14972593|gb|AAK75228.1|   DNA ligase, NAD-dependent [Strepto...    492    2e-137
gi|24379931|ref|NP_721886.1|   DNA ligase [Streptococcus mutans...    492    3e-137
gi|67937159|ref|ZP_00530139.1|   NAD-dependent DNA ligase [Chlo...    492    3e-137
gi|33238820|gb|AAQ00885.1|   NAD-dependent DNA ligase [Prochlor...    491    4e-137
gi|46401035|emb|CAF24484.1|   probable DNA ligase [Parachlamydi...    490    1e-136
gi|3861252|emb|CAA15151.1|   DNA LIGASE (lig) [Rickettsia prowa...    488    5e-136
gi|88713677|ref|ZP_01107759.1|   DNA ligase [Flavobacteriales b...    488    5e-136
```

Figure 6A-7

```
gi|84500836|ref|ZP_00999071.1|  DNA ligase, NAD-dependent [Oce...     488   5e-136
gi|71674111|ref|ZP_00671858.1|  NAD-dependent DNA ligase [Tric...     486   1e-135
gi|67918323|ref|ZP_00511922.1|  NAD-dependent DNA ligase [Chlo...     486   2e-135
gi|6459863|gb|AAF11619.1|  DNA ligase [Deinococcus radiodurans...     485   2e-135
gi|54017744|dbj|BAD59114.1|  putative DNA ligase [Nocardia far...     484   5e-135
gi|71839770|ref|ZP_00679512.1|  NAD-dependent DNA ligase [Pelo...     484   7e-135
gi|33519955|ref|NP_878787.1|  DNA ligase [Candidatus Blochmann...     483   9e-135
gi|2791611|emb|CAA16099.1|  PROBABLE DNA LIGASE [NAD DEPENDENT...      483   9e-135
gi|13882885|gb|AAK47423.1|  DNA ligase [Mycobacterium tubercul...     483   9e-135
gi|90203538|ref|ZP_01206183.1|  DNA ligase (NAD+) [Mycobacteri...     482   2e-134
gi|7674016|sp|Q9WXV5|DNLJ_THEMA  DNA ligase (Polydeoxyribonucl...      481   4e-134
gi|55379625|ref|YP_137475.1|  DNA ligase [Haloarcula marismort...     480   8e-134
gi|51460202|gb|AAU04165.1|  DNA ligase (NAD+); DNA joinase.; D...     479   1e-133
gi|83857007|ref|ZP_00950535.1|  DNA ligase [Croceibacter atlan...     479   1e-133
gi|67988167|gb|EAM75949.1|  NAD-dependent DNA ligase [Kineococ...     479   2e-133
gi|90424785|ref|YP_533155.1|  DNA ligase, NAD-dependent [Rhodo...     478   3e-133
gi|76801093|ref|YP_326101.1|  DNA ligase (NAD) [Natronomonas p...     478   4e-133
gi|47169438|pdb|1V9P|B  Chain B, Crystal Structure Of Nad+-Dep...      478   5e-133
Related structures
gi|67938714|ref|ZP_00531235.1|  NAD-dependent DNA ligase [Chlo...     476   1e-132
gi|50840696|gb|AAT83363.1|  DNA ligase [Propionibacterium acne...     476   2e-132
gi|23024485|ref|ZP_00063695.1|  COG0272: NAD-dependent DNA lig...     474   4e-132
gi|77686561|ref|ZP_00801903.1|  NAD-dependent DNA ligase [Alka...     474   4e-132
gi|71367840|ref|ZP_00658356.1|  NAD-dependent DNA ligase [Noca...     474   5e-132
gi|83951899|ref|ZP_00960631.1|  DNA ligase, NAD-dependent [Ros...     473   9e-132
gi|88803633|ref|ZP_01119157.1|  putative DNA ligase [Polaribac...     473   1e-131
gi|11967289|gb|AAG42042.1|  NAD-dependent DNA ligase [Aquifex pyr    472   3e-131
gi|66964291|ref|ZP_00411861.1|  NAD-dependent DNA ligase [Arth...     471   4e-131
gi|62516483|ref|ZP_00387834.1|  COG0272: NAD-dependent DNA lig...     470   8e-131
gi|21223850|ref|NP_629629.1|  DNA ligase [Streptomyces coelico...     470   1e-130
gi|7673992|sp|O66880|DNLJ_AQUAE  DNA ligase (Polydeoxyribonucl...      470   1e-130
gi|58254173|gb|AAV42410.1|  DNA ligase [Lactobacillus acidophi...     469   2e-130
gi|72161007|ref|YP_288664.1|  DNA ligase [Thermobifida fusca Y...     469   2e-130
gi|42410355|gb|AAS14465.1|  DNA ligase, NAD-dependent [Wolbach...     468   4e-130
gi|84498237|ref|ZP_00997034.1|  DNA ligase [Janibacter sp. HTC...     467   9e-130
gi|33235993|gb|AAP98083.1|  DNA ligase (NAD+) [Chlamydophila p...     466   1e-129
gi|88658391|ref|YP_507122.1|  DNA ligase, NAD-dependent [Ehrli...     466   1e-129
gi|58696662|ref|ZP_00372215.1|  DNA ligase, NAD-dependent [Wol...     466   2e-129
gi|23493177|dbj|BAC18148.1|  putative DNA ligase [Corynebacter...     465   3e-129
gi|38199932|emb|CAE49600.1|  DNA ligase [Corynebacterium dipht...     462   2e-128
gi|23002693|ref|ZP_00046367.1|  COG0272: NAD-dependent DNA lig...     461   4e-128
gi|2414536|emb|CAB16425.1|  DNA ligase [Mycobacterium leprae] ...     461   6e-128
gi|89054995|ref|YP_510446.1|  DNA ligase, NAD-dependent [Janna...     460   1e-127
gi|56678299|gb|AAV94965.1|  DNA ligase, NAD-dependent [Silicib...     460   1e-127
gi|62425239|ref|ZP_00380375.1|  COG0272: NAD-dependent DNA lig...     460   1e-127
gi|42519595|ref|NP_965525.1|  NAD-dependent DNA ligase [Lactob...     459   1e-127
gi|62148272|emb|CAH64037.1|  putative DNA ligase [Chlamydophil...     459   1e-127
gi|88607345|ref|YP_504763.1|  DNA ligase, NAD-dependent [Anapl...     459   2e-127
gi|48866243|ref|ZP_00320099.1|  COG0272: NAD-dependent DNA lig...     459   2e-127
gi|82747660|ref|ZP_00910155.1|  NAD-dependent DNA ligase [Clos...     459   2e-127
gi|29829290|ref|NP_823924.1|  DNA ligase [Streptomyces avermit...     456   1e-126
gi|73667316|ref|YP_303332.1|  NAD-dependent DNA ligase [Ehrlic...     456   2e-126
gi|89898194|ref|YP_515304.1|  DNA ligase [Chlamydophila felis ...     456   2e-126
gi|13422903|gb|AAK23501.1|  DNA ligase, NAD-dependent [Cauloba...     454   4e-126
gi|58417060|emb|CAI28173.1|  DNA ligase [Ehrlichia ruminantium...     452   2e-125
gi|50363531|gb|AAT75516.1|  DNA ligase, polydeoxyribonucleotid...     452   3e-125
gi|58579393|ref|YP_197605.1|  DNA ligase [Ehrlichia ruminantiu...     452   3e-125
gi|56416472|ref|YP_153546.1|  DNA ligase [Anaplasma marginale ...     451   6e-125
gi|34483813|emb|CAE10810.1|  DNA LIGASE POLYDEOXYRIBONUCLEOTID...     449   1e-124
gi|29834724|gb|AAP05359.1|  DNA ligase [Chlamydophila caviae G...     449   2e-124
```

Figure 6A-8

```
gi|69297654|ref|ZP_00619950.1|  NAD-dependent DNA ligase [Sili...    448    4e-124
gi|41325467|emb|CAF19947.1|     DNA LIGASE [Corynebacterium gluta... 447    5e-124
gi|68536402|ref|YP_251107.1|    DNA ligase [Corynebacterium jeik... 447    9e-124
gi|18145924|dbj|BAB81965.1|     DNA ligase [Clostridium perfringe... 445   3e-123
gi|58419121|gb|AAW71136.1|      NAD-dependent DNA ligase, Lig [Wol... 443  1e-122
gi|7190466|gb|AAF39279.1|       DNA ligase [Chlamydia muridarum Nig... 442 3e-122
gi|15025704|gb|AAK80620.1|      NAD-dependent DNA ligase [Clostrid... 439   2e-121
gi|25166391|dbj|BAC24581.1|     lig [Wigglesworthia glossinidia e... 439    2e-121
gi|71061838|gb|AAZ20841.1|      DNA ligase [Candidatus Pelagibacte... 438   3e-121
gi|78498082|gb|ABB44622.1|      DNA ligase (NAD+) [Thiomicrospira ... 436   2e-120
gi|83319601|ref|YP_424672.1|    DNA ligase, NAD-dependent [Mycop... 436    2e-120
gi|76167391|gb|AAX50399.1|      NAD-dependent DNA ligase [Chlamydi... 431   5e-119
gi|42561289|ref|NP_975740.1|    DNA ligase [Mycoplasma mycoides ... 430    9e-119
gi|85702769|ref|ZP_01033873.1|  DNA ligase, NAD-dependent [Ros... 430      1e-118
gi|3328547|gb|AAC67737.1|       DNA Ligase [Chlamydia trachomatis D... 429 2e-118
gi|32263355|gb|AAP78400.1|      DNA ligase [Helicobacter hepaticus... 429  2e-118
gi|86138407|ref|ZP_01056981.1|  DNA ligase, NAD-dependent [Ros... 429      2e-118
gi|4235374|gb|AAD13190.1|       NAD-dependent DNA ligase [Thermus ther 429 3e-118
gi|28211984|ref|NP_782928.1|    DNA ligase [Clostridium tetani E... 428    3e-118
gi|19712952|gb|AAL93832.1|      NAD-dependent DNA ligase [Fusobact... 426   2e-117
gi|66877873|ref|ZP_00403391.1|  COG0272: NAD-dependent DNA lig... 426      2e-117
gi|4235378|gb|AAD13192.1|       NAD-dependent DNA ligase [Thermus fili 425 3e-117
gi|56807783|ref|ZP_00365637.1|  COG0272: NAD-dependent DNA lig... 425      4e-117
gi|88855225|ref|ZP_01129890.1|  DNA ligase [marine actinobacte... 422      2e-116
gi|39722033|dbj|BAD04523.1|     NAD-dependent DNA ligase [Onion y... 419   3e-115
gi|88608555|ref|YP_506384.1|    DNA ligase, NAD-dependent [Neori... 418    5e-115
gi|4235372|gb|AAD13189.1|       NAD-dependent DNA ligase [Thermus aqua 416 2e-114
gi|4155109|gb|AAD06141.1|       DNA LIGASE [Helicobacter pylori J99... 414 5e-114
gi|4235380|gb|AAD13193.1|       NAD-dependent DNA ligase [Thermus sp. 413 1e-113
gi|50951550|gb|AAT89251.1|      DNA ligase [Leifsonia xyli subsp. ... 413  1e-113
gi|85057601|ref|YP_456517.1|    NAD-dependent DNA ligase [Aster ... 411    4e-113
gi|57241999|ref|ZP_00369939.1|  DNA ligase, NAD-dependent [Cam... 410      7e-113
gi|4235376|gb|AAD13191.1|       NAD-dependent DNA ligase [Thermus fili 406 2e-111
gi|15645240|ref|NP_207410.1|    DNA ligase [Helicobacter pylori ... 405    2e-111
gi|15024117|gb|AAK79167.1|      DNA ligase (NAD dependent), LigA [... 404  7e-111
gi|6968053|emb|CAB75222.1|      DNA ligase [Campylobacter jejuni s... 403 1e-110
gi|57167022|gb|AAW35801.1|      DNA ligase, NAD-dependent [Campylo... 402 2e-110
gi|86151833|ref|ZP_01070047.1|  DNA ligase, NAD-dependent [Cam... 401      4e-110
gi|13508096|ref|NP_110045.1|    DNA ligase [Mycoplasma pneumonia... 401    6e-110
gi|57241143|ref|ZP_00369090.1|  DNA ligase, NAD-dependent [Cam... 399      3e-109
gi|26553637|ref|NP_757571.1|    NAD-dependent DNA ligase [Mycopl... 397    6e-109
gi|87304616|ref|ZP_01086772.1|  DNA ligase, NAD-dependent [Cam... 397      1e-108
gi|86153540|ref|ZP_01071744.1|  DNA ligase, NAD-dependent [Cam... 397      1e-108
gi|21225788|ref|NP_631567.1|    DNA ligase [Streptomyces coelico... 390    1e-106
gi|4235382|gb|AAD13194.1|       NAD-dependent DNA ligase [Thermus sp. 386 1e-105
gi|86154310|ref|ZP_01072478.1|  DNA ligase, NAD-dependent [Cam... 385      4e-105
gi|12045108|ref|NP_072919.1|    DNA ligase [Mycoplasma genitaliu... 382    2e-104
gi|67809897|gb|AAY81980.1|      NAD-dependent DNA ligase [Wolbachia p 381  6e-104
gi|6899079|gb|AAF30527.1|       DNA ligase [Ureaplasma parvum serov... 379 2e-103
gi|67546384|ref|ZP_00424298.1|  DNA ligase (NAD+) [Burkholderi... 374      8e-102
gi|71481729|ref|ZP_00661433.1|  NAD-dependent DNA ligase [Pros... 370      1e-100
gi|85667631|ref|ZP_01029848.1|  hypothetical protein Badol_010... 358      6e-97
gi|13235527|emb|CAC33654.1|     DNA ligase [Rickettsia montanensis] 357    1e-96
gi|13235515|emb|CAC33719.1|     DNA ligase [Rickettsia rickettsii] 356     2e-96
gi|24216818|ref|NP_714299.1|    DNA ligase [Leptospira interroga... 351    5e-95
gi|45659103|ref|YP_003189.1|    NAD dependent DNA ligase [Leptos... 351    5e-95
gi|1770452|emb|CAA66920.1|      ligase-like protein [Homo sapiens] 350     2e-94
gi|54016384|dbj|BAD57754.1|     putative DNA ligase [Nocardia far... 348   5e-94
gi|23464680|ref|NP_695283.1|    LigA [Bifidobacterium longum NCC... 345    5e-93
gi|23336066|ref|ZP_00121295.1|  COG0272: NAD-dependent DNA lig... 345      5e-93
```

Figure 6A-9

```
gi|13235502|emb|CAC33764.1|  DNA ligase [Rickettsia typhi]          342    4e-92
gi|81252942|ref|ZP_00877513.1|  COG0272: NAD-dependent DNA lig...   338    4e-91
gi|2688477|gb|AAC66923.1|   DNA ligase (lig) [Borrelia burgdorf...  333    2e-89
gi|51573374|gb|AAU07399.1|   DNA ligase [Borrelia garinii PBi] ...  332    3e-89
gi|31541751|gb|AAP57050.1|   Lig [Mycoplasma gallisepticum R] >...  332    3e-89
gi|83586931|ref|ZP_00925562.1|  COG0272: NAD-dependent DNA lig...   324    7e-87
gi|82548271|gb|ABB82962.1|   NAD-dependent DNA ligase [uncultured   324    9e-87
gi|57168176|ref|ZP_00367315.1|  DNA ligase (NAD) Cj0586 [Campy...   313    2e-83
gi|47458358|gb|AAT27681.1|   NAD(+)-dependent DNA ligase [Mycop...  312    4e-83
gi|80159718|ref|YP_398462.1|   putative NAD-dependent DNA ligas...  306    2e-81
gi|71894578|ref|YP_278686.1|   DNA ligase [Mycoplasma synoviae ...  306    3e-81
gi|6573452|pdb|1B04|B   Chain B, Structure Of The Adenylation D...  306    3e-81
Related structures
gi|28572508|ref|NP_789288.1|   DNA ligase [Tropheryma whipplei ...  303    1e-80
gi|28493381|ref|NP_787542.1|   DNA ligase [Tropheryma whipplei ...  303    1e-80
gi|71913729|gb|AAZ53640.1|   DNA ligase [Mycoplasma hyopneumoni...  298    7e-79
gi|71851741|gb|AAZ44349.1|   DNA ligase [Mycoplasma hyopneumoni...  296    2e-78
gi|54020343|ref|YP_115627.1|   DNA ligase [Mycoplasma hyopneumo...  295    3e-78
gi|56966057|pdb|1TA8|A   Chain A, Structural Rearrangement Acco... 295    3e-78
Related structures
gi|56966061|pdb|1TAE|D   Chain D, Structural Rearrangement Acco... 294    8e-78
Related structures
gi|75853525|ref|ZP_00761354.1|  COG0272: NAD-dependent DNA lig...   294    1e-77
gi|37788926|gb|AAO65604.1|   hypothetical NAD-dependent DNA ligase  290    2e-76
gi|34764322|ref|ZP_00145154.1|   NAD-DEPENDENT DNA LIGASE [Fuso... 278    6e-73
gi|46204823|ref|ZP_00049431.2|  COG0272: NAD-dependent DNA lig...   260    2e-67
```

Figure 6B-1

```
gi|9632609|ref|NP_049813.1|    gp30 DNA ligase [Enterobacteria p...    971    0.0
gi|118771|sp|P19088|DNLI_BPT6   DNA ligase (Polydeoxyribonucleo...    962    0.0
gi|32453693|ref|NP_861902.1|    gp30 DNA ligase [Enterobacteria ...    590    5e-167
gi|33620630|ref|NP_891784.1|    DNA ligase [Enterobacteria phage...    353    7e-96
gi|66391546|ref|YP_239071.1|    gp30 DNA ligase [Enterobacteria ...    316    1e-84
gi|37651671|ref|NP_932545.1|    DNA ligase; gp30 [Bacteriophage ...    310    9e-83
gi|66391992|ref|YP_238871.1|    gp30 DNA ligase [Aeromonas phage...    310    1e-82
gi|38640183|ref|NP_944139.1|    gp30 DNA ligase [Bacteriophage A...    301    3e-80
gi|34419292|ref|NP_899305.1|    DNA ligase [Bacteriophage KVP40]...    284    5e-75
gi|47572743|ref|ZP_00242785.1|   COG1793: ATP-dependent DNA ligase    157    8e-37
gi|29125051|emb|CAD79438.1|     gp30 [Enterobacteria phage RB49]       122    3e-26
gi|45357328|gb|AAS58722.1|      putative DNA ligase [Yersinia pest...   103    1e-20
gi|16506016|emb|CAD09902.1|     putative DNA ligase [Salmonella e...    97.4   1e-18
gi|57867457|ref|YP_189099.1|    DNA ligase, ATP-dependent [Staph...    90.9   1e-16
gi|2996344|gb|AAC13224.1|       DNA ligase homolog [Yersinia pestis KI  88.6   6e-16
gi|40787977|ref|NP_857697.2|    DNA ligase [Yersinia pestis KIM]...    88.6   6e-16
gi|78713656|gb|ABB50833.1|      ATP-dependent DNA ligase [Prochlor...   62.8   3e-08
gi|33634453|emb|CAE20138.1|     ATP-dependent DNA ligase [Prochlo...    60.8   1e-07
gi|12054709|emb|CAC20743.1|     DNA ligase [Pyrococcus abyssi]         57.4   1e-06
gi|83338493|gb|ABC11973.1|      thermostable DNA ligase [Thermococcus  55.5   5e-06
gi|5457975|emb|CAB49465.1|      lig DNA ligase [Pyrococcus abyssi ...   55.1   7e-06
gi|3258051|dbj|BAA30734.1|      559aa long hypothetical DNA ligase...   51.6   8e-05
gi|57160399|dbj|BAD86329.1|     ATP-dependent DNA ligase [Thermoc...    51.6   8e-05
gi|14423676|sp|Q9HHC4|DNLI_PYRKO Thermostable DNA ligase (Pol...       51.6   8e-05
gi|18893788|gb|AAL81759.1|      DNA ligase (lig) [Pyrococcus furio...   48.9   5e-04
gi|57505297|ref|ZP_00371226.1|  DNA ligase, ATP-dependent [Cam...     48.9   5e-04
gi|85373652|ref|YP_457714.1|    hypothetical protein ELI_04125 [...    48.5   6e-04
gi|66392078|ref|YP_239300.1|    possible DNA ligase [Xanthomonas...    48.1   8e-04
gi|77952115|ref|ZP_00816532.1|  DNA ligase, ATP-dependent [Mar...     48.1   8e-04
gi|87305517|ref|ZP_01087672.1|  DNA ligase [Campylobacter jeju...     47.8   0.001
gi|57167484|gb|AAW36263.1|      DNA ligase, ATP-dependent [Campylo...  46.6   0.002
gi|9628207|ref|NP_042793.1|     DNA ligase [African swine fever v...   46.6   0.002
gi|50405282|ref|YP_054374.1|    DNA ligase, putative [Paramecium...    46.2   0.003
gi|6969085|emb|CAB73656.1|      putative ATP-dependent DNA ligase ...   46.2   0.003
gi|86152214|ref|ZP_01070425.1|  DNA ligase, ATP-dependent [Cam...     46.2   0.003
gi|12056098|emb|CAC21199.1|     DNA ligase [Thermococcus fumicola...   45.4   0.005
gi|57504663|ref|ZP_00370741.1|  DNA ligase [Campylobacter coli...     45.4   0.005
gi|86152959|ref|ZP_01071164.1|  DNA ligase [Campylobacter jeju...     45.4   0.005
gi|78691018|ref|ZP_00855651.1|  DNA ligase, ATP-dependent [She...     45.1   0.007
gi|78686734|ref|ZP_00851497.1|  DNA ligase, ATP-dependent [She...     45.1   0.007
gi|82497088|ref|ZP_00882648.1|  DNA ligase, ATP-dependent [She...     45.1   0.007
gi|450697|emb|CAA50805.1|       DNA ligase [African swine fever vir...  44.7   0.009
gi|78497323|gb|ABB43863.1|      ATP dependent DNA ligase, central ...   43.5   0.021
gi|89900229|ref|YP_522700.1|    ATP dependent DNA ligase [Rhodof...    43.1   0.027
gi|19887522|gb|AAM02212.1|      ATP-dependent DNA ligase [Methanop...   42.4   0.046
gi|18159655|gb|AAL63064.1|      DNA ligase [Pyrobaculum aerophilum...   42.4   0.046
gi|4099066|gb|AAD00532.1|       DNA ligase [Pyrobaculum aerophilum]    42.4   0.046
gi|19914533|gb|AAM04168.1|      DNA ligase (ATP) [Methanosarcina a...   42.0   0.061
gi|39575917|emb|CAE80083.1|     lig [Bdellovibrio bacteriovorus H...   41.2   0.10
gi|15076131|emb|CAC47685.1|     PUTATIVE GLUTAMATE 5-KINASE PROTE...   41.2   0.10
gi|22001838|sp|Q92LF7|PROB2_RHIME  Glutamate 5-kinase 2 (Gamma-gl    41.2   0.10
gi|72396566|gb|AAZ70839.1|      DNA ligase (ATP) [Methanosarcina b...   40.8   0.14
gi|56180164|gb|AAV82886.1|      ATP-dependent DNA ligase [Idiomari...   40.4   0.18
gi|2983805|gb|AAC07362.1|       DNA ligase (ATP dependent) [Aquifex...  40.4   0.18
gi|14423667|sp|O67398|DNLI_AQUAE  Probable DNA ligase (Polydeoxyr    40.4   0.18
gi|68234370|ref|ZP_00573454.1|  ATP-dependent DNA ligase [Fran...    40.4   0.18
gi|84495581|ref|ZP_00994700.1|  DNA ligase [Janibacter sp. HTC...    40.4   0.18
gi|1279773|gb|AAC44823.1|       DNA ligase >gi|1706484|sp|P54875|DN...  40.0   0.23
gi|77118174|ref|YP_338096.1|    ligase [Enterobacteria phage K1F...   39.7   0.30
gi|15621187|dbj|BAB65183.1|     600aa long hypothetical DNA ligas...   39.7   0.30
gi|68299729|ref|YP_249578.1|    DNA ligase [Vibriophage VP4] >gi...   38.9   0.51
gi|15141279|emb|CAC49792.1|     conserved hypothetical protein [S...   38.9   0.51
gi|52307046|gb|AAU37546.1|      CDC9 protein [Mannheimia succinici...   38.9   0.51
gi|21228816|ref|NP_634738.1|    ATP-dependent DNA ligase [Methan...   38.9   0.51
gi|24373759|ref|NP_717802.1|    DNA ligase [Shewanella oneidensi...   38.5   0.67
gi|66825971|ref|XP_646340.1|    putative transmembrane protein [...   38.5   0.67
gi|88950928|ref|ZP_01153502.1|  ATP-dependent DNA ligase [Meth...    38.5   0.67
gi|86155280|ref|ZP_01073445.1|  DNA ligase [Campylobacter fetu...    38.5   0.67
gi|78364299|gb|ABB42264.1|      ATP dependent DNA ligase, central ...  38.1   0.88
gi|84489085|ref|YP_447317.1|    ATP-dependent DNA ligase [Methan...   38.1   0.88
gi|73969957|ref|XP_531761.2|    PREDICTED: similar to CG16721-PA [C   38.1   0.88
```

Figure 6B-2

```
gi|11499314|ref|NP_070553.1|   DNA ligase, putative [Archaeoglo...   37.7   1.1
gi|33300828|ref|NP_877456.1|   putative ATP-dependent DNA ligas...   37.7   1.1
gi|90575473|ref|ZP_01231956.1| hypothetical protein CdifQ_020...     37.7   1.1
gi|19916535|gb|AAM05952.1|     DNA ligase (ATP) [Methanosarcina a... 37.7   1.1
gi|7341364|gb|AAF61267.1|      DNA ligase [Sulfolobus shibatae] >g... 37.7  1.1
gi|2447051|gb|AAC96909.1|      PBCV-1 DNA ligase [Paramecium bursa... 37.4  1.5
gi|70802220|gb|AAZ12125.1|     DNA ligase, putative [Trypanosoma ... 37.4   1.5
gi|75819286|ref|ZP_00749374.1| COG1793: ATP-dependent DNA ligase    37.4   1.5
gi|34810336|pdb|1P8L|A  Chain A, New Crystal Structure Of Chlo...   37.4   1.5
Related structures
gi|84496262|ref|ZP_00995116.1| DNA ligase [Janibacter sp. HTC...    37.4   1.5
gi|11513551|pdb|1FVI|A  Chain A, Crystal Structure Of Chlorell...   37.4   1.5
Related structures
gi|23495058|gb|AAN35390.1|     hypothetical protein PF10_0192 [Pl... 36.6   2.5
gi|87162927|gb|ABD28722.1|     Prefoldin [Medicago truncatula]      36.6   2.5
gi|37181034|gb|AAQ88427.1|     kinetoplast DNA ligase k beta [Crithi 36.2  3.3
gi|1590924|gb|AAB98156.1|      DNA ligase (lig) [Methanocaldococcu... 36.2  3.3
gi|89293628|gb|EAR91616.1|     ATP dependent DNA ligase domain co... 36.2   3.3
gi|87122257|ref|ZP_01078139.1| DNA ligase [Marinomonas sp. ME...    36.2   3.3
gi|2914565|pdb|5CSM|A   Chain A, Yeast Chorismate Mutase, T226s...  36.2   3.3
Related structures
gi|50426391|ref|XP_461792.1|   hypothetical protein DEHA0G06292...  35.8   4.3
gi|50407330|ref|XP_456702.1|   hypothetical protein DEHA0A08734...  35.8   4.3
gi|11068104|ref|NP_068320.1|   PxORF101 peptide [Plutella xylos...  35.8   4.3
gi|27383142|ref|NP_774671.1|   similar to DNA ligase [Bradyrhiz...  35.8   4.3
gi|11498231|ref|NP_069457.1|   DNA ligase (lig) [Archaeoglobus ...  35.8   4.3
gi|14424444|sp|O29632|DNLI_ARCFU DNA ligase (Polydeoxyribonucleo    35.8   4.3
gi|90420845|ref|ZP_01228750.1| ATP dependent DNA ligase [Aura...    35.8   4.3
gi|89305214|gb|EAS03202.1|     hypothetical protein TTHERM_005353... 35.8   4.3
gi|69953539|ref|ZP_00640634.1| ATP-dependent DNA ligase [Shew...    35.8   4.3
gi|60098361|emb|CAH65011.1|    hypothetical protein [Gallus gallus] 35.4   5.7
gi|71006542|ref|XP_757937.1|   hypothetical protein UM01790.1 [...  35.4   5.7
gi|2622703|gb|AAB86053.1|      DNA ligase [Methanothermobacter the... 35.4  5.7
gi|9656048|gb|AAF94696.1|      DNA ligase [Vibrio cholerae O1 biov... 35.4  5.7
gi|33568539|emb|CAE34297.1|    molecular chaperone [Bordetella b... 35.4   5.7
gi|33572838|emb|CAE42771.1|    molecular chaperone [Bordetella p... 35.4   5.7
gi|68547601|ref|ZP_00587134.1| ATP-dependent DNA ligase [Shew...    35.4   5.7
gi|75814149|ref|ZP_00744782.1| COG1793: ATP-dependent DNA ligase   35.4   5.7
gi|2914555|pdb|3CSM|B   Chain B, Structure Of Yeast Chorismate ... 35.4   5.7
Related structures
gi|68127207|emb|CAJ05229.1|    DNA ligase, putative; mitochondri... 35.0   7.4
gi|37679818|ref|NP_934427.1|   DNA ligase [Vibrio vulnificus YJ... 35.0   7.4
gi|29542491|gb|AAO91425.1|     DNA ligase, ATP-dependent [Coxiell... 35.0  7.4
gi|9635391|ref|NP_059289.1|    ORF141 [Xestia c-nigrum granulovi... 35.0   7.4
gi|44043|emb|CAA48381.1|       nisB [Lactococcus lactis] >gi|417366... 35.0 7.4
gi|34495765|ref|NP_899980.1|   hypothetical protein CV0310 [Chr... 35.0   7.4
gi|66803232|ref|XP_635459.1|   hypothetical protein DDB0219636 ...  35.0   7.4
gi|28806468|dbj|BAC59740.1|    DNA ligase [Vibrio parahaemolytic... 35.0   7.4
gi|27362098|gb|AAO11004.1|     ATP-dependent DNA ligase [Vibrio v... 35.0  7.4
gi|33238054|gb|AAQ00121.1|     Predicted protein [Prochlorococcus... 35.0  7.4
gi|68067465|ref|XP_675696.1|   hypothetical protein PB000113.03...  35.0   7.4
gi|89290626|gb|EAR88614.1|     hypothetical protein TTHERM_001858... 35.0  7.4
gi|89209927|ref|ZP_01188321.1| ATP dependent DNA ligase, cent...    35.0   7.4
gi|86171519|ref|XP_966228.1|   hypothetical protein PFF1185w [P...  34.7   9.7
gi|86170605|ref|XP_966048.1|   DNA repair protein [Plasmodium f...  34.7   9.7
gi|20517566|gb|AAM25682.1|     Transcriptional regulator [Thermoa... 34.7   9.7
gi|15075146|emb|CAC46703.1|    PUTATIVE MEMBRANE BOUND PROTEASE ... 34.7   9.7
gi|50363726|gb|AAT75711.1|     putative chromosome segregation AT... 34.7  9.7
gi|40786|emb|CAA45034.1|       DNa ligase [Acidianus ambivalens] >g... 34.7 9.7
gi|82704891|ref|XP_726740.1|   helicase [Plasmodium yoelii yoel...  34.7   9.7
gi|71147081|gb|AAZ27554.1|     dihydroorotate dehydrogenase [Colw... 34.7  9.7
```

Figure 7 (SEQ ID NO:11)

```
atgccgcgct acgggttcca cctttccatc gccgggaaaa agggcgtggc cggggcggtg gaggaggcca ccgccctcgg cctcaccgct ttccagatct tcgccaaaag cccgcggagc tggcgcccaa gggccctctc cccggccgag gtggaggcct tccgcgcctt aagggaggcc tccgggggcc tccccgccgt gatccacgcc tcctacctgg tcaacctggg ggcggagggg gagctttggg agaagagcgt ggcgagcctg gcggacgacc tggagaaggc cgccctcctc ggggtggagt acgtggtcgt ccaccccggc tcgggccgcc ccgagcgggt caaggaaggg gccctcaagg ccctgcgcct cgccggcgtc cgctcccgcc ccgtcctcct cgtggagaac accgccgggg gcggggagaa ggtggggcg cggtttgagg agctcgcctg gctcgtggcg gacaccccccc tccaggtctg cctggacacc tgccacgcct acgccgccgg gtacgacgtg gccgaggacc ccttgggggt cctggacgcc ctggaccggg ccgtgggcct ggagcgggtg cccgtggtcc acctcaacga ctccgtgggc ggcctcggaa gccgcgtgga ccaccacgcc cacctcctcc agggaaagat cggggagggg ctcaagcgcg tcttcttgga cccgaggctc aaggaccggg tcttcatcct ggaaaccccc aggggaccgg aggaggacgc ctggaacctc cgggtcctca gggcctggct cgaggaggcc taa
```

Figure 9
A
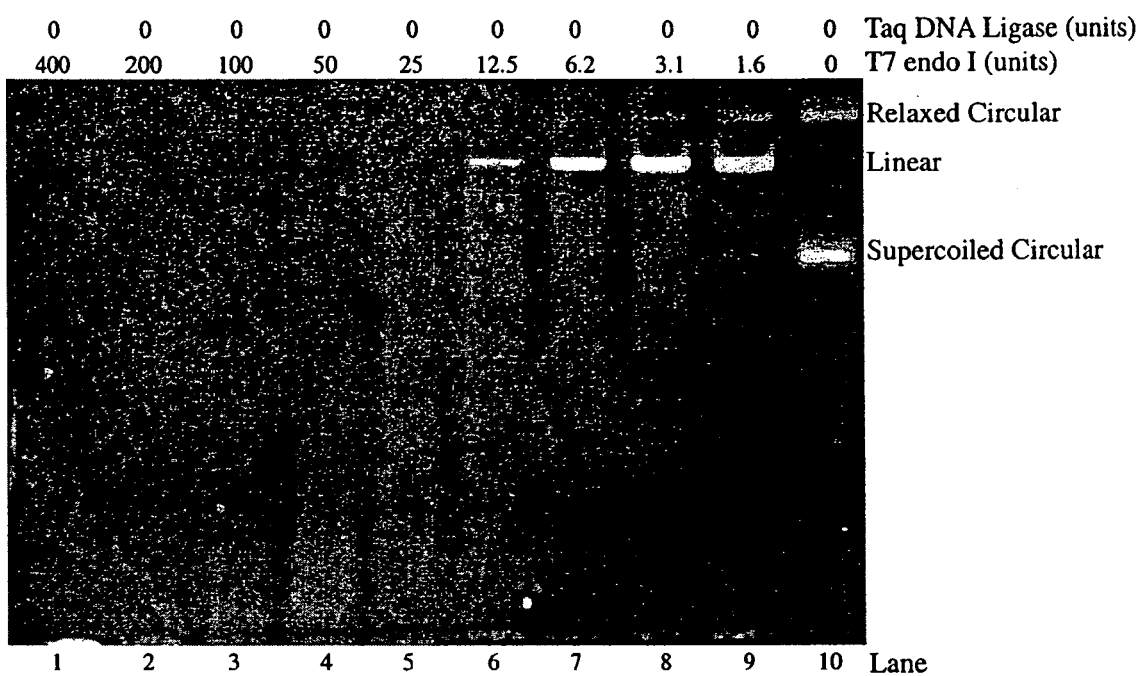
B
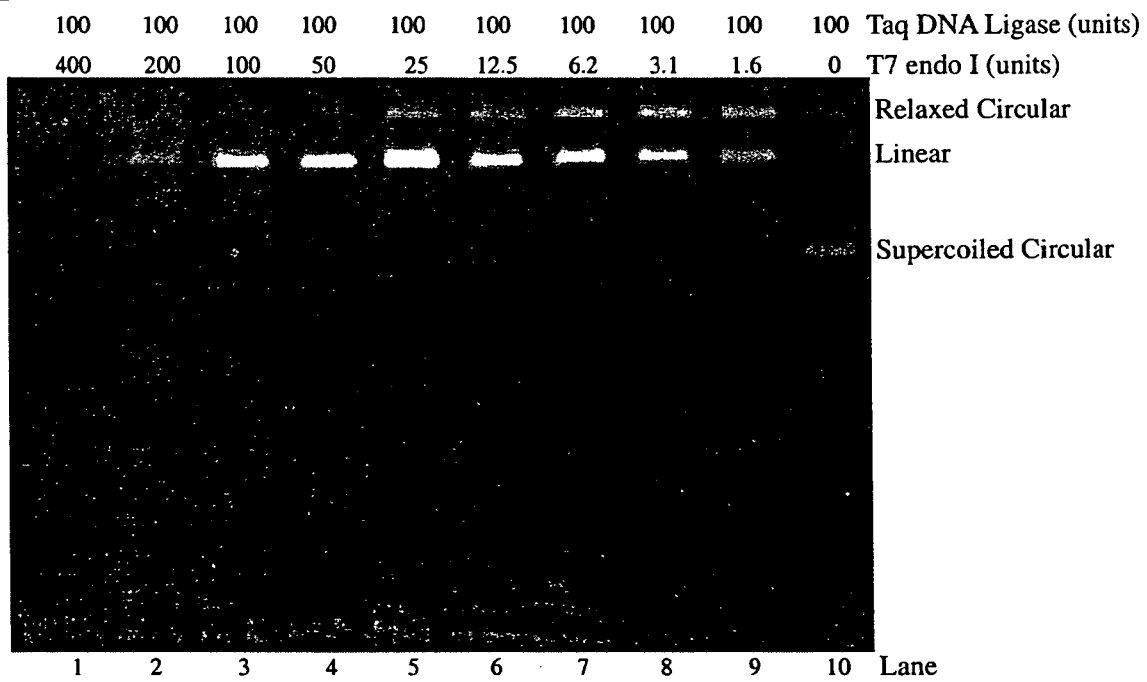

Figure 10
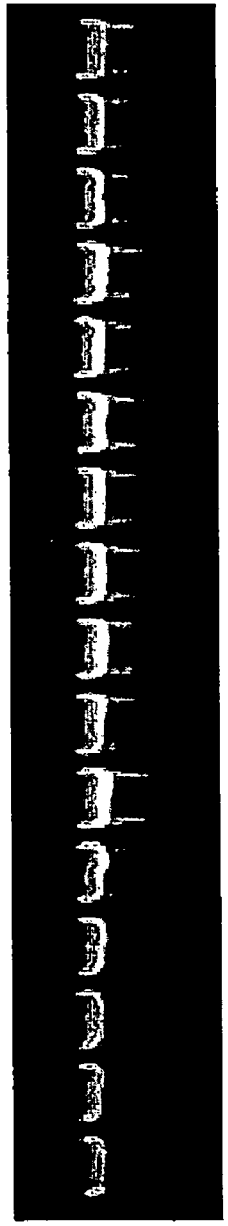
A. no methylene blue
B. 25 μg/mL methylene blue

Figure 18-1

```
GACGAAAGGGCCTCGTGATACGCCTATTTTTATAGGTTAATGTCATGATAATAATGG
TTTCTTAGACGTCAGGTGGCACTTTTCGGGGAAATGTGCGCGGAACCCCTATTTGTT
TATTTTTCTAAATACATTCAAATATGTATCCGCTCATGAGACAATAACCCTGATAAA
TGCTTCAATAATATTGAAAAAGGAAGAGTATGAGTATTCAACATTTCCGTGTCGCCC
TTATTCCCTTTTTTGCGGCATTTTGCCTTCCTGTTTTTGCTCACCCAGAAACGCTGG
TGAAAGTAAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTTCCAATGA
TGAGCACTTTTAAAGTTCTGCTATGTGGCGCGGTATTATCCCGTATTGACGCCGGGC
AAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATC
GTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAG
CTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCCGTATCG
TAGTTATCTACACGACGGGGAGTCAGGCAACTATGGATGAACGAAATAGACAGATCG
CTGAGATAGGTGCCTCACTGATTAAGCATTGGTAACTGTCAGACCAAGTTTACTCAT
ATATACTTTAGATTGATTTAAAACTTCATTTTTAATTTAAAAGGATCTAGGTGAAGA
TCCTTTTTGATAATCTCATGACCAAAATCCCTTAACGTGAGTTTTCGTTCCACTGAG
CGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGTAG
CACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGC
GGTCGGGCTGAACGGGGGGTTCGTGCACACAGCCCAGCTTGGAGCGAACGACCTACA
CCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGG
AGCTTCCAGGGGGAAACGCCTGGTATCTTTATAGTCCTGTCGGGTTTCGCCACCTCT
GACTTGAGCGTCGATTTTTGTGATGCTCGTCAGGGGGCGGAGCCTATGGAAAAACG
CCAGCAACGCGGCCTTTTTACGGTTCCTGGCCTTTTGCTGGCCTTTTGCTCACATGT
TCTTTCCTGCGTTATCCCCTGATTCTGTGGATAACCGTATTACCGCCTTTGAGTGAG
CTGATACCGCTCGCCGCAGCCGAACGACCGAGCGCAGCGAGTCAGTGAGCGAGGAAG
CGGAAGAGCGCCCAATACGCAAACCGCCTCTCCCCGCGCGTTGGCCGATTCATTAAT
GCAGCTGGCACGACAGGTTTCCCGACTGGAAAGCGGGCAGTGAGCGCAACGCAATTA
ATGTGAGTTAGCTCACTCATTAGGCACCCCAGGCTTTACACTTTATGCTTCCGGCTC
GTATGTTGTGTGGAATTGTGAGCGGATAACAATTTCACACAGGAAACAGCTATGACC
ATGATTACGCCAAGCTTCCTGCAGGGTTTAAACGCTGAGGAGACATATGGCCGCCGA
GTCTCAGTTAAAACGTGTGATCGAAACGCTGCGCCGTCTGGGTATTGAAGAGGTGCT
GAAACTGGAACGTCGTGATCCTCAGTATCGCGCTGTTTGCAATGTGGTCAAGCGTCA
TGGCGAAACTGTGGGCAGCCGTTTAGCTATGTTAAACGCCCTGATTTCATATCGCCT
GACCGGTAAGGGTGAGGAGCATTGGGAATATTTCGGCAAATATTTCAGTCAGTTAGA
AGTGATTGATCTGTGCCGTGATTTCTTAAAATATATTGAGACCAGCCCGTTCCTGAA
AATCGGTGTCGAGGCGCGCAAGAAACGCGCGTTAAAGGCCTGCGACTACGTCCCTAA
CTTGGAAGACTTGGGCCTGACCCTGCGTCAATTAAGCCACATCGTTGGTGCACGCCG
TGAGCAGAAGACGTTGGTCTTCACAATCAAGATCCTGAACTATGCATATATGTCAG
CCGCGGTGTTATCGCGTGTTGCCGTTCGATATTCCAATTCCTGTGGATTACCGTGTT
GCACGCTTGACCTGGTGCGCCGGTCTGATCGATTTCCCGCCGGAGGAGGCCTTGCGC
```

Figure 18-2

```
CGCTACGAGGCTGTGCAGAAAATCTGGGATGCCGTGGCGCGCGAAACTGGTATTCCT
CCATTGCACTTGGACACCCTGTTATGGTTGGCCGGTCGCGCGGTGCTGTATGGTGAA
AACCTGCATGGTGTGCCGAAAGAGGTCATCGCTCTGTTCCAATGGCGCGGCGGCTGC
CGTCCGCCTAGCGAGTAAACCCCCTCAGCTTAATTAAGGCGCGCCTGAGCTCGAATT
CACTGGCCGTCGTTTTACAACGTCGTGACTGGGAAAACCCTGGCGTTACCCAACTTA
ATCGCCTTGCAGCACATCCCCCTTTCGCCAGCTGGCGTAATAGCGAAGAGGCCCGCA
CCGATCGCCCTTCCCAACAGTTGCGCAGCCTGAATGGCGAATGGCGCCTGATGCGGT
ATTTTCTCCTTACGCATCTGTGCGGTATTTCACACCGCATATGGTGCACTCTCAGTA
CAATCTGCTCTGATGCCGCATAGTTAAGCCAGCCCCGACACCCGCCAACACCCGCTG
ACGCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGA
```

REPAIR OF NUCLEIC ACIDS FOR IMPROVED AMPLIFICATION

CROSS REFERENCE

This application claims priority from U.S. patent application Ser. No. 11/255,290 filed Oct. 21, 2005, which claims priority from U.S. Provisional Application Ser. No. 60/620,896 filed Oct. 21, 2004, U.S. Provisional Application Ser. No. 60/646,728 filed Jan. 24, 2005 and U.S. Provisional Application Ser. No. 60/673,925 filed Apr. 21, 2005.

BACKGROUND

Copying of polynucleotides, more particularly amplification, is commonly used in molecular biology for studying, for example, the properties of genes. Problems in copying arise when the polynucleotide is damaged in some way.

By way of illustration, U.S. Pat. No. 5,035,996 describes a process for controlling contamination of polymerase chain reaction amplification reactions that uses the modified nucleotide, dUTP, in the amplification reaction. This process uses uracil DNA glycosylase (UDG) to eliminate those PCR products containing uracil to prevent contaminating subsequent PCR reactions. U.S. patent publication No. 2004-0067559 A1 also relies on modified bases in primer DNA prior to amplification and uses, for example, dUTP for incorporation into the amplicon. The amplicon can then be fragmented by adding, for example, UDG and Endonuclease (Endo) IV.

One amplification methodology referred to as hot start nucleic acid amplification has been used to lower mis-priming during polymerase chain reaction (PCR). In one type of hot start amplification, prevention of extension by the polymerase relies on the presence of a PCR primer with a blocked 3' terminus in the PCR reaction (see for example U.S. Publication No. 2003-0119150). The primer is unblocked by a thermostable 3'-5' exonuclease that is active at >37° C. Therefore, the polymerase will only extend the PCR primers once the exonuclease unblocks the 3' end at >37° C. Alternatively the Taq polymerase is blocked and then activated at amplification temperatures.

Barnes, W. M. *Proc. Natl. Acad. Sci. USA* 91:2216-2220 (1994) describes the use of Vent® polymerase and Taq polymerase as an improvement over the use of Taq polymerase only in amplification. Ghadessy et al. reported a mutant Taq polymerase that is not halted by damaged or abasic sites (Ghadessy et al. *Nature Biotechnol.* 22(6):755-9 (2004)).

It has been reported that conventional amplification techniques are compromised if the DNA is substantially damaged (Di Bernardo et al. *Nucl. Acids Res.* 30:e16 (2002)). Degradation and/or fragmentation of DNA resulting from exposure to the environment and microorganisms which contain DNA nucleases is a frequent problem in forensics, diagnostic tests and routine amplification and affects fidelity and yield of the amplification product. In addition, the problem of degraded DNA is also faced by researchers who are analyzing the DNA obtained from extinct or extremely rare organisms that have been stored, frozen or fossilized.

Fromenty, B., et al. *Nucl. Acids Res.* 28(11):e50 (2000) and International Publication No. WO/0151656 reported that treatment with Exonuclease (Exo) III improved yields of long PCR. However, Fromenty also reported decreased yields of amplicon for DNA<500 bp when Exo III was used. One of the problems associated with the use of Exo III is that it degrades template and primers.

Di Benardo et al. *Nucl. Acids Res.* 30(4):e16 (2002) described the use of T4 DNA ligase (T4 ligase) and an *E. coli* polymerase as a pretreatment to amplify short regions of single-stranded DNA between cross-linked regions of double-stranded DNA.

Another approach to amplification of damaged DNA has been described in U.S. Publication No. 2003-0077581. Degraded nucleic acid was hybridized to non-degraded nucleic acid having a sequence homologous to the degraded nucleic acid. Regions of the degraded nucleic acid were then filled in with nucleotide precursors. The fragmented strands were then covalently linked using a polymerizing and/or ligating enzyme.

Preparations for improving amplification of damaged DNA can be obtained commercially from Sigma, St. Louis, Mo. and Qbiogene, now MP Biomedicals, Irvine, Calif. Although the compositions of these preparations are not stated, it is assumed that Exo III is contained in the preparation.

Others report the use of a combination of *E. coli* DNA PolI and T4 ligase for pre-amplification repair (Pusch, et al., *Nucl. Acids Res.* 26:857 (1998)). However, according to Pusch et al., the pre-amplification product must be purified before initiation of amplification.

SUMMARY

In an embodiment of the invention, a method is provided for enhancing at least one of fidelity and yield of a copied or amplified product by repairing a damaged polynucleotide where the method may include: incubating the polynucleotide in the absence of Endonuclease VI (Endo VI) in a reaction mixture comprising a ligase and at least one of NAD$^+$ or ATP as a cofactor. The polynucleotide may be derived from any natural or synthetic source including from preserved biological material, forensic evidence, ancient material of biological origin, and tissue biopsy material. Examples of damage to the polynucleotide can include at least one of a apurinic/apyrimidinic (AP) site, a chemically modified nucleotide, a nick, a gap and DNA-DNA, DNA-protein cross-links, DNA-RNA cross-links or RNA-RNA cross-links.

In one example of the method, the ligase is a thermostable ligase. Taq DNA ligase is an example of a thermostable ligase that uses NAD$^+$ as a cofactor. *E. coli* DNA ligase is another example of a ligase where the cofactor is NAD$^+$. Other components of the reaction mixture containing the ligase may include one or more of a T7 Endo I or mutant thereof, a polymerase and an AP endonuclease. Examples of a polymerase for use in the reaction mixture include a Taq polymerase, an *E. coli* polymerase, or an archaeal polymerase or mutant thereof. Examples of archeal polymerases or chimeric polymerases derived therefrom include one or more of a Pfu, Vent®, Deep Vent®, 9° North, KOD, Phusion™ polymerases and Pwo. Examples of other polymerases for use in the reaction mixture include members of the Y family of polymerases such as *E. coli* polIV, *E. coli* poly, human pol kappa, human pol eta, Sso Dpo4, Sac Dbh, Sce pol zeta, and human pol iota.

Examples of an endonuclease for use in the reaction mixture may include at least one of: at least one endonuclease from any of Phage T4, *E. coli*, human and *Thermus* species. The reaction mixture may further include one or more enzymes selected from the following: T4 pyrimidine dimer glycosylase, [fapy]-DNA glycosylase (Fpg), UvrA, UvrB, UvrC, UvrD, Cho, Endo V, Endo III, Endo VIII, UDG, lambda beta protein, RecA and Aag.

In an embodiment of the invention, improved yield is achieved after copying the polynucleotide by means selected from the group consisting of: PCR amplification, helicase-dependent amplification, transcription-mediated amplification, strand-displacement amplification, rolling circle amplification and whole genome amplification. Where the polynucleotide is an RNA, the amplification may be RT-amplification. Where the polynucleotide is DNA, the reaction mixture may comprise 1-100 units of *E. coli* Endo IV, 0.05-0.25 units of *E. coli* PolI and 5-500 units of Taq ligase added to 1-1000 ng DNA in a reaction volume of 10-1000 µL.

Improved or enhanced yield is determined where less than about 50% of the concentration of the starting polynucleotide preparation provides at least a similar amount of copied product obtainable absent the reaction mixture. Preferably, the improvement should be reproducible meaning that about 75% or more of replicate samples will demonstrate the improvement. Moreover, optionally, an additional feature of the method is that it is capable of achieving an improved result at a single temperature of incubation.

In an embodiment of the invention, a method is provided where amplification of the polynucleotide is capable of producing an amplicon in a size range of 50 nucleotides to 100,000 nucleotides in a polymerase chain reaction.

In an embodiment of the invention, a kit is provided that includes one or more enzymes wherein at least one of the enzymes is a ligase, the one or more enzyme being formulated for addition to a polynucleotide preparation to enhance (as described above) copying of the polynucleotide and instructions for their use.

In an embodiment of the invention, a composition is provided that includes an effective amount of a ligase, a polymerase, and an AP endonuclease, not including Endo VI, for providing enhancement of at least one of yield and fidelity of a copied polynucleotide compared with a copied polynucleotide in the absence of the composition. In an example of the composition, the concentration of certain enzymes is as follows: 1-100 units of AP endonuclease, 0.05-5 units of the polymerase, and 5-500 units of the ligase in a volume 10-1000 µL for use in a pre-amplification mixture.

Examples of particular enzymes in the composition include an AP endonuclease, more particularly Type II AP endonuclease, more particularly, *E. coli* Endo IV. The polymerase is exemplified by *E. coli* polI. In addition, at least one of the following enzymes may be further included in the composition: T4 pyrimidine dimer glycosylase, [fapy]-DNA glycosylase (Fpg), UvrA, UvrB, UvrC, UvrD, Cho, Endo V, Endo III, Endo VIII, UDG, RecA, lambda beta protein and Aag.

In an embodiment of the invention, a method is provide for enhancing the yield of a copied or amplified polynucleotide, which includes: (a) obtaining at least a first pair and a second pair of primers wherein the second pair of primers is nested within the first set of primers when hybridized to the polynucleotide; (b) subjecting the polynucleotide to a composition described above; (c) amplifying the polynucleotide with the first set of primers; (d) amplifying the product of (c) with the second set of primers; and (e) obtaining an enhanced yield of amplified polynucleotide.

In an additional embodiment of the invention, a method is provided for cloning a polynucleotide fragment that includes: repairing sequence errors in the polynucleotide fragment by means of a composition such as described above. This composition may have the advantageous property of blunt-ending the polynucleotide fragment, which eliminates a step in cloning a fragment into a vector.

In an additional embodiment of the invention, a method is provided for sequencing a polynucleotide, which includes contacting the polynucleotide with the composition described above prior to sequencing. The quality of the sequence results is generally improved with respect to sensitivity and to accuracy.

In an additional embodiment of the invention, a method for copying or amplifying a fragmented DNA is provided which involves (a) contacting the fragmented DNA with the composition above; (b) optionally adding a recombination competent protein; and c) amplifying or copying the fragmented DNA. Examples of recombination competent proteins are RecA and beta protein from, for example, lambda phage.

BRIEF DESCRIPTION OF THE DRAWINGS

FIG. 1A shows DNA template damaged to differing extents by heat and the effect of this damage on amplification of a 5 kb segment of lambda DNA where 5 ng, 2 ng and 1 ng of heat-treated lambda DNA were amplified after prior damage by 99° C. heat treatment for 0 sec, 30 sec, 60 sec, 90 sec, 120 sec or 180 sec. The damaged DNA was not subjected to enzyme treatment prior to amplification. The amount of amplification was determined after electrophoresis and was found to be substantially reduced by 120 sec heat treatment. The first lane on the gel contains 1 µg of a 2-log ladder size standard (NEB#N3200, New England Biolabs, Inc., Ipswich, Mass.).

FIG. 1B shows enhanced amplicon yields from heat-damaged lambda DNA using Taq ligase, *E. coli* Endo IV and *E. coli* PolI on amplification of a 5 kb segment of lambda DNA. DNA was heat damaged as described in FIG. 1A but the damaged DNA was subjected to enzyme treatment prior to amplification. The results of amplification are shown after a 10-minute pretreatment reaction with Taq ligase, *E. coli* Endo IV and *E. coli* PolI. The amplicon yield was increased throughout but was especially noticeable with 120 sec and 180 sec heat damaged DNA. First and last lanes on the gel contain 1 µg of a 2-log ladder size standard (NEB#N3200, New England Biolabs, Inc., Ipswich, Mass.

FIG. 1C shows enhanced amplicon yields from heat-damaged lambda DNA using Taq ligase, Tth Endo IV and *E. coli* PolI. The amplification was performed according to FIG. 1B but the enzyme treatment prior to amplification contained *Thermus thermophilus* (Tth) Endo IV in place of *E. coli* Endo IV. The results of amplification are shown after a 10-minute pretreatment reaction with *Thermus aquaticus* (Taq) ligase, Tth Endo IV and *E. coli* PolI. The amplicon yield was increased throughout but was especially noticeable with 120 sec and 180 sec heat-damaged DNA. Only the first lane contains the molecular weight marker ladder.

FIG. 1D shows enhanced amplicon yields from heat-damaged lambda DNA using *E. coli* ligase, *E. coli* Endo IV and *E. coli* DNA polI. The amplification was performed according to FIG. 1B but the enzyme treatment prior to amplification contained *E. coli* ligase in place of Taq ligase. The lambda DNA subjected to 99° C. for 180 sec was used as a template. The amount of template DNA used is indicated above each lane. The yield of 5 kb amplicon is enhanced for each of the template amounts by enzyme pretreatment.

FIG. 2A shows the results of amplification of a 5 kb segment of lambda DNA where lambda DNA was heated to 70° C. in citrate buffer pH 5 for 0, 20, 40, 80, 120, and 160 minutes. 50 ng, 10 ng and 5 ng of each citrate treated sample were amplified and the resulting products were visualized on a gel to determine the extent of amplification. The DNA was not treated with selected enzymes prior to amplification. The last lane on the right contains 1 µg of 2-log ladder.

FIG. 2B shows the increase in yield of a 5 kb amplicon of lambda DNA regardless of which polymerase was used in the enzyme mixture. 120-minute citrate-damaged lambda DNA was treated with various enzymes prior to amplification.

Lane 1: 1 µg 2-log ladder (NEB# N3200, New England Biolabs, Inc., Ipswich, Mass.).

Lane 2: no pretreatment.

Lane 3: Pretreatment with Taq ligase, Taq DNA polymerase and E. coli Endo IV.

Lane 4: Pretreatment with Taq ligase, E. coli PolI, and E. coli Endo IV.

Lane 5: Pretreatment with Taq ligase, Taq:Vent® DNA polymerase mix, and E. coli Endo IV.

Figure 3:
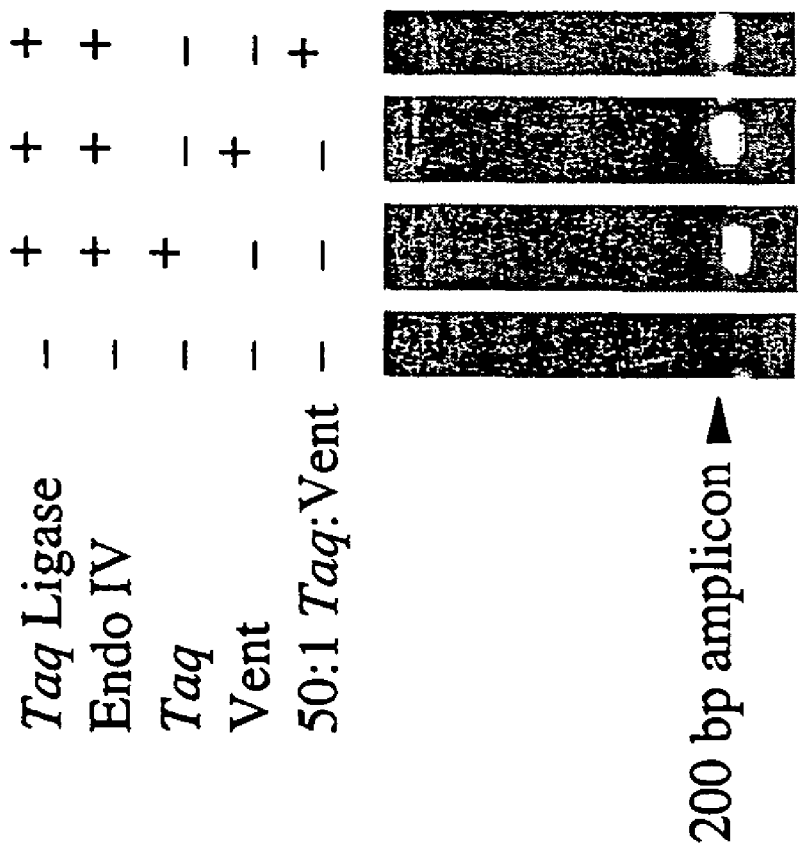

FIG. 3 shows the results of amplification of a 200 bp segment of krill genome that has been extracted from an ethanol stored sample of krill and pretreated with an enzyme mixture containing one of various polymerases, a ligase and an AP endonuclease that enhances amplification yields.

Lane 1: No pretreatment of krill DNA with enzymes.

Lane 2: Pretreatment of krill DNA with Taq ligase, E. coli Endo IV, and Taq polymerase.

Lane 3: Pretreatment of krill DNA with Taq ligase, E. coli Endo IV, and Vent® polymerase.

Lane 4: Pretreatment of krill DNA with Taq ligase, E. coli Endo IV, and 50:1 Taq:Vent® polymerase.

Figure 4:
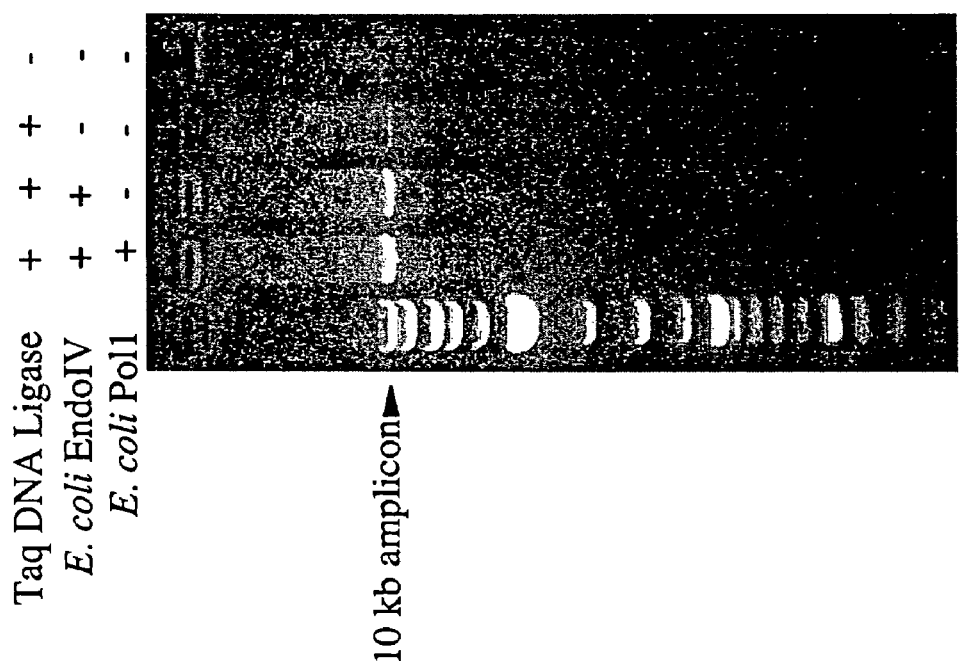

FIG. 4 shows an increase in yield of a 10 kb amplicon from heat-damaged DNA. 180 sec heat-damaged DNA was pre-treated with an enzyme mixture and then amplified.

Lane 1: 1 µg of a 2-log ladder size standard (NEB#N3200, New England Biolabs, Inc., Ipswich, Mass.).

Lane 2: Pre-treatment with Taq ligase, E. coli Endo IV, and E. coli PolI.

Lane 3: Pre-treatment with Taq ligase and E. coli Endo IV.

Lane 4: Pretreatment with Taq ligase.

Lane 5: Control—untreated DNA.

Figure 5:
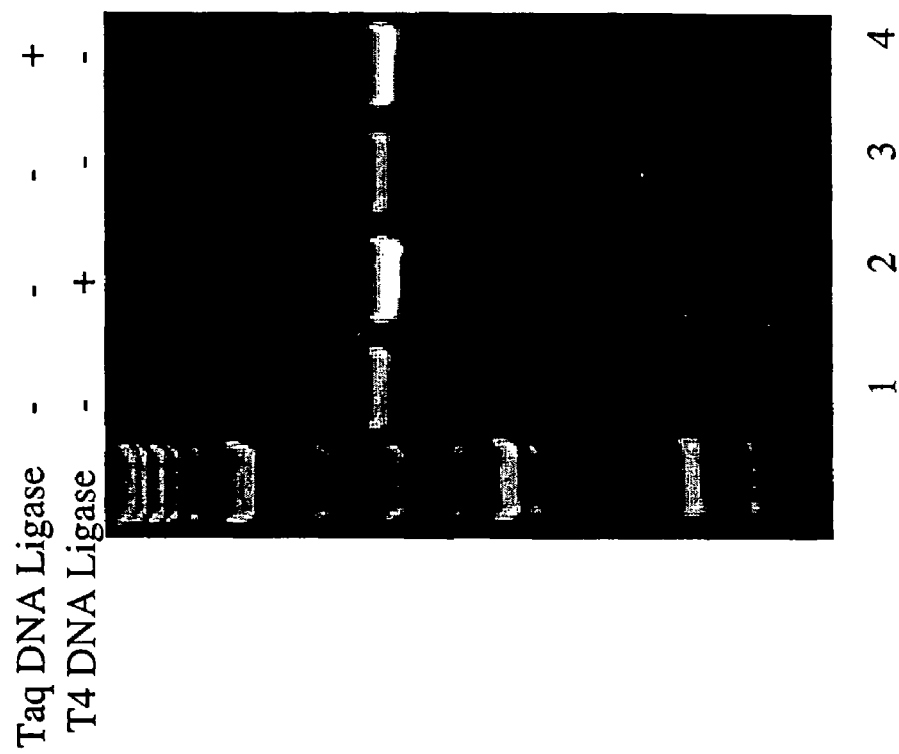

FIG. 5 shows that ligase pretreatment increases amplicon yield from environmental DNA (soil sample extract).

Lane 1: A 2-log ladder size standard (NEB# N3200, New England Biolabs, Inc., Ipswich, Mass.).

Lane 1: No enzyme pretreatment.

Lane 2: Pre-treatment with T4 ligase.

Lane 3: No enzyme pre-treatment.

Lane 4: Pretreatment with Taq ligase.

FIGS. 6A-1-6A-9 and 6B-1-6B-2: Blast P search at NCBI using E. coli DNA ligase (A) and T4 DNA ligase (B).

FIG. 7: DNA sequence of Tth Endo IV (SEQ ID NO:11).

FIGS. 8A, 8B and 8C show the effect of UV light on amplicon yield using lambda DNA.

FIG. 8A: Lambda DNA is subjected to UV irradiation for up to 50 sec and a slight reduction in yield of a 2 kb amplicon produced is shown.

FIG. 8B: Lambda DNA is subjected to UV irradiation for up to 50 seconds and the reduction in yield of a 5 kb amplicon is shown.

FIG. 8C: The effect of various reaction mixtures added to lambda DNA on yield of a 5 kb amplicon after UV irradiation is shown.

Lanes 2-7 are controls in the absence of a reaction mixture.

Lanes 8-13 show the increased beneficial effect of adding ligase, polymerase and AP endonuclease plus 10 units of T4 pdg.

Lanes 14-19 show the increased beneficial effect of adding ligase, polymerase and AP endonuclease plus 80 units of T4 pdg.

Lanes 1 and 20: A 2-log ladder size standard (NEB#N3200, New England Biolabs, Inc., Ipswich, Mass.).

FIGS. 9A and 9B show that adding ligase to T7 Endo I expands the useful range of the EndoI:DNA ratio in which the product is not degraded. Taq ligase and T7 Endo I were added to supercoiled DNA in varying amounts as indicated for each lane.

FIG. 9A is the control in which no Taq ligase has been added but increasing amounts of T7 Endo I are used. The supercoiled DNA is predominantly cleaved into fragments of various sizes with 12.5-25 units of T7 Endo I.

FIG. 9B shows how the addition of 100 units of Taq ligase protects DNA from non-specific cleavage in the presence of T7 Endo I such that even at 200 units of T7 Endo I, there is a clear band corresponding to linear DNA not present in the absence of ligase.

FIGS. 10A and 10B show the effect of repair enzyme treatment on amplicon yield from oxidatively damaged DNA or undamaged template.

FIG. 10A shows that the addition of repair enzymes to an undamaged template, pWB407 has no effect on amplicon yield.

FIG. 10B shows that the addition of Fpg to a damaged template, plasmid pWB407, which was previously incubated in the presence of methylene blue, gives inconsistent effects on yield. The addition of Taq ligase, E. coli DNA polymerase, and E. coli Endo IV in the presence or absence of Fpg consistently increases amplicon yield.

Figure 11:
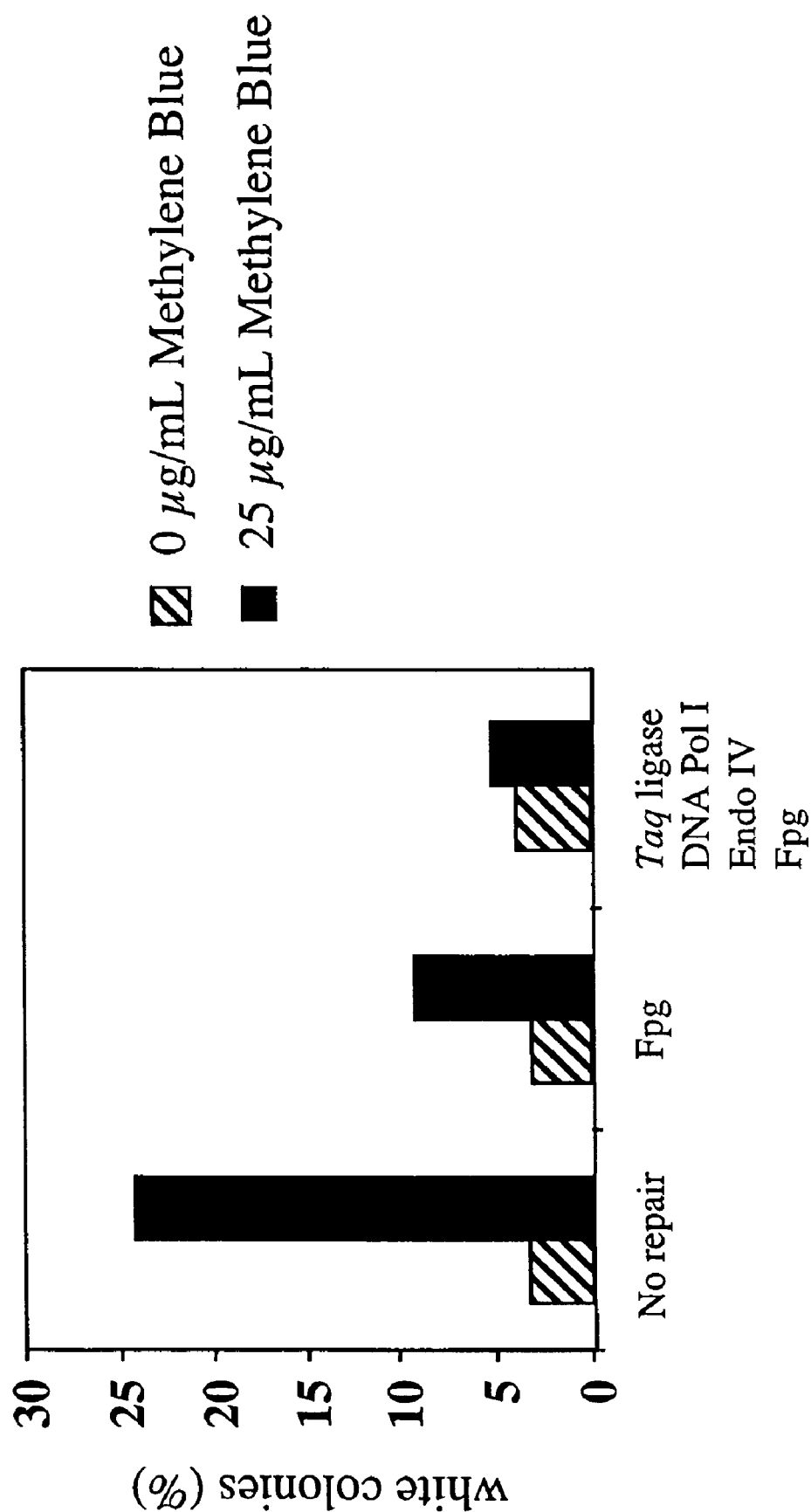

FIG. 11 shows increased PCR reaction fidelity from damaged DNA after treatment with repair enzymes. Repair enzyme treatment of undamaged template, plasmid pWB407, prior to PCR has no significant effect on fidelity. Treatment of a damaged template, plasmid pWB407 incubated with methylene blue, with Fpg alone or also with Taq ligase, E. coli DNA polymerase I, and E. coli endonuclease increases the fidelity of PCR. The measure of fidelity is the number of white colonies verses the number of blue colonies after cloning a lacZ-containing amplicon as discussed below. The higher the percentage of white colonies the greater the error rate.

Figure 12:
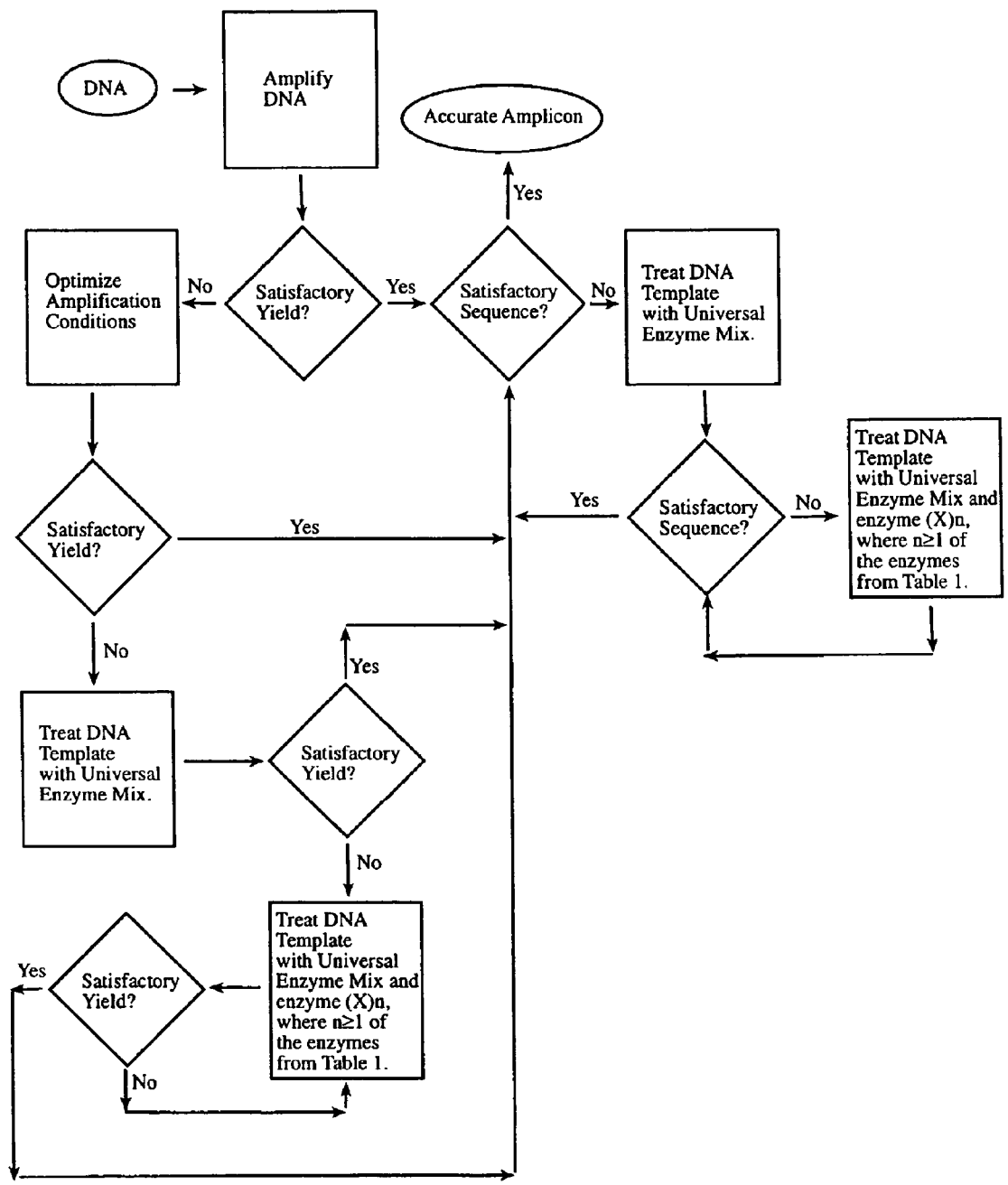

FIG. 12 shows a flow diagram for treating damaged DNA or to increase at least of one of fidelity or yield.

Figure 13A:
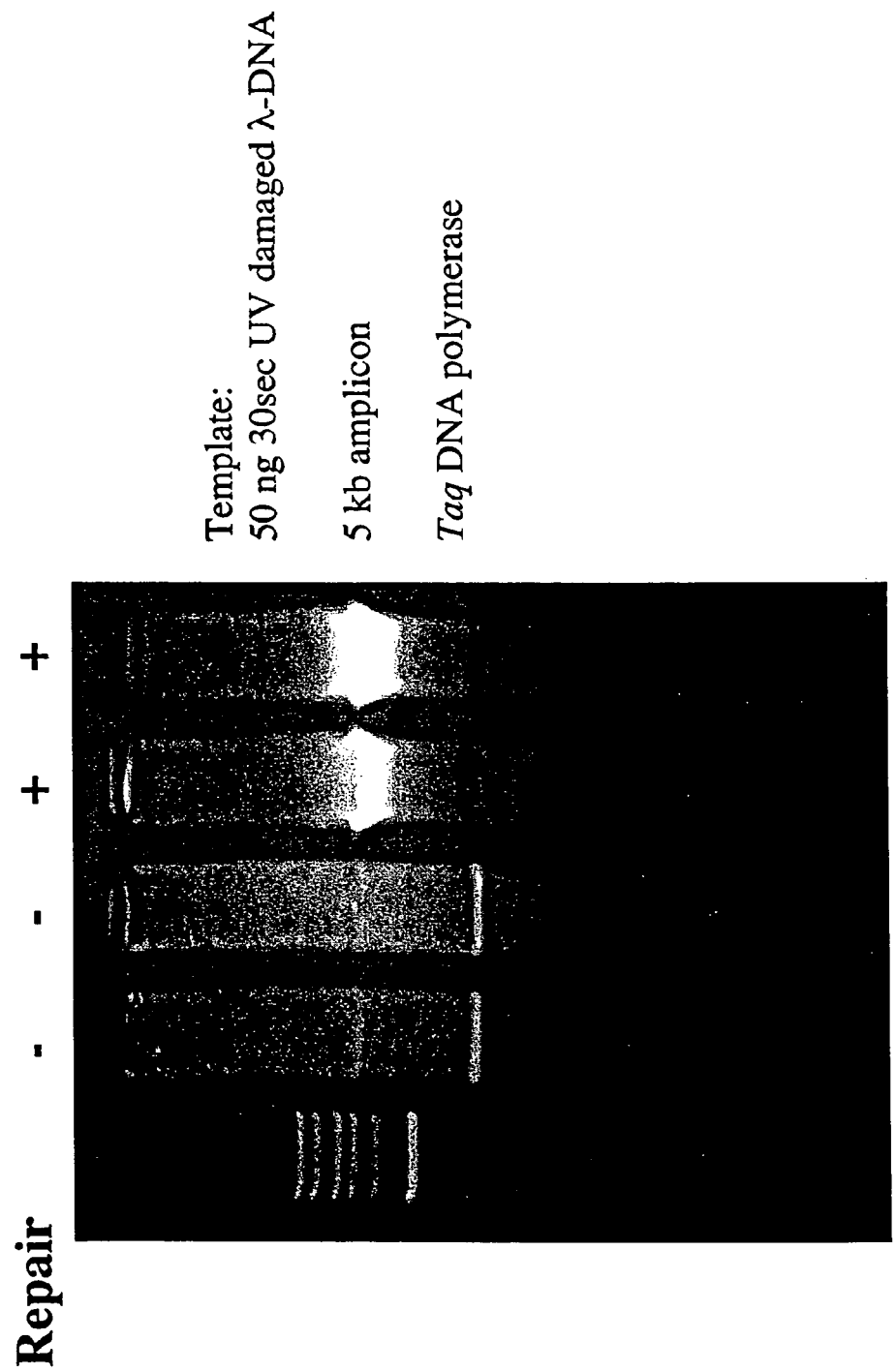
Figure 13B:
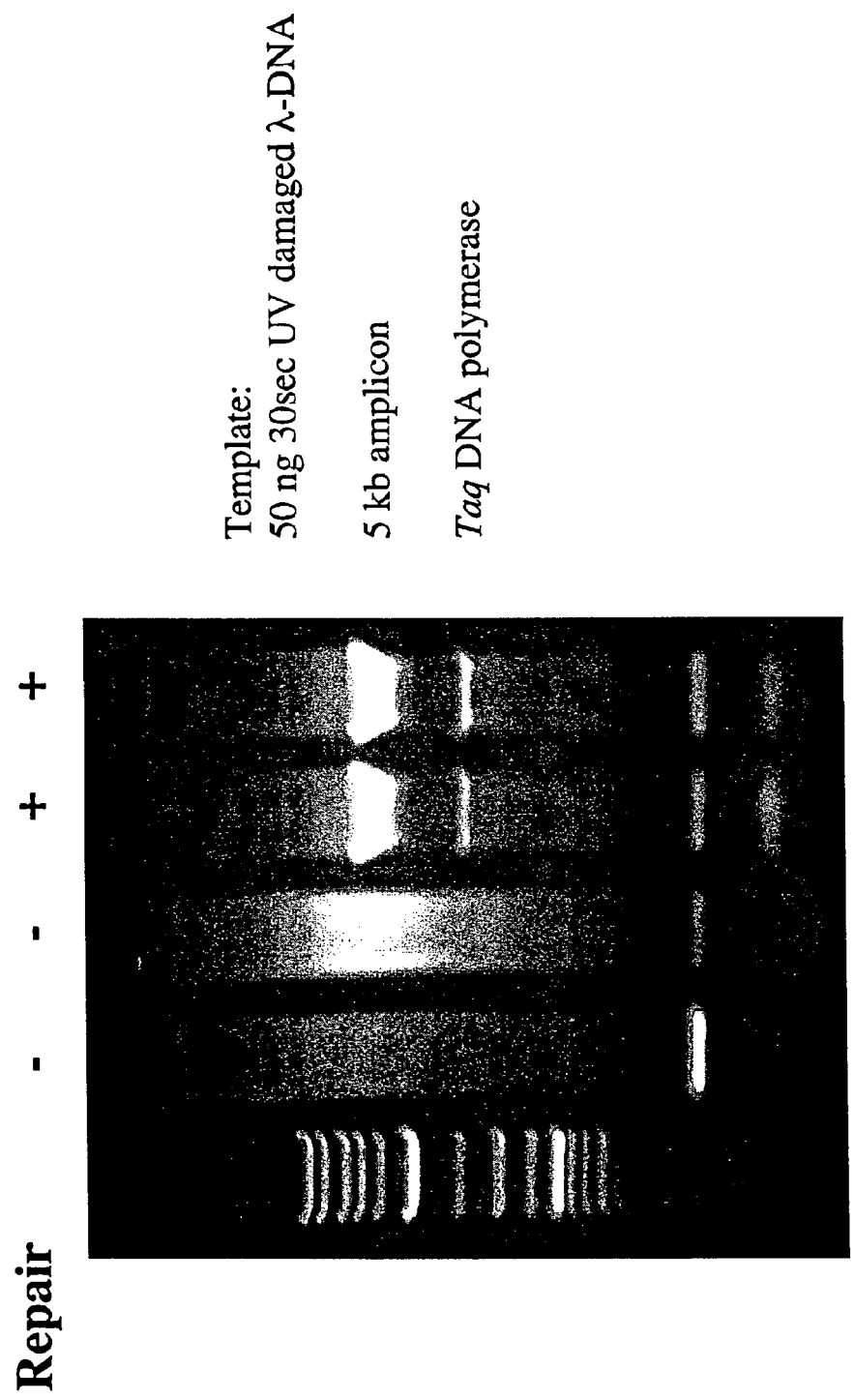

FIGS. 13A and 13B show how yield of amplicon is increased for a 5 kb fragment of 30 s UV damaged DNA incubated for 15 minutes at room temperature or at 4° C. overnight with a multi-enzyme repair mix.

FIG. 13A: Room temperature incubation:

Lane 1: 2-log ladder DNA molecular weight standard.

Lanes 2 and 3: the two reactions incubated without the multi-enzyme repair mix at room temperature for 15 minutes.

Lanes 4 and 5: the reactions incubated with the repair mix at room temperature for 15 minutes have the expected 5 kb amplicon.

FIG. 13B: 4° C. incubation:

Lane 1: 2-log ladder DNA molecular weight standard.

Lanes 2 and 3: the two reactions incubated without the multi-enzyme repair mix overnight at 4° C.

Lanes 4 and 5: the reactions incubated with the repair mix overnight at 4° C. have the expected 5 kb amplicon.

Figure 14:
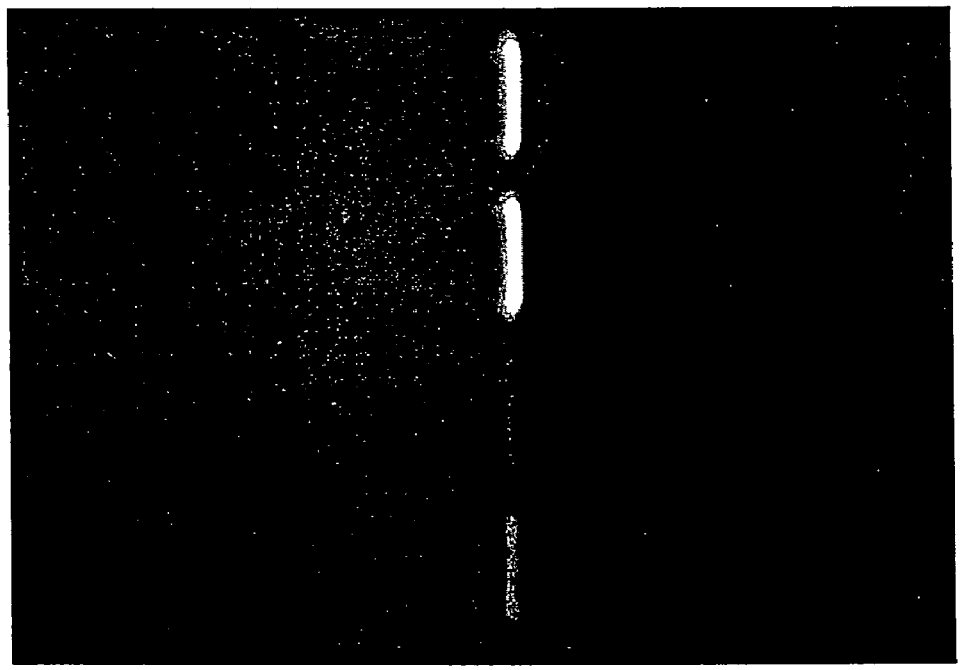

FIG. 14 shows enhanced amplicon yield from a uracil-containing plasmid after treatment with a repair enzyme mix for 15 mins at room temperature and PCR amplification using an archaeal polymerase. Lanes 1 and 2 shows the product of PCR amplification of pNEB0.92U using vent DNA polymerase. There is a weakly visible band at 920 bp. Lanes 3 and 4 show the product of PCR amplification from pNEB0.92U treated with a repair enzyme mix.

Figure 15:
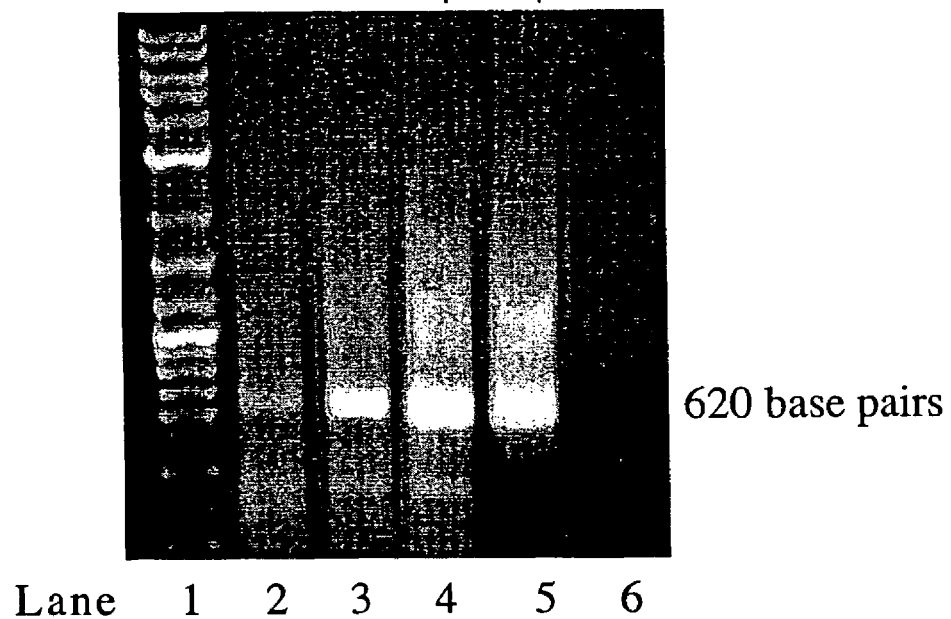

FIG. 15 shows an agarose gel on which a band corresponding to an amplified DNA of 620 base pairs is identified. The 620 bp amplicon was obtained from 20 overlapping single strand oligonucleotides of 48 nucleotides or smaller.

Lane 1: 2-log DNA molecular weight standards (NEB#N3200S, New England Biolabs, Inc., Ipswich, Mass.).

Lane 2: 20 oligonucleotides incubated with 400 units Taq DNA ligase, 0.1 units *E. coli* PolI, 5 units T4 pdg, and 20 units EndoIV during the assembly step.

Lane 3: 20 oligonucleotides incubated with 400 units Taq DNA ligase, 0.1 units *E. coli* PolI, 5 units T4 pdg, 20 units Endo IV, and lambda beta protein during the assembly step.

Lane 4: 20 oligonucleotides incubated with 400 units Taq DNA ligase, 0.1 units *E. coli* PolI, 5 units T4 pdg, 20 units Endo IV, and *E. coli* RecA during the assembly step.

Lane 5: 20 oligonucleotides incubated with 400 units Taq DNA ligase, 0.1 units *E. coli* PolI, 5 units T4 pdg, 20 units Endo IV, lambda beta protein and RecA during the assembly step.

Lane 6: the control, 20 oligonucleotides with no added repair enzymes during the assembly step.

Figure 16:
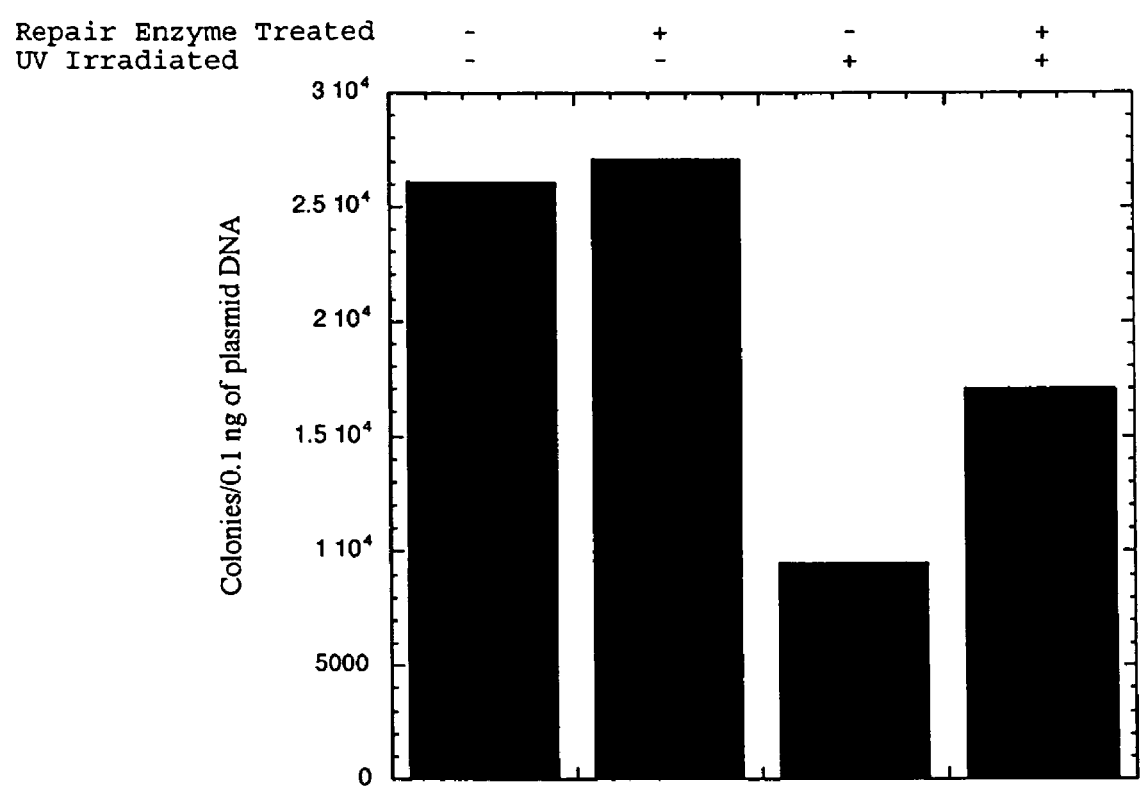

FIG. 16 shows the effect of DNA repair treatment on non-irradiated (−) and irradiated DNA (+) as determined by the number of colonies obtained when the DNA containing a selection marker is used to transform cells.

Figure 17:
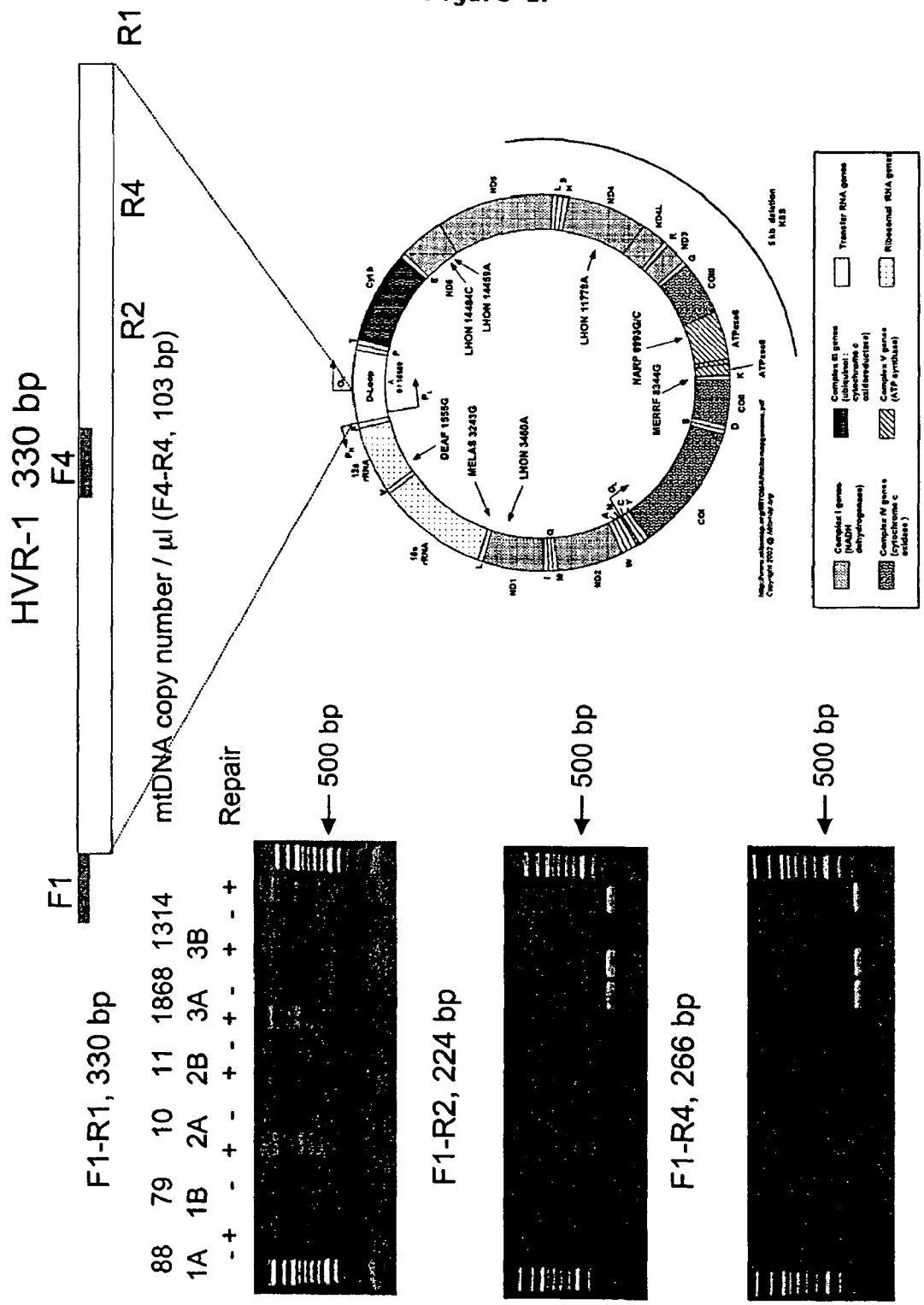

FIG. 17 shows improved yields of amplicon from ancient cave bear DNA after 2 sets of amplification reactions using different nested primer pairs. The gene map shows the location of primer pairs F1-R1, F1-R2 and F1-R4. Above the gels, a set of numbers is provided (88, 79, 10, 11, 1868 and 1314) that represent the estimated amount of mitochondrial DNA in each sample. Lanes 3A and 3B contain the most DNA. +/− indicates whether a repair mix was used prior to the first amplification using F1-R1. In Lane 3B, a sharp band corresponding to repaired cave bear DNA was observed that was not present in the absence of repair.

FIG. 18 shows the DNA sequence for plasmid pNEB0.92U (SEQ ID NO:42).

DETAILED DESCRIPTION OF EMBODIMENTS

Embodiments of the invention provide improvements in the method for copying or more specifically amplifying polynucleotides. Enhancing at least one of yield and fidelity of copied or amplified polynucleotides is associated with obtaining a detectable yield of polynucleotides after copying or amplification of 50% of the polynucleotides needed in the absence of a reaction mixture containing selected repair enzymes as exemplified in present embodiments. 'Fidelity' relates to copying in which the error rate is less than would otherwise be the case in the absence of a reaction mixture containing selected repair enzymes as exemplified in present embodiments.

The inventive method utilizes a reaction mixture containing enzymes. If multiple types of damage are suspected, then a combination of enzymes can be constructed as illustrated by the specific cocktails used in the examples. If the damage to the polynucleotide is known, then a preferred cocktail of enzymes may be selected as illustrated in the examples. If the nature of the damage is unrecognized, a universal mixture of enzymes can be employed. In general, adding enzymes together in one step does not preclude adding enzymes sequentially.

Where polynucleotide copying leads to polymerase-dependent amplification, short amplicons that are less than about 500 bases in length (as short as 100 base pairs) or long amplicons that are greater than 500 bases or as much as about 50 kb may be amplified (for PCR, RT-PCR and qPCR amplification). Other types of amplification can produce amplicons having a wide range of sizes. For example, polynucleotides having a size as small as 100 bases or as large as a whole genome (3 billion bases for humans). Examples of such amplification methodologies include: whole genome amplification, rolling circle amplification (RCA) and helicase-dependent amplification (HDA). Other types of polynucleotide synthesis include primer extension reactions such as sequencing reactions. Embodiments of the methods have wide utility in molecular biology research and in solving problems in applied biology, including for example, analyzing fragmented and damaged DNA such as found in forensic analysis, in biological archeology in which it is desirable to analyze DNA from ancient sources, for taxonomy where it is desirable to analyze DNA from environmental samples such as required for the Barcode of Life Project, and for diagnostic assays including tissue biopsies to determine a disease susceptibility or status. Other uses include: high-fidelity sequencing, gene assembly, fragment analysis and one step copying and ligation for cloning.

Source and Extent of Damage

Most polynucleotides that are isolated or in vitro replicated polynucleotides are damaged to some extent. Damage of a polynucleotide may result from chemical modification of individual nucleotides or disruption of the polynucleotide backbone. Polynucleotides experience damage from diverse sources such as chemicals including formaldehyde and ethanol, environmental factors, temperature extremes, oxidation, dessication and ultra violet light. Various types of damage include: (a) apurinic or apyrimidinic damage caused for example by heat, storage of polynucleotides in ethanol, and exposure to factors in the environment such as $H_2O$ or extremes of pH; (b) modification of individual nucleotides, caused for example by deamination, alkylation, and oxidation; (c) nicks and gaps caused for example by heat, storage of polynucleotide in ethanol, and exposure to factors in the environment such as $H_2O$ or extremes of pH; (d) cross-linking caused for example, by formaldehyde, light or environmental factors; (e) mismatched DNA caused by for example misincorporation of a nucleotide by a polymerase; and (f) fragmentation of DNA.

Damage is more severe in preserved tissues, dried specimens or polynucleotides that are exposed to the environment. Damage can occur as a result of the age of the sample or its source or its preparation. In addition, damage can occur during the application of a methodology for polynucleotide synthesis such as occurs during PCR amplification, which involves a high temperature step. Hence most polynucleotides are damaged to some extent. This damage has a greater influence when longer amplicons are analyzed since the likelihood of encountering damage during amplification is increased.

Polynucleotides can sustain damage in a variety of ways. Different polynucleotide preparations experience different types of damage depending upon, for example, the storage or handling of the polynucleotide preparation in vitro, how prokaryotic cells, archaea or eukaryotic cells containing the polynucleotides are stored and the characteristics of the cells from which the polynucleotides are extracted. Synthetic polynucleotides can sustain damage during chemical synthesis.

The term "polynucleotide" refers in particular to double-stranded DNA, double-stranded RNA, hybrid DNA/RNA duplex, single-stranded DNA and single-stranded RNA.

A "repair enzyme" refers in particular to a psychrophilic, mesophilic or thermophilic enzyme that participates in the process of repair of a polynucleotide. For example, a repair enzyme may induce breakage of the polynucleotide at a bond, thereby facilitating removal of damaged regions of the polynucleotide or removal of single nucleotides. Enzymes with a synthetic role such as ligases and polymerases are also repair enzymes. In embodiments of the invention, one or more selected repair enzymes are provided in a reaction mixture. The damaged DNA is subjected to the reaction mixture so as to enhance copying and/or amplification of DNA. "Enhancing" refers to obtaining an improved ratio of copied or amplified product to starting material compared to the ratio observed in the absence of the repair mixture.

DNA repair enzymes are described in the scientific literature, for example, see Wood, R. D., et al. *Mutat. Res.* 577(1-2):275-83 (2005) and Eisen, J. A. and Hanawalt, P. C. *Mutat. Res.* 435(3):171-213 (1999). A list of human repair enzymes is provided in Table 1 below. Although not described in Table 1, the homologs of the listed enzymes and other functionally related enzymes are included in the description of repair enzymes. Any of the above enzymes may be naturally occurring, recombinant or synthetic. Any of the enzymes may be a native or in vitro-created chimeric protein with several activities. The methods of searching the databases to identify related enzymes that share conserved sequence motifs and have similar enzyme activity are known to a person of ordinary skill in the art. For example, the NCBI web site (www.ncbi.com) provides a conserved domain database. If, for example, the database is searched for homologs of Endo IV, 74 sequence matches are recovered. (Also see FIGS. 6A-1-6A-9 and 6B-1-6B-2 for ligases.)

A "polynucleotide cleavage enzyme" used in enzyme mixtures for repairing damaged DNA refers in particular to a class of repair enzymes and includes AP endonucleases, glycosylases and lyases responsible for base excision repair.

A damaged base can be removed by a DNA glycosylase enzyme which hydrolyses an N-glycosylic bond between the deoxyribose sugar moiety and the base. For example, an *E. coli* glycosylase, UDG endonuclease, repairs deaminated cytosine while two 3-mAde glycosylases from *E. coli* (TagI and TagII) repair damage from alkylating agents.

The product of removal of a damaged base by a glycosylase is an apurinic or apyrimidinic site (AP site) that must be correctly replaced. This can be achieved by an endonuclease, which nicks the sugar phosphate backbone adjacent to the AP site. The abasic sugar is removed and a new nucleotide is inserted by polymerase/ligase activity. These repair enzymes are found in prokaryotic and eukaryotic cells. Some enzymes having applicability herein have glycosylase and AP endonuclease activity in one molecule. Abasic sites can be recognized and cleaved by AP endonucleases and/or AP lyases. Class II AP endonucleases cleave at AP sites to leave a 3' OH that can be used in polynucleotide polymerization. Furthermore, AP endonucleases can remove moieties attached to the 3' OH that inhibit polynucleotide polymerization. For example a 3' phosphate can be converted to a 3' OH by *E. coli* Endo IV. AP endonucleases can work in conjunction with glycosylases.

Examples of glycosylase substrates include Uracil, Hypoxanthine, 3-methyladenine (3-mAde), Formamidopyrimidine, 7,8 dihydro-8-oxyguanine and Hydroxymethyluracil. The presence of uracil in DNA may occur due to misincorporation or deamination of cytosine by bisulfate, nitrous acids, or spontaneous deamination. Hypoxanthine generally occurs due to deamination of adenine by nitrous acids or spontaneous deamination. In this context, 3-mAde is a product of alkylating agents. Formamidopyrimidine (FAPY) (7-mGua) is a common product of methylating agents of DNA. 7,8-dihydro-8 oxoguanine is a mutagenic oxidation product of guanine. Gamma radiation produces 4,6-diamino-5-FAPY. Hydroxymethyuracil is created by ionizing radiation or oxidative damage to thymidine.

These different types of damage may be repaired using glycosylases of the sort described above and in Table 1.

Another type of repair enzyme is a lyase. This enzyme can break the phosphodiester bond in a polynucleotide.

Examples of AP endonucleases belong to 4 classes.
(I) cleaves 3'→3'-OH+5'-P—and has associated glycosylase activity.
(II) cleaves 5'→3'-OH+5'-P
(III) cleaves 3'→3'-P+5'-OH
(IV) cleaves 5'→3'-P+5'-OH Several enzymes have been isolated that appear to have AP endonuclease or lyase and glycosylase activities that are coordinated either in a concerted manner or sequentially.

Examples of polynucleotide cleavage enzymes now found to be suitable for use in enhancing at least one of yield or fidelity in a copying or amplification reaction include the following types of enzymes derived from but not limited to any particular organism or virus: 1) AP endonucleases, such as *E. coli* Endo IV, Tth Endo IV, and human AP endonuclease; 2) glycosylases, such as UDG, *E. coli* AlkA and human Aag; 3) glycosylase/lyases, such as *E. coli* Endo III, *E. coli* Endo VIII, *E. coli* Fpg, human OGG1, and T4 pyrimidine dimer glycosylase (T4 pdg); and 4) lyases such as *E. coli* Endo V.

Endo VI (also termed Exo III) is known to be capable of degrading a substantial portion of a polynucleotide outside the damaged regions of interest in a polynucleotide in a few hours under normal reaction conditions, hence is not to be included in the present enzyme mixtures for treating damaged polynucleotides.

A "polymerase" for present purposes refers to an enzyme that has polymerase activity even though it may have other activities. The same polymerase or polymerases may be used throughout the repair and copying reactions or different polymerases may be employed at different stages of the present methods.

Examples of polymerases include thermostable bacterial polymerases such as Taq DNA and *Thermus thermophilus* polymerases and archeal polymerases such as Vent®, Deep Vent® and Pfu; less thermostable enzymes such as Bst polymerase, *thermomicrobium roseum* polymerases and mesophilic polymerases such as phage polymerases (such as phi29 polymerase, T7 polymerase and T4 polymerase), *E. coli* polI and *E. coli* polIII Y family polymerases such as *E. coli* pol IV, *E. coli* pol V, human pol kappa, human pol eta, Sso Dpo 4, Sac Dbh, Sce pol zeta, human pol iota (MacDonald et al. *Nucleic Acids Res.* 34:1102-1111 (2006); Vaisman et al. *DNA Repair* 5:210 (2006); Ohmori et al. *Mol. Cell.* 8:7-8 (2001); Goodman *Ann. Rev. Biochem.* 71:17-50 (2002)) or mutants, derivatives or modifications therefrom. Examples of derivatives include Phusion™ enzyme (Finnzymes, Espoo, Finland) and other polymerases that combine a double strand binding protein with polymerase sequences from one or several sources.

A "ligase" as used in the enzyme mixtures described here refers to an enzyme that joins a 5' end of a single strand of a polynucleotide to a 3' end of another single strand of a polynucleotide. Such ligases are found in substantially all eukaryotic, prokaryotic, and archaeal cells, and can also be found in some bacteriophages and viruses. Examples of suitable ligases include 9° N ligase, *E. coli* ligase, T4 ligase and Taq ligase. Other ligases include LIGA (NP-416906.1), TthDNALGS (AAA27486.1), LIG3 (NM-013975) and LIG4 (NM-002312).

Other ligases or ligase-like proteins that may have utility herein are revealed by a Blast search using T4 ligase or *E. coli* ligase to search the database (see FIGS. 6A-1-6A-9 and FIGS. 6B-1 and 6B-2) in which any enzyme sharing at least 6 contiguous amino acids with these known ligases may be included in a repair mixture according to embodiments of the invention.

Contrary to a published use of ligase in combination with Exo III in the absence of any cofactors (U.S. Publication No. 2005-0026147), it has been found here that NAD$^+$ or ATP is required in enzyme mixtures that include ligase. More specifically, Taq ligase and E. coli ligase require NAD$^+$ while T4 ligase and 9° N ligase require ATP.

Certain ligases, polymerases and endonucleases are available from New England Biolabs Inc., Ipswich, Mass. where pages 107-117 of the 2005-2006 catalog are incorporated by reference (pp. 102-108 for ligases) and described in U.S. Provisional Application No. 60/717,296 and International Publication No. WO 2005/052124. In addition, thermostable repair enzymes can be used interchangeably with thermolabile repair enzymes in a preamplification mixture. Thermostable enzymes retain activity at above 40° C. or more particularly 65° C. or above.

Embodiments of present methods improve the yield or fidelity of products resulting from copying polynucleotide sequences, amplification or other synthesis reaction. This can be achieved, for example, when a damaged polynucleotide is treated with a preparation of enzyme(s) in a pre-incubation mixture and/or during amplification.

Amplification protocols that may benefit from the above described pre-incubation include polymerase chain reaction (PCR), Strand-Displacement Amplification (SDA) (U.S. Pat. Nos. 5,455,166 and 5,470,723); Helicase-Dependent Amplification (HAD) (U.S. Publication No. 2004-0058378-A1); Transcription-Mediated Amplification (TMA) (Guatelli et al., *Proc. Natl. Acad. Sci. USA* 87:1874-1878 (1990)); Rolling Circle Amplification (RCA) which generates multiple copies of a sequence for the use in in vitro DNA amplification adapted from in vivo rolling circle DNA replication (see, for example, Fire and Xu, *Proc. Natl. Acad. Sci. USA* 92:4641-4645 (1995); Lui, et al., *J. Am. Chem. Soc.* 118:1587-1594 (1996); Lizardi, et al., *Nature Genetics* 19:225-232 (1998)); and whole genome amplification methods. (Hawkins et al. *Current Opinions in Biotechnology* 13:65-67 (2002)).

A "universal" enzyme mixture has now been found to be useful in a reaction mixture for generally repairing damaged polynucleotides prior to or during copying or amplification. In accordance with the present embodiments, there are also specific advantageous combinations in given situations.

The universal enzyme mixture contains a ligase and a cofactor such as NAD$^+$ or ATP. The mixture preferably additionally includes a polymerase and an AP endonuclease as described above within a suitable buffer such as Thermopol (New England Biolabs, Inc., Ipswich, Mass.), AccuTaq LA DNA polymerase buffer (Takara Bio Inc., Shiga, Japan) or any other conventional Taq buffer. In various illustrative embodiments, the universal enzyme mixture contains E. coli PolI or Taq polymerase and an AP endonuclease such as a mesophilic Endo IV, e.g., E. coli Endo IV or a thermophilic Endo IV, e.g., Tth Endo IV and a ligase selected from E. coli ligase, Taq ligase or an archaeal ligase such as 9° N ligase. In a particular embodiment, the enzyme mixture contains 1-100 units Endo IV, 0.05-0.25 units E. coli PolI, and 5-500 units of a Taq DNA ligase suitable for repairing 1-1000 ng DNA in a reaction volume of 10-1000 μL prior to or during amplification. It will be understood that the concentration range for endonucleases and polymerases other than those specified in the universal mixture above may vary with the enzyme used and the temperature of the reaction. However, the concentration range can be readily ascertained using the assays described in the Examples. For example, a standard preparation of lambda DNA can be heat-treated according to Example 1. The DNA can then be subjected to a series of enzyme mixtures containing ligase and cofactors. An additional enzyme is titrated to determine a preferred concentration for that enzyme in the mixture. In this way, DNA repair can be optimized. After amplification of each sample, the amount of the amplified DNA can be determined by gel electrophoresis revealing the preferred concentration range for the test enzyme.

The universal enzyme mixture can be used prior to or during polynucleotide amplification or other synthesis.

As illustrated in the Examples, depending on the type of damage, it may be desirable to supplement the universal enzyme mixture with additional repair enzymes depending on the nature of the DNA damage. The utility of individual repair enzymes or mixtures of repair enzymes can be determined using the assays described in the Examples and in the Figures to determine their suitability for repairing a particular polynucleotide.

Repair of General or Specific Damage to Polynucleotides (a) General Damage

Determining the nature of damage in a polynucleotide is time-consuming. If some form of damage to a polynucleotide is suspected, for example, the polynucleotide is poorly amplified, it is preferable not to have to identify the lesion or lesions. In these circumstances, a universal mix of enzymes such as described above may be utilized to determine whether improved amplification is obtained. If the improvement is sufficient using the universal mixture then no further action is required. If the improvement is not sufficient, additional enzymes can be added to the mixture as described herein until the preferred result is obtained. The entire assay may be achieved in a single reaction vessel such as a 96 well dish. Each micro-well in the dish is available for a different enzyme mixture including the universal mixture plus enzymes selected to address each class of damage outlined below.

The protocol for selecting enzymes for repair of general damage or unknown damage of DNA is provided in FIG. 12 (flow chart) and in the assays described in the Examples.

(b) Specific Damage (i) AP Sites

The loss of a base is the most common form of spontaneous DNA damage. Polymerases and polymerase-based techniques are adversely affected by the presence of these abasic sites. The effectiveness of primer extension reactions is enhanced by repairing any abasic sites found in a polynucleotide. This is achieved in one embodiment by Endo IV activity that cleaves the phosphate backbone at the abasic site. This leaves an extendable 3' OH on the DNA fragment 5' to the cleaved abasic site. It also leaves a deoxyribose-5'-phosphate (dR5P) on the DNA fragment 3' to the cleaved abasic site. A polymerase can extend from the free 3' OH replacing the cleaved abasic site with a correct nucleotide. The dR5P may be removed by an enzyme that specifically targets dR5Ps such as mammalian pol beta or the 8 Kd N-terminal portion of mammalian pol beta (Deterding *JBC* 275:10463-71 (2000)), by a flap endonuclease activity present in certain polymerases such as E. coli DNA polymerase I or by a separate flap endonuclease such as FENI. The removal of dR5P can also occur by cleavage downstream of this group by the flap endonuclease activity. After removal of the dR5P and the generation of a 5' phosphate adjacent to the 3' OH, a ligase can seal this nick finishing the repair (see Examples 1-3).

(ii) Modified Nucleotides
(a) Thymidine Dimers

Light can damage DNA by inducing the formation of pyrimidine dimers. Pyrimidine dimers block the DNA extension reaction catalyzed by DNA polymerases such as Taq DNA polymerase and hence inhibit DNA amplification (Wellinger, et al. *Nucleic Acids Res.* 24(8):1578-79 (1996)). Consequently it is desirable to repair pyrimidine dimers prior to or during amplification. This can be achieved by adding a pyrimidine dimer glycosylase/lyase (Vande Berg, et al. *J. Biol. Chem.* 273(32):20276-20284 (1998)) to the universal enzyme mixture. The DNA backbone is cleaved 5' to the pyrimidine dimer and leaves a 3' hydroxyl moiety that is extendable by a DNA polymerase. In certain embodiments, extension at the 3' hydroxyl and subsequent formation and then cleavage of the lesion-containing flap generated during DNA extension results in a nick that is sealed by an enzyme capable of sealing the nick. Cleavage of the flap can be achieved by the extending polymerase, for example, *E. coli* polymerase I or by the action of a flap endonuclease ((Xu, Y., et al. *J. Biol. Chem.* 275(27):20949-20955 (2000), Liu, Y., et al., *Annu. Rev. Biochem.* 73:589-615 (2004)).

(b) Oxidative Damage, Alkylation and Deamination

Inaccuracies can be introduced into the products of DNA amplification reactions because of undesired nucleotide incorporation opposite a damaged base (Gilbert, et al. *Am. J. Hum. Gen.* 72:48-61 (2003); Hofreiter et al. *Nucl. Acids Res.* 29:4793-9 (2001)). These inaccuracies can be discovered after amplifying, cloning and sequencing the same sample many times. Inaccuracies due to base damage can also be identified by comparing sequence data before and after sample treatment with an enzyme such as UDG, which removes one of the common types of mutagenic DNA lesions (Hofreiter, et al. *Nucl. Acids Res* 29:4793-9 (2001)). However, treatment with UDG creates an abasic site within the DNA that inhibits DNA amplification by primer extension. This may cause DNA samples to be refractory to amplification after UDG treatment. This AP site can then be repaired by a reaction mixture containing a ligase and preferably also an AP endonuclease and a polymerase. Removal of a uracil enables a polymerase in an amplification reaction that would normally be stopped at this site to continue amplifying the DNA. For example, Vent® polymerase activity is inhibited on DNA templates containing uracil. The ability to remove the uracil permits the polymerase to have enhanced effectiveness.

In contrast, it is here shown that including UDG with an enzyme mixture that includes a ligase and a polymerase can be successfully used to enhance the yield and fidelity of the product of polynucleotide copying or amplification. Examples 12-14 provide descriptions of various beneficial enzyme mixes that include UDG.

Modified nucleotides that are the product of oxidative damage can also be removed from the polynucleotide by Fpg or hOGG to leave a blocked polynucleotide where the blocked polynucleotide is repairable by an AP endonuclease such as Endo IV.

The effectiveness of enzyme pretreatment to repair oxidative damage to a polynucleotide prior to copying or amplification is illustrated in Example 9 in which improved fidelity of the copied polynucleotide product is demonstrated using an enzyme mixture containing a ligase, a polymerase, Endo IV and Fpg.

Other modified nucleotides such as alkylated bases or deaminated bases where cytosine is converted to uracil, guanine to xanthine or adenine to hypoxanthine give rise to miscoding. Removal of these modified nucleotides is desirable. These modified bases can be removed by UDG as discussed above or by AlkA or Aag as described in Example 10.

(iii) Cross-Links

Additional nucleotide excision repair (NER) proteins (Minko et al. *Biochemistry* 44:3000-3009 (2005); Costa et al. Biochimie 85(11):1083-1099 (2003); Sancar *Ann. Rev. Biochem* 65:43-81 (1996)) can be used to repair damage resulting from formaldehyde and bulky adducts as well as damage that results in chemically-modified bases that form DNA-protein cross-links. At least one of *E. coli* UvrA, UvrB, mutant UvrB, UvrC, UvrD or Cho (Moolenar et al. *Proc. Natl. Acad. Sci USA.* 99:1467-72 (2002)) can be used to make incisions at the 5' end and optionally the 3' end around a damaged site. Details about the properties and purification protocols of these enzymes can be obtained from Zou, Y., et al. *Biochemistry* 43:4196-4205 (2004). The repair process can be completed by means of a DNA polymerase, a DNA ligase and optionally a flap endonuclease.

The generation of a 3' hydroxyl at a 5' incision site can be useful if the NER enzyme(s) cleave the DNA but leave a blocked 3' end on the DNA that inhibits primer extension. An example would be if the NER enzyme(s) cleaved the DNA and left a 3' phosphate. This would not be extendable by known DNA polymerases unless the 3' phosphate was removed by, for example, *E. coli* Endo IV.

If the NER enzyme or enzymes cleaves 5' and 3' to the DNA lesion then the damage is removed when the newly released oligonucleotide dissociates from the DNA. A polymerase can simply fill in the excised region of DNA leaving a nick, which ligase then seals to complete the repair. In certain cases, the polymerase may fill in the DNA and then proceed to displace the remaining DNA strand. In these circumstances, an enzyme with flapase activity permits a nick to be formed that a ligase can seal. In cases in which the NER enzyme or enzymes only cleaves 5' to the damage, the polymerase preferably displaces the original DNA strand until it is past the damage, at which point a flapase cleaves the DNA flap to create a ligatable nick. The flapase may be active before and after the DNA lesion is reached. Preferably, the polymerase and flapase activities work to eventually displace and remove the DNA lesion leaving a ligatable nick, thus repairing the DNA template. An example of the effectiveness of the above approach is provided in Example 7.

(iv) Nicks, Gaps and Mismatched Polynucleotides

Nicks and gaps in the DNA backbone can lead to truncated primer extension products and formation of chimera by undesirable hybridization of single strand regions. Heteroduplex DNA can be a problem in multi-template PCR and in homogeneous template PCR (Lowell, J. L. & Klein, D. A. *Biotechniques* 28:676-681 (2000); Thompson, J. R., et al. *Nucl. Acids Res.* 30(9):2083-2088 (2002); Smith, J. & Modrich, P. *Proc. Natl. Acad. Sci. USA* 94:6847-6850 (1997)). For example, chimera can be formed at the mismatch sites.

The combined effect of a ligase and a polymerase together optionally with an enzyme that recognizes and cleaves at heteroduplex sites (T7 Endo I and mutants thereof) contained within a universal enzyme mixture results in repairs of nicks, gaps, heteroduplexes and chimera in the DNA thus enhancing yield and fidelity of polynucleotide copying and amplification reactions. Example 8 demonstrates the beneficial effects of using T7 Endo I and a ligase as illustrative of the above. The useful range of the T7 endonuclease or mutant:DNA ratio can be expanded by including a DNA ligase activity to minimize the detrimental effects of non-specific cleavage in the heteroduplex cleavage reaction. This approach does not require quantitation of DNA and avoids the extra steps after the PCR reaction required by Lowell, et al. *Biotechniques* 28:676-681 (2000); and Smith, et al. *Proc. Natl. Acad. Sci. USA* 94:6847-6850 (1997).

For some polynucleotides, the nature of the damage might be known. By way of illustration, a mixture of enzymes can be selected according to section (b) above for repairing the specific damage. Where the damage is unknown or the sources are mixed, the universal mix described herein including in the examples may be employed.

DNA Microarrays

DNA microarrays are a powerful methodology used to analyze DNA samples (Lipshutz et al. *Curr Opinion in Structural Biology* 4:376-380 (1994); Kozal, et al. *Nat Med* 2(7): 753-9 (1996)). The amount and quality of information from microarray analysis of damaged DNA would benefit from first repairing the damaged DNA.

Discussion of the Examples and Figures

The enhancement in yields of product after amplification is shown both generally and for specific sources of damage: FIGS. 1A-1D, and 4 (heat damage), 2A-2B (citrate), 8A-8C (UV irradiation), 12, 3, 5 and 17 (general damage to DNA, environmental DNA, stored krill DNA and cave bear DNA) and 9A-9B (subject to undesirable heteroduplex formation) as well as the impact of different incubation times at different temperatures (FIGS. 13 and 14). The enhancement of fidelity is demonstrated in FIGS. 10A-10B and 11. FIGS. 6A-1 to 6A-9, 6B-1 and 6B-2 provide details of sequences that are homologous with Taq ligase and T4 ligase sequences. FIG. 7 describes a DNA sequence for Tth Endo IV and FIGS. 18-1 to 18-2 describe a sequence for plasmid pNEB0.920. FIG. 15 shows that multiple fragmented DNA can be repaired to form a template suitable for amplification to produce an amplicon. Benefits of repair mixes for cloning and transformation are illustrated in FIGS. 15 and 16.

Figure 1A:
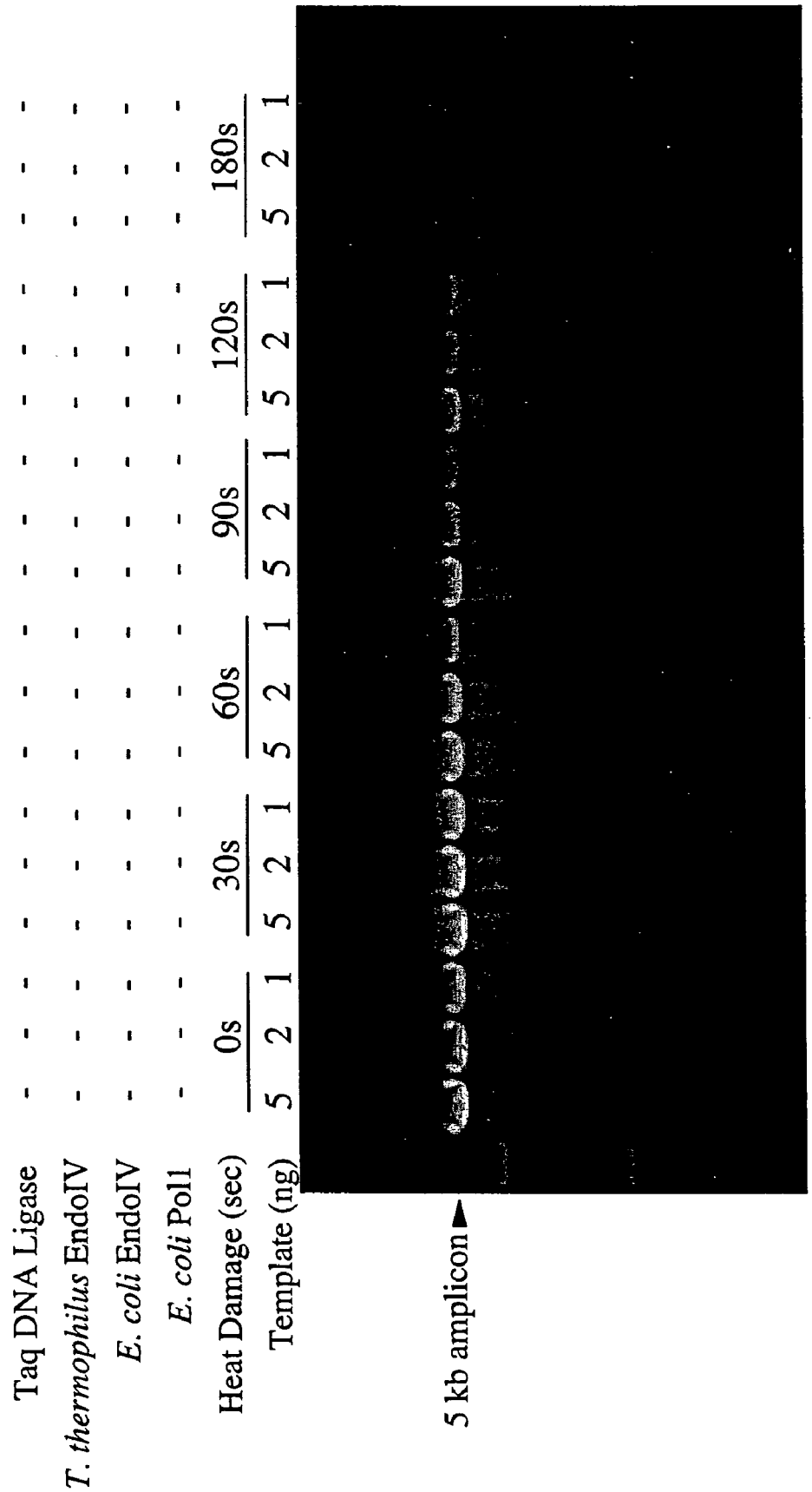
FIGS. 1A-1D show enhanced amplicon yield from heat-damaged lambda DNA after pre-incubation with specified enzymes.

Example 1 and FIGS. 1A-1D show that amplicon yields obtained from PCR amplification are substantially negatively affected when the template DNA is damaged beyond a certain threshold of damage (e.g., about 90 seconds heat treatment) (see FIG. 1A). The effect of this damage on amplification can be reversed and amplicon yields enhanced by incubating the DNA with a mixture of enzymes before amplification (see FIGS. 1B, 1C and 1D). In addition, if amplicon yields of assumed "undamaged" DNA can be enhanced by adding the enzyme mixture described then in fact, the DNA is deemed to have been damaged.

Example 1 shows that the effect of the enzyme mixture on amplification of DNA is not dependent on a single type of AP endonuclease or ligase, but instead endonucleases or ligases from multiple alternative sources can be used. For example, thermostable Tth Endo IV was found to be as effective as *E. coli* Endo IV and *E. coli* ligase was as effective as the thermostable Taq ligase.

Figure 2A:
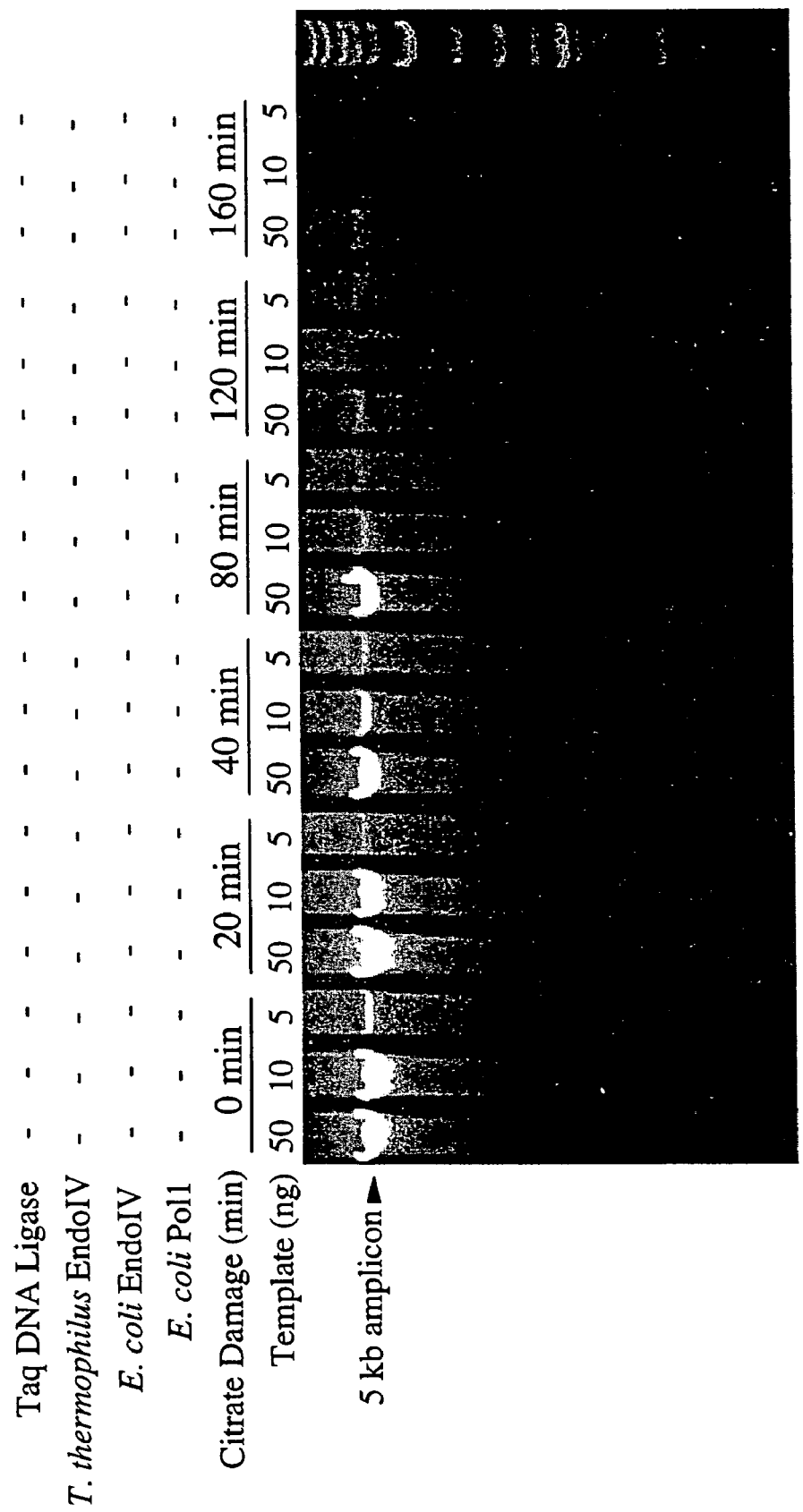
FIGS. 2A and 2B show the effect of citrate buffer pH 5 treatment of template DNA on amplicon yield.
Figure 2B:
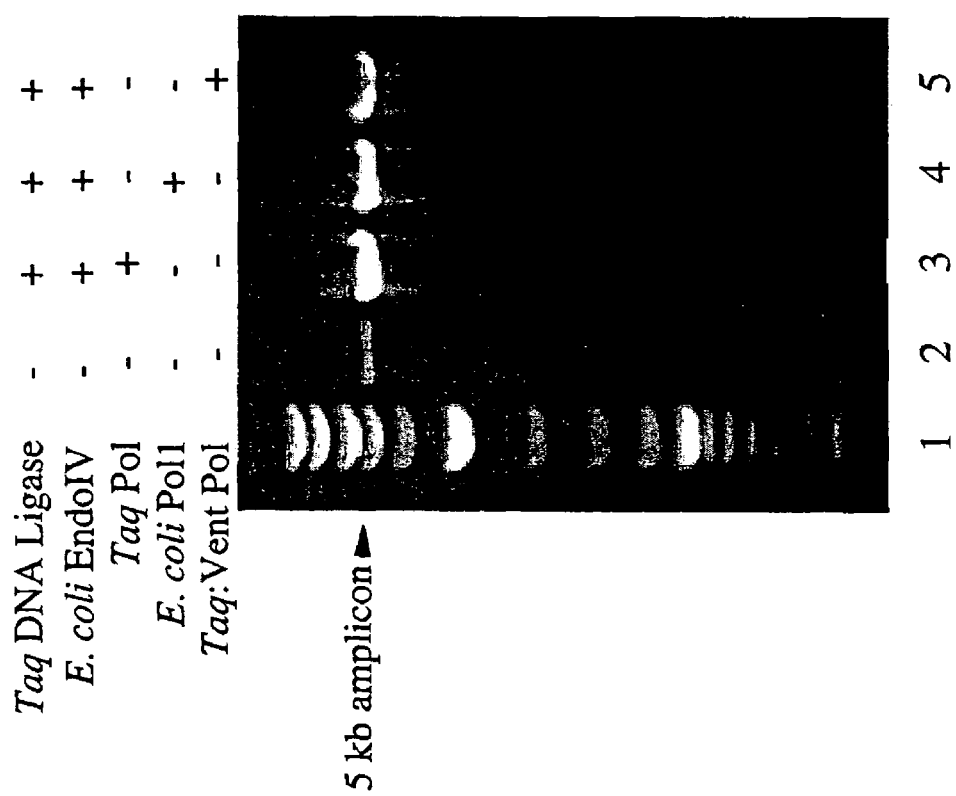

Example 2 and FIGS. 2A-2B show the negative effect on amplification yields of another type of DNA damage—depurination, which is induced in the presence of low pH. Moreover, the example shows that the effect of a mixture of enzymes on amplification of DNA is not dependent on a single type of polymerase but rather polymerases from multiple alternative sources can be used. For example, *E. coli* PolI can be substituted by Taq DNA polymerase or a mixture of Taq and Vent® DNA polymerases to produce enhanced yields.

Example 3 and FIG. 3 show that the enhancement of amplification yields can be observed with short (200 bp) fragments. In fact, enhancement of amplification yields should be observable for a wide range of sizes of DNA templates from as short as 100 bases to as long as 100 kb and it is believed that amplification yields for DNA even larger than 100 kb can be achieved.

FIG. 3 also shows that even when the DNA has been damaged through storage in a crude form (for example, within the cells of an organism that has itself been stored), amplification yields are significantly enhanced by the addition of a mixture of enzymes prior to amplification. Although the mixture of enzymes was added to template DNA prior to amplification, a similar yield effect can be seen when the template DNA is incubated with the mixture of enzymes that are thermostable equivalents during amplification or during a pre-amplification step.

Example 4 and FIG. 4 show that ligase alone can enhance amplicon yield, but adding an AP endonuclease further enhances the yield. The best result was observed in this example when a ligase, an AP endonuclease, and a DNA polymerase were used prior to amplification. Furthermore, this example demonstrates that repair is not DNA size dependent. For example, similar results were obtained with 5 kb and 10 kb amplicons.

Example 5 and FIG. 5 show that an enhanced yield from amplification can be achieved using a ligase, which may be an $NAD^+$ dependent or ATP dependent enzyme and that this effect can be achieved without limitation to a single source of ligase. FIG. 5 shows that Taq ligase and T4 ligase are both effective in enhancing amplification yield even when used without additional enzymes in a pre-incubation mix. This effect is also believed to occur if the ligase is added to the amplification mix (if thermostable). FIG. 5 also shows the benefit of this approach when amplifying environmental DNA obtained directly from soil samples that have been exposed in nature to a variety of damaging agents.

FIGS. 6A-1 to 6A-9, 6B-1 and 6B-2 and 7 are descriptions of enzymes or the sequence encoding enzymes used in the universal mixture of enzymes, which is so named because it can be broadly applied to damaged polynucleotides without specific knowledge concerning the damage itself. While the examples refer to DNA, amplification or copying of polynucleotides is more generally envisaged. In general, the conditions under which amplification is found to be improved are also applicable to enhancing copying of polynucleotides generally even if this is not explicitly stated in all cases.

All references cited herein, as well as U.S. application Ser. No. 11/255,290 filed Oct. 20, 2005 and U.S. provisional application Ser. Nos. 60/620,896 filed Oct. 21, 2004, 60/646, 728 filed Jan. 24, 2005 and 60/673,925 filed Apr. 21, 2005, are incorporated by reference.

EXAMPLES

Example 1

Enhancing Amplicon Yields From DNA Damaged by Heat Treatment

An assay was developed for optimizing the use of selected reagents to repair DNA prior to amplification.

Generation of Various Extents of Heat Damage

Various amounts of DNA damage were induced by heat treatment. This was achieved as follows: 100 µL lambda DNA (NEB#N3011, New England Biolabs, Inc., Ipswich, Mass.) at 0.5 mg/ml was aliquoted into separate tubes for heat treatment at 99° C. for 30 sec, 60 sec, 90 sec, 120 sec, and 180 sec, respectively in a PE2700 thermal cycler. A sample was used as a template for amplification without pretreatment.

The remaining damaged DNA was pretreated by the mixture of enzymes as follows: The damaged DNA templates were incubated at room temperature in the following mixture for 10 minutes:

DNA (5 ng, 2 ng and 1 ng);

100 µM dNTPs (NEB#M0447, New England Biolabs, Ipswich, Mass.);

1 mM NAD+ (Sigma#N-7004, Sigma, St. Louis, Mo.);

80 units Taq ligase (NEB#M0208, New England Biolabs, Ipswich, Mass.) or 40-100 units of *E. coli* ligase (NEB#M0205S);

0.1 units *E. coli* DNA polymerase I (*E. coli* polI) NEB#M0209, New England Biolabs, Inc., Ipswich, Mass.);

10 units *E. coli* Endo IV (NEB#M0304, New England Biolabs, Inc., Ipswich, Mass.) or 10 units of Tth Endo IV;

1× Thermopol buffer (NEB#B9004, New England Biolabs, Inc., Ipswich, Mass.) to a final volume of 96 µL.

At the end of the reaction, the samples were transferred to ice and then amplified.

DNA Amplification Reaction

DNA amplification of lambda was performed using the following primers: CGAACGTCGCGCAGAGAAACAGG (L72-5R) (SEQ ID NO:1) and CCTGCTCTGCCGCTTCACGC (L30350F) (SEQ ID NO:2) according to the method of Wang et al. *Nucl. Acids Res.* 32: 1197-1207(2004).

4 µl of amplification mixture was added to 96 µl of the above repair mixture. The amplification mixture contained 100 µM dNTPs, 5 units Taq DNA polymerase, 0.1 units Vent® (exo+) DNA polymerase, $5 \times 10^{-11}$ M primer L72-5R and $5 \times 10^{-11}$ M primer L30350F in 1× Thermopol buffer.

To correct for any enzyme storage buffer effects, when a repair enzyme was omitted from a reaction, the appropriate volume of its storage buffer was added to the reaction. In all cases, the amplification reactions were processed in a thermal cycler using the following parameters: 20 sec at 95° C. for 1 cycle followed by 5 sec at 94° C., then 5 min at 72° C. for 25 cycles. The size of the amplicon being amplified was 5 kb.

The results of amplification of DNA (5 kb) were determined by 1% agarose gel elecrophoresis. 6× loading dye (Molecular Cloning: A Laboratory Manual, 3rd ed., eds. Sambrook and Russell, Cold Spring Harbor Press, Cold Spring Harbor, N.Y., 2001, pp. 5.4-5.17) was added to the 100 µl amplification reactions. 20 µl of this solution was then loaded onto the agarose gel along with 1 µg of 2-log ladder (NEB#N3200, New England Biolabs, Inc., Ipswich, Mass.) as a size standard.

Figure 1B:
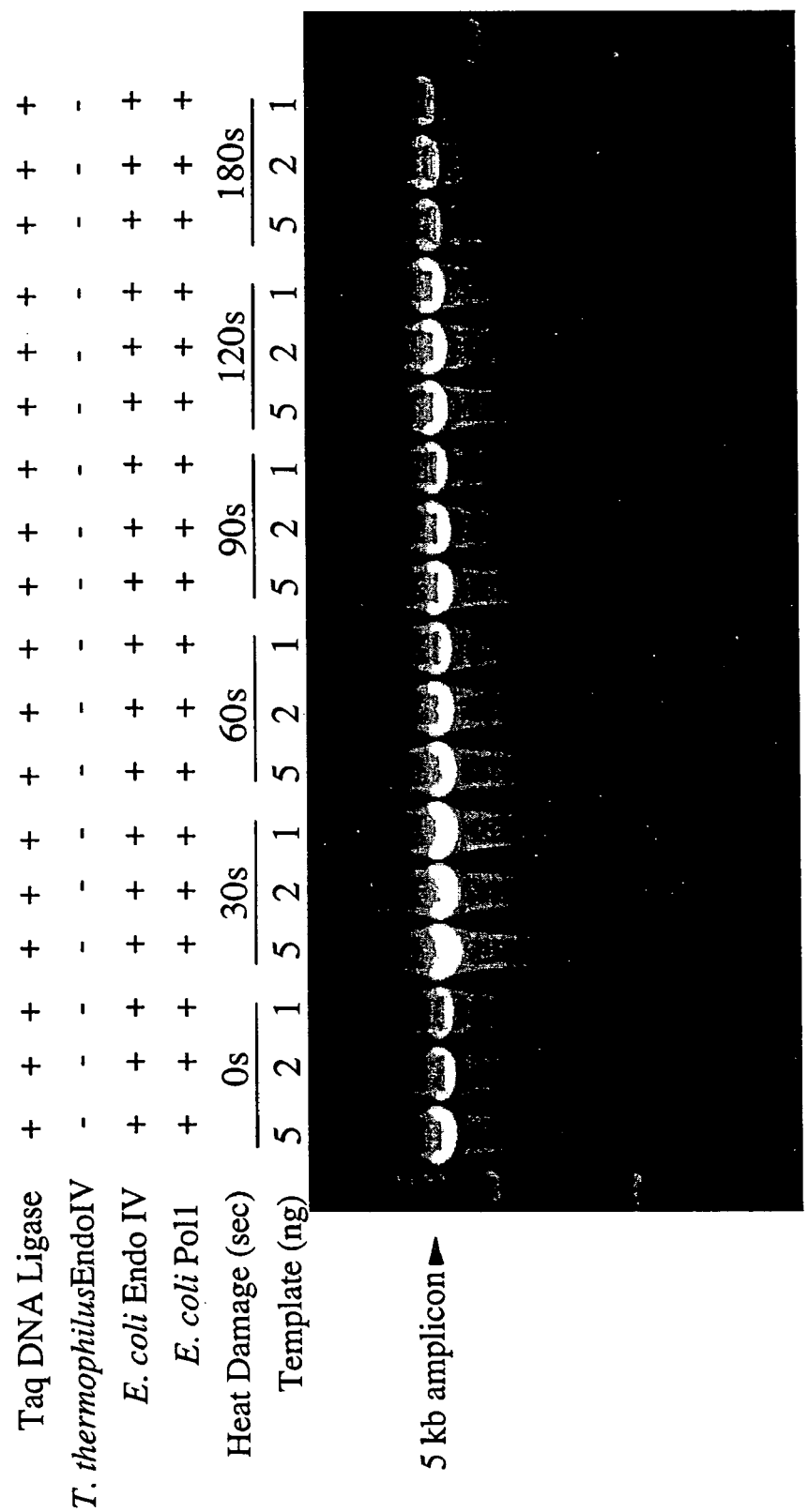
Figure 1C:
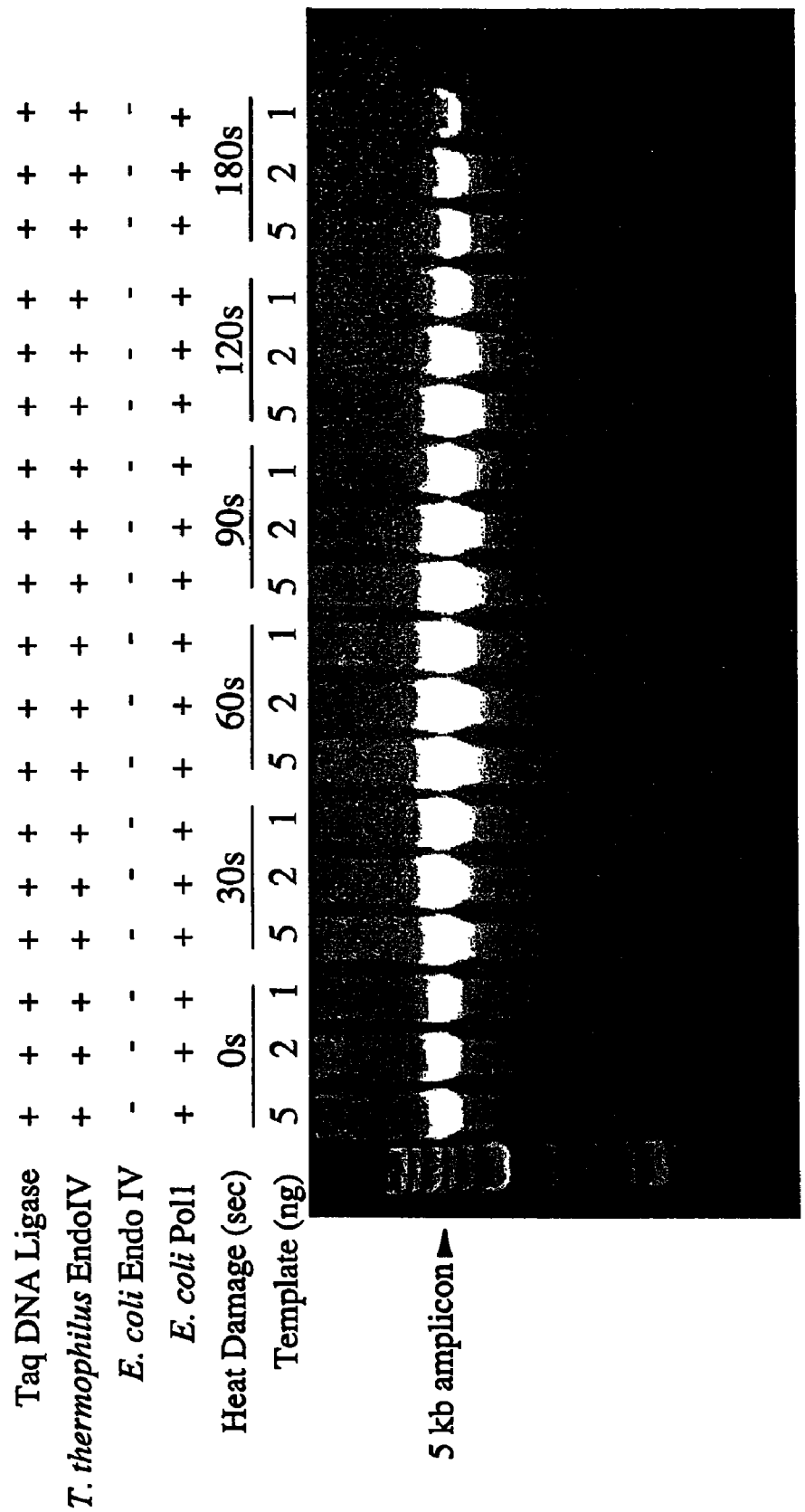
Figure 1D:
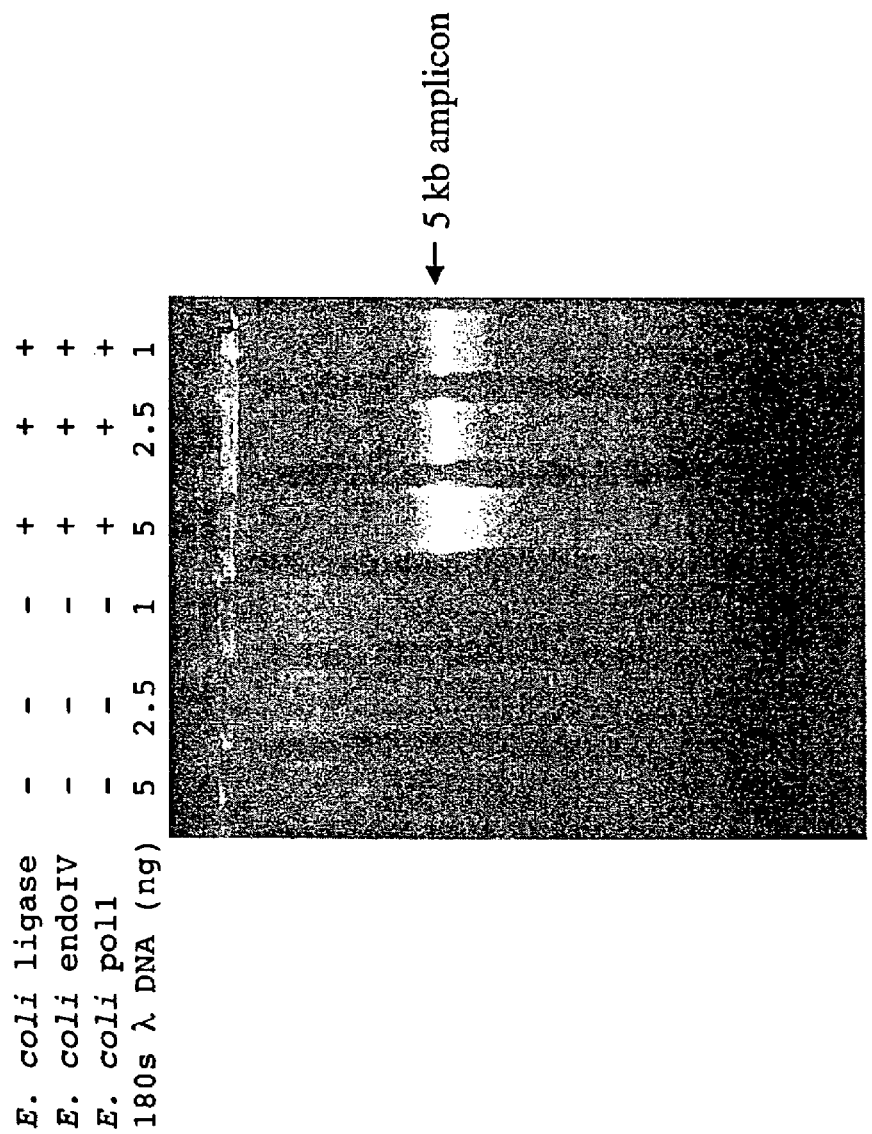

The amount of amplified DNA for each sample was compared by gel electrophoresis and the results are shown in FIGS. 1A-D. When the samples were treated with a mixture of enzymes after heat treatment but prior to amplification, significant enhancement of amplification yields was achieved (FIGS. 1B, 1C and 1D).

Example 2

Enhanced Amplicon Yields from DNA with low pH-Induced Abasic Sites Following Pretreatment with an Enzyme Mixture Generation of Various Extents of Damage Resulting from Abasic Sites To assay the extent of repair of damaged DNA, various amounts of DNA damage was first induced by acidic pH. This was achieved as follows:

DNA was depurinated as described by Ide, H., et al. *Biochemistry* 32(32):8276-83 (1993). Lambda DNA (NEB#N3011, New England Biolabs, Inc., Ipswich, Mass.) was ethanol precipitated. The DNA was resuspended in depurination buffer (100 mM NaCl, 10 mM citrate, pH 5.0) at a concentration of 0.5 mg/ml and incubated at 70° C. for 0, 20, 40, 80, 120, and 160 minutes. The sample was then ethanol precipitated and resuspended in 0.01 M Tris, 0.001 M EDTA, pH 8.0. The DNA concentration was determined by measuring the $A_{260}$ of the DNA-containing solutions after calibrating with a buffer control.

Pretreatment of DNA with a Mixture of Enzymes

The damaged DNA was incubated at room temperature for 10 minutes in the following mixture:

DNA (2.5 ng of damaged DNA after 120 minute of low pH treatment);

100 µM dNTPs;

1 mM NAD+;

80 units Taq ligase;

0.1 units Taq DNA polymerase or 0.1 units *E. coli* PolI (NEB#M0209, New England Biolabs, Inc., Ipswich, Mass.)) or 0.1 units Taq:0.002 units of Vent® Pol, (NEB#M0254, New England Biolabs, Inc., Ipswich, Mass.));

10 units *E. Coli* Endo IV;

1× Thermopol buffer to a final volume of 96 µl.

The above mixture was incubated at room temperature for 10 minutes and then transferred to ice prior to amplification.

DNA Amplification Reaction

Amplification was performed as described in Example 1 to generate a 5 kb amplicon. Amplicon yields were increased as compared with negative controls (FIG. 2A) by treating lambda DNA containing abasic sites with the mixture of enzymes. The results are shown in FIG. 2B for a series of pretreatments using different enzyme mixtures. The enzyme mixtures were varied with respect to the polymerase (*E. coli* PolI or Taq:Vent®).

Example 3

Enhanced Amplicon Yields of DNA Extracted from an Intact Organism After Storage in a Preservative Genomic DNA was isolated from *Meganyctiphanes norvegica* (Krill) as described in Bucklin, A. & Allen, L. D. *Mol. Phylogenet. Evol.* 30(3):879-882 (2004). The Krill had been stored in ethanol for about 5 years.

Pretreatment of the Krill DNA by a mixture of enzymes was carried out as follows:

50 ng of *M. norvegica* genomic DNA;

100 µM dNTPs;

1 mM NAD+;

40 units of Taq ligase;

0.5 units Taq DNA polymerase, 0.2 units Vent® (exo+) DNA polymerase, or a Taq:Vent® (exo+) mix containing 0.05 units of Taq DNA polymerase and 0.001 units of Vent® (exo+);

10 units *E. coli* Endo IV;

1× Thermopol buffer to a final volume of 96 µl.

This reaction was incubated 15 minutes at room temperature before proceeding to the amplification step.

DNA Amplification Reaction

The amplification primers corresponded to 52F and 233R as described in Bucklin, A. & Allen, L. D. *Mol. Phylogenet. Evol.* 30(3):879-82 (2004) generating a 200 bp amplicon.

| | | |
|---|---|---|
| 52F: | TTTTTAGCAATACACTACACAGCAA | (SEQ ID NO: 3) |
| 233R: | ATTACGCCAATCGATCACG | (SEQ ID NO: 4) |

Primers were added to a final concentration of 0.5 µM, and each dNTP to a final concentration of 200 µM. 1 µl of the 50:1 Taq:Vent® mix (5 units Taq DNA polymerase and 0.1 units Vent® (exo+) DNA polymerase added to the reaction) was then added to each reaction to a final volume of 100 µL.

For the control reaction (Lane 1), no Endo IV, Taq ligase or pretreatment polymerase was added. Volumes were adjusted accordingly. In reactions in which repair enzymes were omitted, the appropriate volume of enzyme storage buffer was added to control for buffer effects.

Cycling conditions were as follows: 30 sec at 94° C., 30 sec at 52° C. and 1 min 40 sec at 72° C. for 40 cycles. 25 µL (one quarter of the reaction) was prepared, loaded on a 1% agarose gel, electrophoresed, and visualized as described above.

Increased amplicon yield from krill genomic DNA was observed after preincubation of the samples using the enzyme mixtures described above (FIG. 3).

Example 4

Enhanced Yields of a Large (10 kb) Amplicon from Heat-Damaged DNA

Heat-damaged DNA was prepared as described in Example 1. Lambda DNA was heated to 99° C. for 180 sec.

Pretreatment of damaged DNA by a mixture of enzymes was carried out as follows:

Lambda DNA (1 µg of 180 sec heat-treated DNA);
100 µM dNTPs;
1 mM NAD$^+$;
80 units of Taq ligase;
0.1 unit of E. coli PolI;
100 units of E. coli Endo IV;
1× Thermopol buffer to a volume of 96 µL.

The mixture was incubated for 10 minutes prior to amplification.

DNA amplification was performed as described in Example 1, except where specified below. Primers were added to the above 96 µl of preincubation mixture. Primer L71-10R (sequence GCACAGAAGCTATTATGCGTC-CCCAGG) (SEQ ID NO:5) replaced L72-5R in Example 1. The 1 cycler thermal cycler program (Bio-Rad, Hercules, Calif.) was: 20 sec at 95° C. for 1 cycle, 5 sec at 95° C., 10 min at 72° C. for 25 cycles and then 10 min at 72° C. for 1 cycle. Amplicon size was 10 kb.

The DNA was visualized as described in Example 1 with the following exceptions. 20 µl of 6× loading buffer was added to the 100 µl amplification reaction. 10 µl of this solution was diluted to 100 µl with H$_2$O and 1× loading buffer. 20 µl of this was loaded into each lane. The gel was a 0.8% agarose gel. The results are shown in FIG. 4.

Example 5

Improved Amplification Yield of DNA from Environmental DNA (Extracted from Soil Samples)

Environmental DNA was isolated from the soil using an UltraClean Soil DNA Kit from MoBio Laboratories, Inc., Carlsbad, Calif. (catalog #12800-50).

Pretreatment of DNA with a Ligase

A final volume of 100 µl containing 0.6 µg of environmental DNA isolated from soil and one of the two ligases described below in (a) and (b) formed the reaction mixture. This reaction mixture was then incubated at room temperature for 15 min.

(a) 1× Taq ligase buffer (New England Biolabs, Inc., Ipswich, Mass.) and 80 units of Taq ligase.

(b) 1× T4 ligase buffer (New England Biolabs, Inc., Ipswich, Mass.) and 800 units of T4 ligase (NEB#M0202, New England Biolabs, Inc., Ipswich, Mass.).

1 µl of reaction mixture was used in the amplification reaction described below.

DNA Amplification Reaction

DNA amplification was performed using primers: GGGGGXAGAGTTTGATCMTGGCTCA (SEQ ID NO:6) and GGGGGXTACGGYTACCTTGTTACGACTT (SEQ ID NO:7) (M=C or A, Y=C or T, X=8-oxo-Guanine). These primers target 16S rDNA having an amplicon size of 1.6 Kb.

The 50 µl reaction contained 10 pmol of each of the primers, 1 µl of the repaired environmental DNA, 200 µM dNTPs, 1× Thermopol buffer, and 1.25 units Taq DNA polymerase. The amplification was performed using the following cycling parameters: 5 min at 94° C. for 1 cycle, 30 sec at 94° C., 1 min at 55° C., 1 min 40 sec at 72° C. for 32 cycles, then 5 min at 72° C. for 1 cycle.

Gel electrophoresis was performed as described in Example 1. The results are shown in FIG. 5.

Example 6

Enhanced Amplicon Yield of Ultraviolet Light-Damaged DNA

To determine conditions for assaying the effectiveness of DNA repair, 50 µg lambda DNA (NEB#N3011, New England Biolabs, Inc., Ipswich, Mass.) was diluted in TE buffer (10 mM Tris-HCl, 1 mM EDTA, pH 7.5) to a concentration of 50 µg/ml and irradiated with 36 J/m$^2$ UV light for 0, 10, 20, 30, 40 and 50 sec.

Pretreatment of damaged DNA by a mixture of enzymes was carried out as follows:

The damaged DNA was incubated at room temperature for 15 minutes in the following mixture:

DNA (50 ng of lambda DNA-damaged for 0, 10, 20, 30, 40, or 50 seconds);
200 µM dNTPs;
1 mM NAD$^+$;
400 units Taq ligase;
0.1 units E. coli DNA polymerase I;
10 units E. coli Endo IV;
80 units or 10 units T4 PDG (also referred to as T4 Endo V). (Trevigen, Gaithersburg, Md.);
1× Thermopol buffer
Adjust volume with water to 50 µl.

After the 15 minutes incubation, the 50 µl reaction mixture was added to 50 µl of an amplification solution. The amplification solution consisted of 40 pmol of each primer (L72-5R and L30350F as described in Example 1 or L72-2R (the DNA sequence was CCATGATTCAGTGTGCCCGTCTGG) (SEQ ID NO:8), 1× Thermopol buffer, 1 mM NAD$^+$, 200 µM dNTPs, 2.5 units Taq DNA polymerase (NEB#M0267, New England Biolabs, Inc., Ipswich, Mass.), and H$_2$O to a final volume of 50 µL. Combining the 50 µL repair reaction with the 50 µl amplification solution gave a final volume of 100 µl.

The 100 µl solutions were placed into a thermal cycler.
For the L72-5R and L30350F primer combination:
5 min at 94° C. for 1 cycle; 30 sec at 94° C., 60 sec at 58° C., and 4 min at 72° C. for 30 cycles; 5 min at 72° C. for 1 cycle.
For the L72-2R and L30350F primer combination:
5 min at 94° C. for 1 cycle; 30 sec at 94° C., 60 sec at 58° C., and 2 min at 72° C. for 30 cycles; 5 min at 72° C. for 1 cycle.

Figure 8:
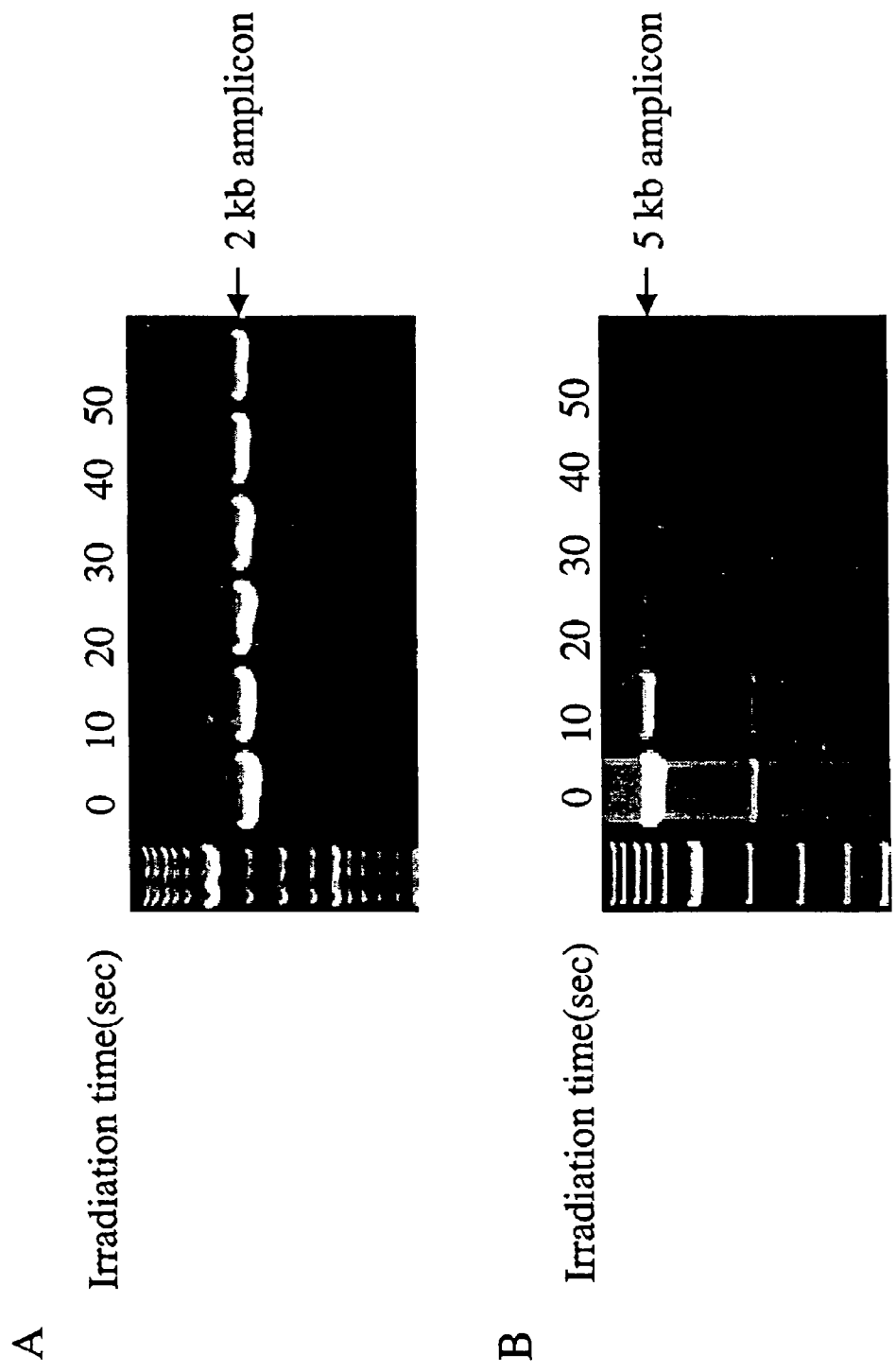
Figure 8:
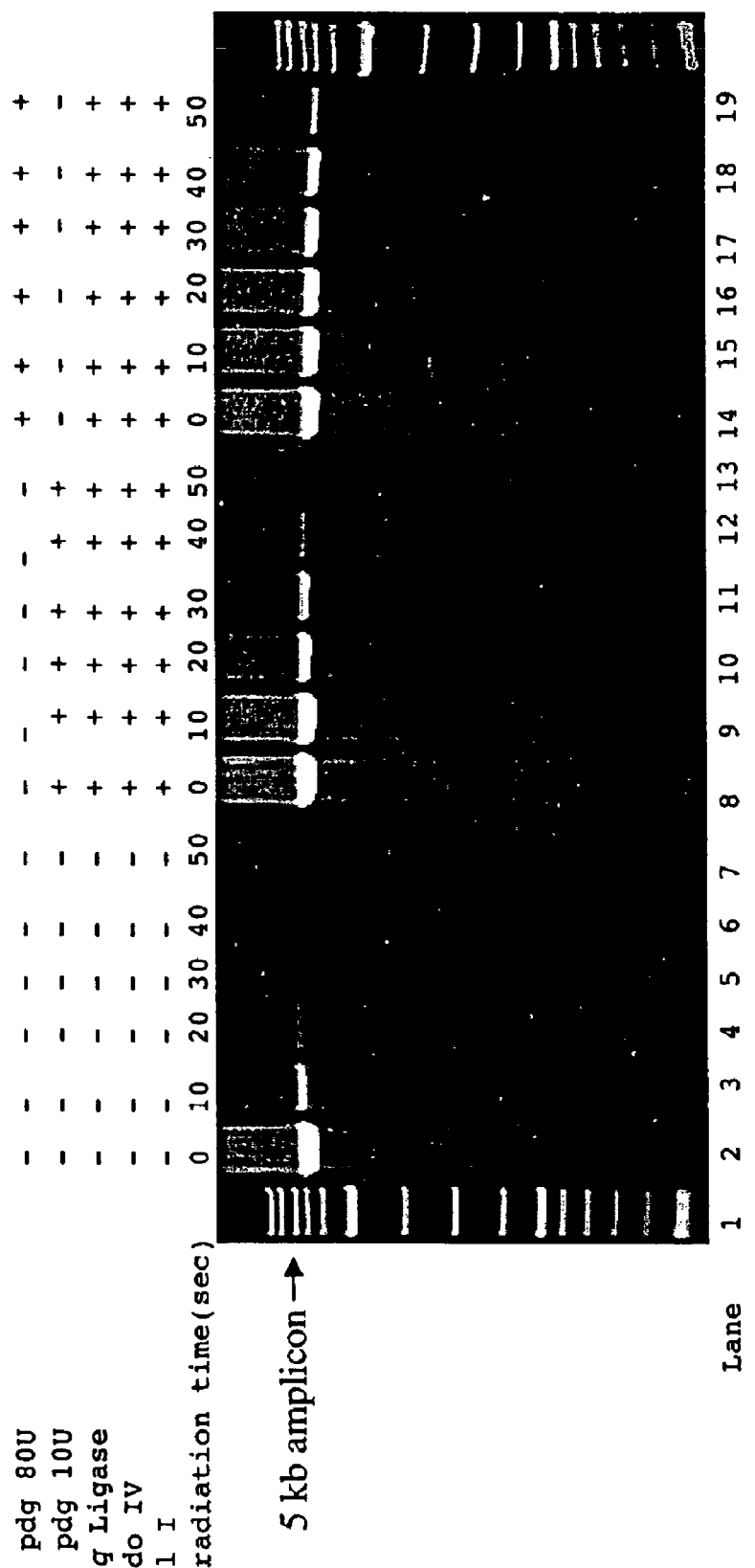

The presence of amplification product was visualized on a 1.8% agarose gel using ethidium bromide. The size of any band was compared against a lane containing the 2-log ladder (NEB#N3200S, New England Biolabs, Inc., Ipswich, Mass.) size standards. The results are shown in FIG. 8.

Example 7

Enhanced Amplicon Yield of DNA Using the Nucleotide Excision Repair Proteins, UvrA, UvrB and UvrC Increased amplicon yield from krill genomic DNA is determined after pre-incubation of the samples using an enzyme mixture containing proteins involved in nucleotide excision repair.

Pretreatment of stored DNA by a mixture of enzymes is carried out as follows:

Stored DNA is incubated for 1-180 minutes at 4-37° C. in the following mixture:
DNA: 50 ng of *M. norvegica* genomic DNA;
100 μM dNTPs;
1 mM ATP;
400 units of Taq ligase;
0.1 units *E. coli* DNA polymerase I;
10 nM *E. coli* UvrA, 250 nM *E. coli* UvrB (or mutant UvrB*), plus or minus 50 nM *E. coli* UvrC;
1× Thermopol buffer to a final volume of 96 μl.
*for mutant UvrB, see Zou, Y., et al. *Biochemistry* 43:4196-4205 (2004).

DNA amplification reactions are conducted as described in Example 3.

Example 8

Increasing Sequence Accuracy of a DNA After Removal of Incorrect Nucleotides on at Least One Strand by Means of Enzyme Cleavage of Heteroduplexes Experimental Conditions A. Adding Taq ligase to T7 Endo I was demonstrated to permit the use of an increased concentration of T7 Endo I in a DNA preparation without randomly degrading the DNA.

The assay relies on treating a supercoiled DNA containing a cruciform structure with increasing amounts of T7 Endo I. 0, 1.6, 3.1, 6.2, 12.5, 25, 50, 100, 200, or 400 units of T7 Endo I (NEB#M0302, New England Biolabs, Inc., Ipswich, Mass.) was added to 50 μl reactions composed of 1 μg of pUC(AT) (Guan, C., et. al. *Biochemistry* 43:4313-4322 (2004)) and 1× NEBuffer 2 (NEB#B7002S, New England Biolabs, Inc., Ipswich, Mass.). Plasmid pAT25tetA can be used in place of pUC(AT) (Parkinson, M. J. & Lilley, D. M. *J. Mol. Biol.* 270:169-178 (1997) and Bowater, R. P., et. al. *Biochemistry* 33:9266-9275 (1994)). Another set of reactions were set up simultaneously and used the same components as described above with the addition of 1 mM $NAD^+$ (Sigma catalog#N-7004, Sigma, St. Louis, Mo.) and 100 units of Taq ligase (using a stock of NEB#M0208 at a concentration of 100 u/μl, New England Biolabs, Inc., Ipswich, Mass.). All reactions were incubated at 37° C. for 60 minutes.

The results were analyzed by running the reactions on a 0.9% TBE agarose gel, stained with ethidium bromide, and visualized using UV light (see FIGS. 9A and 9B). With no T7 Endo I present the pUC(AT) plasmid produced 2 bands on the gel corresponding to the supercoiled form (lower band) and the relaxed circular form (upper band).

T7 Endo I resolved the supercoiled pUC(AT) into the relaxed circular form and a linear form that ran intermediate to the supercoiled and relaxed circular forms. At certain T7 Endo I:DNA ratios, a smear was produced indicating that the T7 Endo I had degraded the DNA by non-specific enzymatic activity. The presence of Taq ligase significantly increased the usable T7 Endo I to DNA ratio. This ratio is further improved by substituting T7 Endo I with the mutant T7 Endo I described in International Publication No. WO 2005/052124.

B. The use of Method A to remove heterduplexes from PCR reactions.

Isolation of DNA from soil and amplification of the purified DNA is performed as described in Example 5 with the optional addition of 5 units T7 Endo I or mutant thereof. When T7 Endo I or mutant thereof is added, an additional amplification cycle is added (37° C. for 15 minutes for 1 cycle). The last step is to allow the T7 endonuclease to cleave any heteroduplexes formed.

Gel electrophoresis is performed as described in Example 1. Heteroduplex DNA is visualized on the gel as described in Lowell, J. L. & Klein, D. A. *Biotechniques* 28:676-681 (2000). Absence of heteroduplex DNA in the presence of T7 Endo I or mutants thereof shows the effectiveness of T7 Endo I or mutants thereof with a ligase.

Unit definitions are described with the product description for each of the enzymes recited herein in the NEB catalog, New England Biolabs, Inc., Ipswich, Mass. For example, the unit definition for T7 Endo I or mutant thereof is the amount of enzyme required to convert greater than 90% of 1 μg of supercoiled plasmid into greater than 90% linear DNA in a reaction volume of 50 μl in 1 hour at 37° C.

The T7 Endo I:DNA ratio can be increased without increasing non-specific cleavage of DNA in the presence of ligase.

Example 9

Enhancing the Sequence Accuracy of a DNA Amplication Reaction After Oxidative Damage Generating DNA with Oxidative Damage The DNA subject to oxidative damage was pWB407 (Kermekchiev, M. B. et al. *Nucl. Acids Res.* 31:6139-47 (2003)). The damage was incurred using a combination of methylene blue (MB) and visible light as described previously (Sattler, et al. *Arch. Biochem Biophys.* 376(1):26-3 (2000)). Plasmid DNA (200 μg/ml in distilled water) was spotted on parafilm stretches (50 μl drops). MB was added to the drops to a final concentration ranging from 0 to 50 (0, 3, 6, 12.5, 25 and 50) μg/ml (100 μl final volume). Plates with these parafilm stretches were placed on ice and illuminated for 8 min. with a 1×100-W lamp. The MB-light-treated DNA was precipitated, dried, and then re-suspended in 50 μl of TE buffer (pH 8.0). Final DNA concentration was determined by the absorbance of light at 260 nm.

DNA Amplification Conditions

A portion of pWB407 that contained the lacZ gene was amplified using primers 316-138, TGTCGATCAGGAT-GATCTGGACGAAGAGC (SEQ ID NO: 9), and 316-137, CGAAAGCTTTCAAGGATCTTACCGCTGTTGAGA (SEQ ID NO:10). Primers 316-138 and 316-137 were based on the previously-described primers Kfd-29 and H3B1a34, respectively (Kermekchiev, M. B. et al. *Nucl. Acids Res.* 31:6139-47 (2003)). The 100 μL PCR reactions contained either 10 or 50 ng of template DNA, indicated where appropriate, and 40 picomoles of each primer. The cycling conditions utilized varied with the thermal stable polymerase used for amplification.

Cycling conditions when using Taq DNA polymerase (NEB cat#M0267S, New England Biolabs, Inc., Ipswich, Mass.) had an initial denaturation step of 5 min at 94° C. for 1 cycle, then 30 sec at 94° C., 60 sec at 58° C., and 3 min 30 sec at 72° C. for 30 cycles, and finally 5 minutes at 72° C.

Cycling conditions when using Phusion™ DNA polymerase (NEB cat#F-530S, New England Biolabs, Inc., Ipswich, Mass.) had an initial denaturation step of 30 sec at 98° C. for 1 cycle, then 10 sec at 98° C., 30 sec at 62° C., and 1 min 30 sec at 72° C. for 30 cycles, and finally 5 min at 72° C.

The reaction outcomes were analyzed by loading 25 μL of the reaction on a 1.6% agarose gel, prepared, electrophoresed and visualized as described above. The marker used was the 2-log DNA ladder (NEB cat#N3200S, New England Biolabs, Inc., Ipswich, Mass.).

Amplification Accuracy Determination

The accuracy of DNA amplification from the pWB407 template was determined as described by Barnes, et al. *Gene* 112:29-35 (1992) and Kermekchiev, et al. *Nucl. Acids Res.* 31:6139-47 (2003). Amplicons containing the lacZ gene were generated from plasmids pWB407 that had been subjected to differing amounts of oxidative damage. The oxidative damage was performed using methylene blue as described above. The PCR reactions were performed using 50 ng of template as described above. After cycling, 10 units of the restriction endonuclease, DpnI, was added to each 100 μL PCR reaction and incubated for 2 hours at 37° C. This step eliminated the original template plasmid. Next, the resulting amplification products were extracted with phenol/chloroform and precipitated using isopropanol (Molecular Cloning: A Laboratory Manual, 3$^{rd}$ ed., eds. Sambrook and Russell, Cold Spring Harbor Press, Cold Spring Harbor, N.Y., 2001, pp. 6.25, A8.12-A8.24). Precipitated products were re-suspended in H$_2$O and cut with the restriction endonucleases StyI and HindIII using conditions recommended by the manufacturer (New England Biolabs, Inc., Ipswich, Mass.). The DNA digestion reactions were stopped by inactivating the HindIII and StyI enzymes by heating to 65° C. for 20 min. The restriction digestion products were purified using a microcon YM-100 column (Millipore, Billerica, Mass.) to eliminate short DNA fragments.

The repair reaction mixtures in a total of 50 μl contained 10 or 50 ng of pWB407 amplicons+/−methylene blue incubation. The repair reactions contained 20 mM Tris-HCl (pH 8.8 at 25° C.), 10 mM KCl, 10 mM (NH$_4$)$_2$SO$_4$, 2 mM MgSO$_4$, 0.1% Triton X-100, 1 mM NAD$^+$, 200 μM dNTPs (dATP, dTTP, dCTP, and dGTP), and various repair enzyme mixtures.

The repair enzyme mixtures used separately or in various combinations in a total volume of 50 μL were:
  0.4 units Fpg, NEB cat#M0240S, New England Biolabs, Inc., Ipswich, Mass.);
  200 units Taq ligase;
  0.1 units *E. coli* DNA polymerase I;
  10 units *E. coli* Endo IV;
  1 mM NAD$^+$;
  100 μM dNTPs;
  1× Thermopol buffer.

The reactions were incubated at 25° C. for 15 minutes. After the incubation, 50 μL of a PCR mix (20 mM Tris-HCl (pH 8.8 at 25° C.), 10 mM KCl, 10 mM (NH$_4$)$_2$SO$_4$, 2 mM MgSO$_4$, 0.1% Triton X-100, 1 mM NAD$^+$, 200 μM dNTPs (dATP, dTTP, dCTP, and dGTP), and either 2.5 units Taq DNA polymerase (NEB cat#M0267S, New England Biolabs, Inc., Ipswich, Mass.) or 1 unit of Phusion™ DNA polymerase was added to the 50 μL repair reaction and this new solution was subjected to thermal cycling conditions for PCR. The amplicons from these reactions were purified and restriction enzyme digested as described for other amplicons above.

The amplicons were cloned into the pWB407 plasmid. Plasmid pWB407 was prepared by digestion with the restriction endonucleases StyI and HindIII followed by a 30-minute incubation at 37° C. with 1 unit/μg DNA of antarctic phosphatase (NEB cat#M0289S, New England Biolabs, Inc., Ipswich, Mass.). The dephosphorylated pWB407 vector backbone was purified by agarose gel electrophoresis. Gel extraction was performed with a QIAquick Gel Extraction Kit (Qiagen, Valencia, Calif.).

The digested amplicons were ligated into the prepared pWB407 plasmids in 30 μL reactions using approximately 0.1 μg vector DNA and about 0.5 μg amplicon. T4 ligase was used to perform the ligation following the manufacturers recommended conditions (New England Biolabs, Inc., Beverly, Mass.). Ligation products were electroporated into *E. coli* strain WB441 (Barnes, W. *Gene* 112:29-35 (1992)). The selective indicator plates used were LB plates containing 50 μg/ml ampicilin and 80 μg/ml Xgal. Before plating, the bacteria were incubated in rich broth for 1 hour at 37° C. to allow expression of the ampicilin resistance. Control transformations lacking ligase treatment resulted in zero colonies. Colonies were scored for blue color after one day at 37° C., and one or two days at 25° C. The results are shown in FIGS. 10A-10B and 11.

Example 10

Enhancing the Sequence Accuracy of a DNA Amplification Reaction After Deamination Damage Generating Deaminated DNA The DNA subjected to deamination is pWB407 (Kermekchiev, et al. *Nucl Acids Res* 31: 6139-6147 (2003)). The damage is incurred using random mutagenesis with nitrous acid as described in Yan, W. et al. *J Virol.* 77(4):2640-50 (2003). Nitrous acid can deaminate guanine in DNA to xanthine, cytosine to uracil, and adenine to hypoxanthine.

Plasmid DNA (2 mg) is treated with 0.7 M NaNO$_2$ in 1M acetate buffer, pH 4.6. The reaction is terminated at various time points by addition of 4 volumes of ice-cold 1 M Tris-HCl (pH 7.9). The plasmid DNA is alcohol precipitated, dried and then resuspended in 100 μL of TE buffer.

Pretreatment Reaction to Repair Deaminated Bases

The repair enzyme mixtures used separately or in various combinations in a total volume of 50 μL are:
  (a)
  1 unit Human Aag, New England Biolabs, Inc., Ipswich, Mass.;
  2 units Endo III (NEB cat # M0268S), New England Biolabs, Inc., Ipswich, Mass.;
  2 units Endo V (NEB cat # M0305S), New England Biolabs, Inc., Ipswich, Mass.;
  2 units UDG (NEB cat # M0280S), New England Biolabs, Inc., Ipswich, Mass.;
  200 units Taq ligase;
  0.1 units *E. coli* DNA polymerase I;
  10 units *E. coli* Endo IV;
  1 mM NAD$^+$;
  100 μM dNTPs;
  1× Thermopol buffer.

(b)
2 units Endo V (NEB cat # M0305S), New England Biolabs, Inc., Ipswich, Mass.;
2 units UDG (NEB cat # M0280S), New England Biolabs, Inc., Ipswich, Mass.;
200 units Taq DNA ligase;
0.1 units *E. coli* DNA polymerase I;
10 units *E. coli* Endo IV;
1 mM NAD$^+$;
100 µM dNTPs;
1× Thermopol buffer.
(c)
2 units Endo V (NEB cat # M0305S), New England Biolabs, Inc., Ipswich, Mass.;
200 units Taq Ligase;
0.1 units *E. coli* DNA polymerase I;
10 units *E. coli* Endo IV;
1 mM NAD$^+$;
100 µM dNTPs;
1× Thermopol buffer.
(d)
1 unit Human Aag, New England Biolabs, Inc., Ipswich, Mass.;
2 units Endo III (NEB cat # M0268S), New England Biolabs, Inc., Ipswich, Mass.;
200 units Taq Ligase;
0.1 units *E. coli* DNA polymerase I;
10 units *E. coli* Endo IV;
1 mM NAD$^+$;
100 µM dNTPs;
1× Thermopol buffer.
(e)
1 unit Human Aag, New England Biolabs, Inc., Ipswich, Mass.;
2 units UDG (NEB cat # M0280S), New England Biolabs, Inc., Ipswich, Mass.;
200 units Taq ligase;
0.1 units *E. coli* DNA polymerase I;
10 units *E. coli* Endo IV;
1 mM NAD$^+$;
100 µM dNTPs;
1× Thermopol buffer.
(f)
1 unit Human Aag, New England Biolabs, Inc., Ipswich, Mass.;
2 units Endo V (NEB cat # M0305S), New England Biolabs, Inc., Ipswich, Mass.;
200 units Taq ligase;
0.1 unit *E. coli* DNA polymerase I;
10 units *E. coli* Endo IV;
1 mM NAD$^+$;
100 µM dNTPs;
1× Thermopol buffer.

The amplification reaction conditions and amplification accuracy determination are performed as described in Example 9.

Example 11

Unit Definitions

Thermophilic Ligase Unit

One unit is defined as the amount of enzyme required to give 50% ligation of 1 µg of BstE II-digested lambda DNA in a total reaction volume of 50 µl in 15 minutes at 45° C. Taq ligase is available from New England Biolabs, Inc., Ipswich, Mass.

Mesophilic Ligase Unit

One unit is defined as the amount of enzyme required to give 50% ligation of Hind III digested lambda DNA (5' DNA termini concentration of 0.12 µM, 300 µg/ml) in a total reaction volume of 20 µl in 30 minutes at 16° C. *E. coli* ligase is available from New England Biolabs, Inc., Ipswich, Mass.

AP Endonuclease Unit

One unit is defined as the amount of enzyme required to cleave 1 pmol of a 34-mer oligonucleotide duplex containing a single AP site in a total reaction volume of 10 µl in 1 hour at 37° C.

Mesophilic Polymerase Unit

One unit is defined as the amount of enzyme that will incorporate 10 nmol of dNTP into acid-insoluble material in a total reaction volume of 50 µl in 30 minutes at 37° C. with 33 µM dNTPs including [$^3$H]-dTTP and 70 µg/ml denatured herring sperm DNA.

Thermophilic Polymerase Unit

One unit is defined as the amount of enzyme that will incorporate 10 nmol of dNTP into acid-insoluble material in a total reaction volume of 50 µl in 30 minutes at 75° C. with 200 µM dNTPs including [3H]-dTTP and 200 µg/ml activated Calf Thymus DNA. Thermophilic polymerases-Taq polymerase and archaeal polymerases are available from New England Biolabs, Inc., Ipswich, Mass.

The unit definitions for thermophilic UDG, Fpg, Endo III and Endo VIII are the same as those for the mesophilic equivalents listed (NEB catalog, New England Biolabs, Inc., Ipswich, Mass.).

| Gene Name | Activity | Accession Number |
|---|---|---|
| UNG | Uracil-DNA glycosylase | NM_080911 |
| SMUG1 | Uracil-DNA glycosylase | NM_014311 |
| MBD4 | Removes U or T opposite G at CpG sequences | NM_003925 |
| TDG | Removes U, T or ethenoC opposite G | NM_003211 |
| OGG1 | Removes 8-oxoG opposite C | NM_016821 |
| MUTYH (MYH) | Removes A opposite 8-oxoG | NM_012222 |
| NTHL1 (NTH1) | Removes Ring-saturated or fragmented pyrimidines | NM_002528 |
| MPG | Removes 3-meA, ethenoA, hypoxanthine | NM_002434 |
| NEIL1 | Removes thymine glycol | NM_024608 |
| NEIL2 | Removes oxidative products of pyrimidines | NM_145043 |
| XPC | Binds damaged DNA as complex | NM_004628 |
| RAD23B (HR23B) | XPC, RAD23B, CETN2 | NM_002874 |
| CETN2 | | NM_004344 |
| RAD23A (HR23A) | Substitutes for HR23B | NM_005053 |
| XPA | Binds damaged DNA in preincision complex | NM_000380 |
| RPA1 | Binds DNA in preincision complex | NM_002945 |
| RPA2 | RPA1, RPA2, RPA3 | NM_002946 |
| RPA3 | | NM_002947 |
| ERCC5 (XPG) | 3' incision | NM_000123 |
| ERCC1 | 5' incision subunit | NM_001983 |
| ERCC4 (XPF) | 5' incision subunit | NM_005236 |
| LIG1 | DNA joining | NM_000234 |
| CKN1 (CSA) | Cockayne syndrome; Needed for transcription-coupled NER | NM_000082 |
| ERCC6 (CSB) | CKN1, ERCC6, XAB2 | NM_000124 |

-continued

| Gene Name | Activity | Accession Number |
|---|---|---|
| XAB2 (HCNP) | | NM_020196 |
| DDB1 | Complex defective in XP group E | NM_001923 |
| DDB2 | DDB1, DDB2 | NM_000107 |
| MMS19L (MMS19) | Transcription and NER | NM_022362 |
| FEN1 (DNase IV) | Flap endonuclease | NM_004111 |
| SPO11 | endonuclease | NM_012444 |
| FLJ35220 (ENDOV) | incision 3' of hypoxanthine and uracil | NM_173627 |
| FANCA | Involved in tolerance or repair of DNA crosslinks | NM_000135 |
| FANCB | FANCA, FANCB, FANCC, | NM_152633 |
| FANCC | FANCD2, FANCE, | NM_000136 |
| FANCD2 | FANCF, FANCG, FANCL | NM_033084 |
| FANCE | | NM_021922 |
| FANCF | | NM_022725 |
| FANCG (XRCC9) | | NM_004629 |
| FANCL | | NM_018062 |
| DCLRE1A (SNM1) | DNA crosslink repair | NM_014881 |
| DCLRE1B (SNM1B) | Related to SNM1 | NM_022836 |
| NEIL3 | Resembles NEIL1 and NEIL2 | NM_018248 |
| ATRIP (TREX1) | ATR-interacting protein 5' alternative ORF of the TREX1/ATRIP gene | NM_130384 |
| NTH | Removes damaged pyrimidines | NP_416150.1 |
| NEI | Removes damaged pyrimidines | NP_415242.1 |
| NFI | Deoxyinosine 3' endonuclease | NP_418426.1 |
| MUTM | Formamidopyrimidine DNA glycosylase | NP_418092.1 |
| UNG | Uracil-DNA glycosylase | NP_417075.1 |
| UVRA | DNA excision repair enzyme complex | NP_418482.1 |
| UVRB | | NP_415300.1 |
| UVRC | UVRA, UVRB, UVRC | NP_416423.3 |
| DENV | Pyrimidine dimer glycosylase | NP_049733.1 |

Example 12

Repair of DNA Prior to Use in DNA Sequencing Reactions to Increase the Sensitivity of the Sequencing reactions The sensitivity of the sequencing reaction is intended to mean that the amount of template DNA having a correct sequence prior to sequencing results in reduced background noise and increased signal. This makes possible longer and/or more complete sequence reads. The improved fidelity of the sequence read is an additional benefit. The beneficial use of a repair mix such as described below can be observed for sequencing methods in general. For example, sequencing methods include 454 sequencing, single molecule sequencing, Sanger sequencing and Maxam-Gilbert sequencing.

Two DNA samples are subjected to DNA sequencing before and after DNA repair. The two DNA samples are UV treated for 40 seconds (see Example 6) and lambda DNA is exposed to light in the presence of 25 μg/mL methylene blue.

Prior to use in the DNA sequencing reaction the DNA to be sequenced is contacted with one or more repair enzymes under conditions that permit activity of the repair enzymes. For example, 0.5 μg template DNA for sequencing is mixed with NEB Thermopol buffer to 1× concentration (New England Biolabs, Inc., Ipswich, Mass.) (1× concentration of Thermopol buffer contains 20 mM Tris-HCl, pH 8.8 at 25° C., 10 mM KCl, 10 mM $(NH_4)_2SO_4$, 2 mM $MgSO_4$, 0.1% Triton X-100) and incubated for 15 minutes at room temperature with a DNA repair mixture (200 units Taq DNA ligase, 0.1 units *E. coli* PolI, 1 unit T4 pdg, 15 units Endo IV, 2.5 units Endo VIII, 0.1 unit Fpg, and optionally 0.5 unit *E. coli* UDG). The repaired DNA is either used immediately for sequencing or is purified and concentrated using a commercial kit (a Qiagen, Inc., Valencia, Calif. kit, for example) prior to DNA sequencing. The sequencing reaction may be performed by the classical Sanger sequencing reactions or by methods described in U.S. Publication No. 2005/0100932, U.S. Pat. No. 6,897,023, or Margulies, et al. *Nature* 437(7057):376-80 (2005).

The sensitivity of the sequencing reaction and fidelity of the results are improved as a result of the pre-incubation with the repair mixture.

Example 13

A Multi-Enzyme Repair Mix for Repairing Damaged DNA is Effective at a Single Temperature Lambda DNA was treated by 30 s irradiation with UV (see Example 6). L72-5R (SEQ ID NO:1) and L30350F (SEQ ID NO:2) primers were selected for amplifying a 5 kilobase amplicon from the UV-treated lambda DNA either with or without prior repair. The DNA repair mix contained 200 units/μL Taq DNA ligase, 0.1 units/μL *E. coli* PolI, 1 unit/μL T4 pdg, 15 units/μL Endo IV, 0.5 unit/μL *E. coli* UDG, 2.5 units/μL Endo VIII, and 0.1 unit/μL Fpg stored in 20 mM Tris-HCl, pH 7.5 at 25° C., 100 mM NaCl, and 50% glycerol. Fifty ng of the 30 s UV-treated lambda DNA was added to thermocycler tubes each containing, 1× Thermopol buffer, 100 μM dNTPs, and 0.5 mM $NAD^+$. 1 μL of the repair enzyme mix was added to 4 out of the 8 tubes and all were brought to a final volume of 47 μL with $H_2O$. Two tubes containing repair enzymes and 2 tubes lacking the enzymes were incubated at room temperature for 15 minutes. The remaining solutions were incubated overnight at 4° C. After the indicated incubation times, the primers (1 μM), dNTPs (100 μM), and 2.5 units Taq DNA polymerase were added to each thermocycler tube and the solutions placed into a MyCycler thermocycler running the program (Bio-Rad, Hercules, Calif.): 95° C. for 2 min, one cycle; 95° C. for 10 sec, 60° C. for 30 sec and 72° C. for 5 min, 25 cycles; 72° C. for 5 min, one cycle; and a 4° C. hold. 25 μL of each reaction was analyzed on a 1% agarose gel.

In contrast to the findings of others (U.S. Publication No. 2006/0014154), which required the use of multiple different temperatures to achieve repair, incubation of UV-damaged DNA with the above repair mixture at room temperature for 15 minutes or 4° C. overnight produced an amplification product of the correct size (FIGS. 13A and 13B).

Example 14

Repair of Plasmid DNA Containing Multiple Uracils and Amplification Using Vent® DNA Polymerase Plasmid pNEB0.92U was purified from *E. coli* CJ236 (NEB# E4141S, New England Biolabs, Inc., Ipswich, Mass.). The sequence is shown in FIG. 18. Because *E. coli* CJ236 lacks dUTPase and uracil-N-glycosylase, this plasmid contains uracils randomly distributed throughout its sequence. The archaeal polymerase Vent® DNA polymerase is inhibited by uracil containing templates. Amplification of a 920 base amplicon from pNEB0.92U DNA was examined using primers S1224S (CGCCAGGGTTTTCCCAGTCACGAC) (SEQ ID NO:12 and S1233S (AGCGGATAACAATTTCACACAGGA) (SEQ ID NO: 13) either with or without prior repair. The DNA repair mix contained 200 units/µL Taq DNA ligase, 0.1 units/µL E. coli PolI, 1 unit/µL T4 pdg, 15 units/µL Endo IV, 0.5 unit/µL E. coli UDG, 2.5 units/µL Endo VIII, and 0.1 unit/µL Fpg and stored in 20 mM Tris-HCl, pH 7.5 at 25° C., 100 mM NaCl, and 50% glycerol. One µL of the repair enzyme mix was added to 2 of 4 thermocycler tubes each containing 0.5 ng pNEB0.92U, 1×Thermopol buffer, 100 µM dNTPs, and 0.5 mM $NAD^+$. All were brought to a final volume of 45 µL with $H_2O$. The reaction solutions were incubated at room temperature for 15 minutes after which the primers (final concentration: 0.4 µM), dNTPs (final concentration: 100 µM), and 1 unit Vent® DNA polymerase were added to each tube. The solutions were placed into a MyCycler thermocycler running the program: 95° C. for 2 min, one cycle; 95° C. for 10 sec, 65° C. for 30 sec and 72° C. for 1 min, 25 cycles; 72° C. for 5 min, one cycle; then a 4° C. hold. 25 µL of each reaction was examined by electrophoresis on a 1% agarose gel.

Amplification from pNEB0.92U without removal of uracils using Vent® DNA polymerase produced a barely detectable product of the desired size. Treatment of the pNEB0.92U with the repair mix significantly increased the amount of amplicon produced from this plasmid using Vent® DNA polymerase (FIG. 14).

Example 15

Enhanced Amplicon Yield from DNA Fragments

The template in this reaction was a set of 20 overlapping synthetic single strand oligonucleotides with an average size of approximately 45 nucleotides. The oligonucleotide sequences are shown below:

NEB oligo No. 316-219 (New England Biolabs, Inc., Ipswich, Mass.):

(SEQ ID NO: 14)
GGCGGCCTCGAGGCGAAACGCCGCAACTGCTTTCCGGGCGATACC

NEB oligo No. 316-220 (New England Biolabs, Inc., Ipswich, Mass.):

(SEQ ID NO: 15)
CGGCACGCCATCAATCTGCACCAGAATGCGGGTATCGCCCGGAAA

NEB oligo No. 316-221 (New England Biolabs, Inc., Ipswich, Mass.):

(SEQ ID NO: 16)
ATTGATGGCGTGCCGCAGAAAATTACCCTGCGCGAACTGTATGAA

NEB oligo No. 316-222 (New England Biolabs, Inc., Ipswich, Mass.):

(SEQ ID NO: 17)
CATGTTTTCATAGCGTTCATCTTCAAACAGTTCATACAGTTCGCG

NEB oligo No. 316-223 (New England Biolabs, Inc., Ipswich, Mass.):

(SEQ ID NO: 18)
CGCTATGAAAACATGGTGTATGTGCGCAAAAAACCGAAACGCGAA

NEB oligo No. 316-224 (New England Biolabs, Inc., Ipswich, Mass.):

(SEQ ID NO: 19)
GGTTTCCAGGTCAATGCTATACACTTTAATTTCGCGTTTCGGTTT

NEB oligo No. 316-227 (New England Biolabs, Inc., Ipswich, Mass.):

(SEQ ID NO: 20)
ATTGACCTGGAAACCGGCAAAGTGGTGCTGACCGATATTGAAGAT

NEB oligo No. 316-228 (New England Biolabs, Inc., Ipswich, Mass.):

(SEQ ID NO: 21)
CAGATGATCGGTCGCCGGCGCTTTAATCACATCTTCAATATCGGT

NEB oligo No. 316-229 (New England Biolabs, Inc., Ipswich, Mass.):

(SEQ ID NO: 22)
GCGACCGATCATCTGATTCGCTTTGAACTGGAAGATGGCCGCAGC

NEB oligo No. 316-230 (New England Biolabs, Inc., Ipswich, Mass.):

(SEQ ID NO: 23)
CAGCACCGGATGATCCACGGTGGTTTCAAAGCTGCGGCCATCTTC

NEB oligo No. 316-233 (New England Biolabs, Inc., Ipswich, Mass.):

(SEQ ID NO: 24)
GATCATCCGGTGCTGGTGTATGAAAACGGCCGCTTTATTGAAAAA

NEB oligo No. 316-234 (New England Biolabs, Inc., Ipswich, Mass.):

(SEQ ID NO: 25)
TTTATCGCCTTCTTTCACTTCAAACGCGCGTTTTTCAATAAAGCG

NEB oligo No. 316-237 (New England Biolabs, Inc., Ipswich, Mass.):

(SEQ ID NO: 26)
AAAGAAGGCGATAAAGTGCTGGTGAGCGAACTGGAACTGGTGGAA

NEB oligo No. 316-238 (New England Biolabs, Inc., Ipswich, Mass.):

(SEQ ID NO: 27)
TTTCGGGTTATCCTGGCTGCTGCTGCTCTGTTCCACCAGTTCCAG

NEB oligo No. 316-239 (New England Biolabs, Inc., Ipswich, Mass.):

(SEQ ID NO: 28)
CAGGATAACCCGAAAAACGAAAACCTGGGCAGCCCGGAACATGAT

NEB oligo No. 316-240 (New England Biolabs, Inc., Ipswich, Mass.):

(SEQ ID NO: 29)
ATATTTAATGTTTTTAATTTCCAGCAGCTGATCATGTTCCGGGCT

NEB oligo No. 316-247 (New England Biolabs, Inc., Ipswich, Mass.):

(SEQ ID NO: 30)
AAAAACATTAAATATGTGCGCGCGAACGATGATTTTGTGTTTAGCCTG

NEB oligo No. 316-248 (New England Biolabs, Inc., Ipswich, Mass.):

(SEQ ID NO: 31)
TTAATAATCACGTTATGATATTTTTTCGCGTTCAGGCTAAACACAAA

NEB oligo No. 316-265 (New England Biolabs, Inc., Ipswich, Mass.):

(SEQ ID NO: 32)
TAACGTGATTATTAACGAAAACATTGTGACCCATGCGTGCGATG

NEB oligo No. 316-266(New England Biolabs, Inc., Ipswich, Mass.):

(SEQ ID NO: 33)
GCCGCCCTGCAGACCGGTCAGATCTTCATCGCCATCGCACGCATGGG

The assembly reaction consisted of two parts: an assembly step and an amplification step. For the assembly step the standard reaction was 50 μL and contained 70 nM of each oligo, 100 μM dNTP, 0.5 mM NAD$^+$, 10 mM Tris-HCl, pH 7.5 at 25° C., 2 mM MgCl$_2$, and 50 mM NaCl. No enzymes were added to the control reaction. The first experimental reaction also contained 400 units Taq DNA ligase, 0.1 units E. coli PolI, 5 units T4 pdg, and 20 units Endo IV. The second set of reactions contained enzymes used in the first reaction and lambda beta protein (Kmiec, et al. *J. Biol. Chem.* 256:12636-12639 (1981); Rybalchenko, N., et al, *Proc. Natl. Acad. Sci. USA* 101:17056-17060 (2004)) added at a 1:1 beta protein: nucleotide mole ratio. The third reaction set contained 400 units Taq DNA ligase, 0.1 units E. coli PolI, 5 units T4 pdg, 20 units Endo IV, 0.3 mM ATP, and a 3:1 nucleotide to RecA mole ratio. The RecA was from E. coli (NEB catalog #M0249L, New England Biolabs, Inc., Ipswich, Mass.). The fourth reaction contained 400 units Taq DNA ligase, 0.1 units E. coli PolI, 5 units T4 pdg, 20 units Endo IV, 0.3 mM ATP, a 3:1 nucleotide to RecA mole ratio, and a 1:1 beta protein: nucleotide mole ratio. Glycerol content in each reaction was controlled for. The reaction mixtures were incubated for 30 minutes at room temperature.

After room temperature incubation, 5 μL of the assembly reaction was amplified using 200 μM dNTPs, 500 nM in oligonucleotides 316-219 and 316-266, 6 mM in MgSO$_4$, 1 unit of Vent® DNA Polymerase, and 1× Thermopol buffer final volume of 100 μL. The reactions were mixed and placed in a MyCycler (Bio-Rad, Hercules, Calif.) and the following thermal cycler touchdown program was used: 94° C. for 2 minutes (1 cycle); 94° C. for 30 seconds, 72° C.-62° C. (decreasing 1° C. per cycle) for 30 seconds, 72° C. for 45 seconds (10 cycles); 94° C. for 30 seconds, 62° C. for 30 seconds, 72° C. for 45 seconds (20 cycles); 72° C. for 5 minutes (1 cycle), and a 4° C. hold. Each reaction was performed in duplicate. 11 μL of 10× sample buffer was added to each sample and 25 μL was loaded onto a 1% agarose gel for electrophoresis.

The results are shown in FIG. 15. When the assembly reaction contained no added repair proteins, no amplification product was detected after the amplification step. However, when repair proteins were added in the assembly reactions, the correct 620 bp amplicon was obtained from the amplification step. Inclusion of lambda beta protein and/or E. coli RecA further increased the yield of amplicon. It was concluded that in a system in which a DNA template is composed of fragments, the inclusion of DNA repair proteins facilitates the ability to produce an amplicon. Furthermore, this effect is enhanced when some of those DNA repair proteins are known to be involved in DNA recombination.

Example 16

Enhanced Transformation Efficiency with Damaged Plasmid DNA for *E. coli*

The plasmid pUC19 (GenBank Accession #L09137) was applied to a 1% agarose gel and electrophoresed in the presence of ethidium bromide until the plasmid had moved into the gel. The DNA in the gel was subjected to 254 nm UV light for 60 seconds. During the UV exposure a gel plug containing the pUC19 plasmid was excised. The plasmid was extracted from the gel plug using a Qiagen gel extraction kit (Qiagen, Valencia, Calif.). 30 ng of UV irradiated DNA or non-irradiated DNA in a final volume of 25 μL was treated with 50 units E. coli DNA ligase (NEB#M0205S, New England Biolabs, Inc., Ipswich, Mass.), 0.1 units E. coli PolI, 5 units T4 pdg, and 20 units Endo IV in a buffer of 1× Thermopol buffer (NEB#B90045, New England Biolabs, Inc., Ipswich, Mass.) with added NAD$^+$ (Sigma product #N-7004, Sigma-Aldrich, St. Louis, Mo.) and dNTPs (NEB#N0447S, New England Biolabs, Inc., Ipswich, Mass.) to 0.5 mM and 100 μM, respectively. The reaction was incubated 15 minutes at room temperature before using the DNA to transform E. coli DH-5 alpha (NEB#C2991H, New England Biolabs, Inc., Ipswich, Mass.). As a control, both UV irradiated and non-irradiated DNA were treated as above in the absence of added enzymes. The DH5 alpha cells were transformed with UV irradiated and non-irradiated plasmid DNA that had been treated with repair enzymes or not so treated. The transformation was performed by heat shocking the E. coli in the presence of plasmid DNA. 50 μL of E. coli and plasmid were incubated on ice for 30 minutes before a 30 second incubation at 42° C. The transformation reaction was then placed on ice for 2 minutes before plating the cells on LB agar plates containing 100 μg/mL ampicillin. LB agar plates with differing dilutions of each transformation were placed in a 37° C. incubator overnight to determine the transformation efficiency of the plasmid.

Plasmid pUC19 that had been subjected to UV irradiation and not repaired had a significantly reduced transformation efficiency when compared to undamaged pUC19 plasmid that had been treated with a repair enzyme mix (see FIG. 16).

Example 17

Simultaneous Repair and Blunting of DNA for Subsequent Ligation Required for PCR, Cloning or Immobilization DNA libraries are commonly made from the environment, tissues, or cell cultures (Brady, S. F., et al. *Applied and Envi-* ronmental Microbiology, 70(11):6865-6870 (2004); Current Protocols in Molecular Biology, Vol. 1, Ausubel, F., et al (editors), John Wiley & Sons, Inc., Hoboken, N.J.; Chapter 5: "Construction of Recombinant DNA Libraries" (2004); Courtois, S., et al., *Applied and Environmental Microbiology,* 69(1):49-55 (2003); U.S. Pat. No. 6,444,426). These libraries are routinely created by shearing the DNA from the desired source by sonication, enzymatic treatment, or nebulization, preparing the DNA ends and ligating the mixture to oligonucleotides or plasmid DNA (Weinmann, A. S., *Molecular and Cellular Biology,* 21(20):6820-6832 (2001)). Ligation to oligonucleotides permits subsequent PCR or immobilization on arrays containing DNA sequences complimentary to the ligated oligo. Ligation to a plasmid permits the propagation in a heterologous host. A recent use of libraries is in chromatin immunoprecipitation (Guenther, M. G., et al. *Proc. Natl. Acad. Sci. USA* 102(24):8603-8608 (2005); Ren, B., et al. *Genes Dev.* 16:245-256 (2002); and Odom, D. T., et al. *Science* 303:1378-1381 (2004)). As part of preparing DNA ends for blunt end ligation, researchers often use a polymerase such as T4 DNA polymerase. However, an enzyme mix is provided here that can not only repair damage that the DNA may have acquired during purification, preparation and storage, but can also create blunt ends. This enzyme mix includes a ligase and a proof-reading polymerase and any cofactors necessary to allow enzyme activity. Preferably, the mix is composed of a ligase, a proof-reading polymerase, an apurinic/apyrimidinic endonuclease, UDG, FPG, and T4 pdg.

As an example, Chromatin IP (ChIP) is performed on HeLa cell DNA using antibodies to E2F1, E2F2, E2F3, E2F4, E2F5, or E2F6 as described previously (Weinmann, A. S. *Molecular and Cellular Biology* 21(20):6820-6832 (2001)). The cloning of ChIP enriched DNA is as described previously (Weinmann, A. S. *Molecular and Cellular Biology* 21(20): 6820-6832 (2001)); http://mcardle.oncology.wisc.edu/farnham). The use of T4 DNA polymerase alone to blunt the DNA is replaced by an enzyme mixture containing at least a combination of a ligase and a proof-reading polymerase. For example, the DNA is incubated with 400 units Taq DNA ligase, 0.1 units *E. coli* polymerase I, 20 units *E. coli* endonuclease IV, 5 units T4 PDG in 1× Thermopol buffer supplemented with 0.5 mM NAD$^+$ and 100 µM dNTPs at room temperature for 15 minutes. Prior to the ligation step the blunted and repaired DNA can be incubated at 75° C. for 20 minutes to inactivate the *E. coli* polymerase I.

The mix of a proof-reading polymerase and at least a ligase is able to blunt the DNA ends for subsequent ligation to either primers or a plasmid.

Example 18

Enhanced Amplicon Yield from Fragmented DNA. PRODUCTION of Larger DNA Pieces from Fragmented DNA for Downstream Processes such as Amplification, DNA Sequencing. Microarray Analysis, and Hybridization Analysis Fragmented DNA, from 0.1-1000 ng, is incubated with a recombination/DNA annealing proficient protein, such as *E. coli* RecA (NEB# M0249S, New England Biolabs, Inc., Ipswich, Mass.; West, S. C. *Ann. Rev. Biochem.* 61, 603-640 (1992)) and/or lambda beta protein (Rybalchenko, N., et al. *Proc. Natl. Acad. Sci. USA,* 101(49):17056-17060 (2004); Kmeic, E., & Holloman, W. K., *J. Biol. Chem.* 256(24): 12636-12639 (1981)) in a standard reaction buffer and any required cofactors in a final volume of 5-1000 µL. An example of a standard reaction buffer is 10 mM Tris-HCl, pH 7.5 at 25° C., 2 mM MgCl$_2$, and 50 mM NaCl. When using RecA, 1 mM ATP is included in the standard reaction. Either simultaneous with or subsequent to the incubation with the RecA and/or beta protein the DNA is also contacted with a repair mix composed of at least a DNA ligase activity a DNA polymerase activity and any required cofactors, i.e., ATP, NAD$^+$ and dNTPs. The repair mix contains 400 units Taq DNA ligase and 0.1 units *E. coli* PolI and, in addition, 5 units T4 pdg, 20 units Endo IV, 0.5 units *E. coli* UDG, 2.5 units/µL Endo VIII, and/or 0.1 unit Fpg are added. Prior to incubation with the repair proteins the DNA fragments may be heat-denatured and the temperature reduced to less than 39° C. For example, the DNA in reaction buffer may be heated to 98° C. for 5 minutes then cooled down to less than 39° C. A standard reaction volume is 5 to 1000 µL and the incubation time is 1 to 60 minutes at 4-37° C. Typically, the RecA or beta protein is used at a 0.5:1 to 5:1 nucleotide to protein mole ratio.

Modifications to the above method include substituting RecA and/or beta protein with thermostable equivalents. Some examples of these proteins are ttRecA (Kato R, & Kuramitsu S., *Eur J Biochem.* 259(3):592-601 (1999)), Taq RecA, Tma RecA, and Apy RecA (Wetmur, J. G., et al. *J Biol Chem.* 269(41):25928-35 (1994)). The use of thermostable proteins means that thermostable RecA or beta-like protein can be mixed with the DNA during the denaturation step. Any co-factors required for the protein activity are also included. In addition, repair enzymes as described above are added prior to or after denaturation. Note that for thermostable recombination proteins (RecA or beta-like protein) the proteins can be added to the reaction mixture for 1-60 minutes at 45-75° C. to permit the optimal activity before the addition of non-thermostable repair proteins at temperatures of less than 39° C.

The repaired DNA can then be used in a subsequent process, for example PCR. For example, as a test system human genomic DNA is fragmented using sonication and size fractionated to give average fragment sizes clustered around 200 bp. 500 ng of the size-fractionated material is treated as described above. A titration of 5-100 ng of this repaired material is used in PCR reactions using primers that reliably generate 1, 2, and 4 kb amplicons from undamaged human genomic DNA. Examples of a primer set are

```
DNMT-R:
GGGGCACCTTCTCCAACTCATACT,    (SEQ ID NO: 34)

DNMT-1Fb:
cctcatttggggaggggttatct,     (SEQ ID NO: 35)

DNMT-2Fc:
cctgaaacaaggttgtggcatagc,    (SEQ ID NO: 36)
and

DNMT-4Fb:
gagtgagttgaaagtgctccataca.   (SEQ ID NO: 37)
```

The same template titration is performed with the fragmented DNA. When the non-repaired and repaired DNA are compared, the repaired templates permit a visible amplicon on an agarose gel, visualized with UV light and ethidium bromide, to be generated with at least two fold lower amounts of template DNA.

The use of RecA and/or beta protein-like activities in conjunction with at least ligase and polymerase activities results in the detection of PCR amplicons at lower template amounts as compared to unrepaired DNA.

Example 19

Amplification of DNA from Stored Ancient Cave Bear Tissue Samples After Repair of DNA Damage In contrast to modern material, the DNA extracted from ancient bones shows a variety of types of damage. The most common type of damage is fragmentation caused by single stand breaks, which lead to a reduced average molecule length of the extracted DNA, as well as non-enzymatic attacks such as irradiation and reactive oxygen species. (See: Hoss, et al. *Nucleic Acids Res.* 24(7):1304-7 (1996)). Repairing ancient DNA (aDNA) damage is important to improve the utility of the extracted DNA.

An ancient DNA was extracted as described in Pääbo *Proc Natl Acad Sci USA* 86(6):1939-43 (1989). Amplification of a 330 bp cave bear DNA (~44,000 years old) was performed using primers CB F1 (CTATTTAAACTATTCCCTGGTACATAC) (SEQ ID NO:38) and CB R1 (GGAGCGAGAGGTACACGT) (SEQ ID NO:39) either with or without prior repair. The DNA repair mix was composed of 200 units/μL Taq DNA ligase, 0.1 units/μL *E. coli* PolI, 1 unit/μL T4 pdg, 15 units/μL Endo IV, 0.5 unit/μL *E. coli* UDG, 2.5 units/μL Endo VIII, and 0.1 unit/μL Fpg and stored in 20 mM Tris-HCl, pH 7.5 at 25° C., 100 mM NaCl, and 50% gycerol. To 2 of 4 thermocycler tubes each containing 2 μl aDNA, 1× Phusion™ polymerase buffer, 100 μM dNTPs, and 0.5 mM NAD+ was added 1 μL of the repair enzyme mix. All were brought to a final volume of 45 μL with H$_2$O. The reaction solutions were incubated at room temperature for 15 minutes after which the primers (to 0.4 μM), dNTPs (to 100 μM), and 1 unit Phusion™ DNA polymerase were added to each. The solutions were placed into a MyCycler thermocycler (Bio-Rad, Hercules, Calif.) running the program: 98° C. for 30 s, one cycle; 98° C. for 10 sec, 58° C. for 20 s and 72° C. for 20 s, 30 cycles; 72° C. for 5 min, one cycle; then a 4° C. hold. The repaired PCR amplified DNA and control PCR amplified DNA (no repair) was used immediately in a second PCR amplification using nested primers. The amplification reaction with the nested primers used 1× Taq Master Mix (Catalog # M0270S, New England Biolabs, Inc., Ipswich, Mass.), 2 μL of the previous amplification, and primers CB F1 (CTATTTAAACTATTCCCTGGTACATAC) (SEQ ID NO:40) and CB F3 (GCCCCATGCATATAAGCATG) (SEQ ID NO:41) at a final concentration of 0.2 μM. The total reaction volume was 50 μL. The reaction was analyzed by applying 5 μl of each reaction to a 1% agarose gel, prepared, electrophoresed and visualized as described above.

The amount of mitochondrial DNA in the cave bear bone samples was estimated with the TaqMan® assay (Applied Biosystems, Foster City, Calif.) using primers 5'-AAAATGCCCTTTGGATCTTAM-3' (SEQ ID NO:43) and 5'-ACTGCTGTATCCCGTGGG-3' (SEQ ID NO:44).

The amplified DNA is either used immediately in the DNA sequencing methodology or subjected to DNA purification and concentration. After purification the DNA is subjected to DNA sequencing (see Example 12).

Amplification from cave bear DNA using Phusion DNA polymerase and Taq polymerase in nested PCR produced a detectable product of the desired amplicon size in one sample (CB3A). Treatment with the repair mix produced another amplicon from sample CB3B. Sequence analysis of amplicons from treated and untreated cave bear DNAs (CB3B sample) will reveal whether treatment with the repair mix significantly helped to remove PCR amplification errors associated with DNA modifications described in Hoss, et al. *Nucleic Acids Res.* 24(7):1304-7 (1996).

Treatment of the cave bear DNA template with the repair enzyme mix permitted Phusion™ DNA polymerase to more effectively produce the desired amplicon and to remove PCR amplification errors (FIG. 17).

The invention claimed is:

1. A composition, comprising:
a reaction mixture comprising an $NAD^+$-dependent ligase, an $NAD^+$ cofactor, a polymerase having flap endonuclease activity and an AP endonuclease, the reaction mixture not including Endo VI.

2. A composition according to claim 1, wherein the AP endonuclease is at a concentration of 1-100 units, the polymerase at a concentration of 0.05-5 units, and the ligase at a concentration of 5-500 units in a volume 10-1000 μl of the reaction mixture.

3. A composition according to claim 1, further comprising a glycosylase/lyase, wherein the glycosylase/lyase is selected from the group consisting of *E. coli* Endo III, *E. coli* Endo VIII, *E. coli* fpg, human OGGI and T4 pyrimidine dimer glycosylase (T4pdg).

4. A composition according to claim 1, wherein the AP endonuclease is a Type II AP Endonuclease.

5. A composition according to claim 1, wherein the AP endonuclease is selected from the group consisting of *E. coli* Endo IV, Tth Endo IV, and human AP endonuclease.

6. A composition according to claim 1, wherein the glycosylase/lyase is T4 pyrimidine dimer glycosylase (pdg).

7. A composition according to claim 6, wherein the glycosylase/lyase is [FAPY]-DNA glycosylase (Fpg).

8. A composition according to claim 1, further comprising at least one of UvrA, UvrB, UvrC, UvrD and Cho.

9. A composition according to claim 1, further comprising a glycosylase/lyase, wherein the glycosylase/lyase is selected from the group consisting of at least one of Endo VIII, *E. coli* fpg, human OGGI, T4Pdg and Endo III.

10. A composition according to claim 1, further comprising a glycosylase wherein the glycosylase is selected from at least one of UDG, *E. coli* AlkA and Aag.

11. A method for sequencing a polynucleotide, comprising:
(a) contacting the polynucleotide with the composition of claim 1; and
(b) sequencing the polynucleotide.

12. A composition according to claim 1, wherein the polymerase is Bst polymerase, the AP endonuclease is Endo IV, the ligase is Taq ligase, the glycosylase is *E. coli* UDG, the glycosylase/lyase is *E. coli* Fpg, T4 pdg and *E. coli* Endo VIII.

13. A composition according to claim 1, wherein the polymerase is an *E. coli* Y family polymerase.

14. A composition according to claim 1, wherein the $NAD^+$-dependent ligase, and the polymerase are purified enzymes.

15. A composition according to claim 1, further comprising an effective amount of each of the $NAD^+$-dependent ligase, an $NAD^+$ cofactor, the polymerase having flap endonuclease activity and the AP endonuclease, wherein the reaction mixture when added to a damaged polynucleotide prior to amplification enhances at least one of yield and fidelity of an amplified polynucleotide compared with the yield or fidelity of the amplified polynucleotide without prior addition of the reaction mixture.

* * * * *

SEQUENCE LISTING

```
<160> NUMBER OF SEQ ID NOS: 44

<210> SEQ ID NO 1
<211> LENGTH: 23
<212> TYPE: DNA
<213> ORGANISM: artificial
<220> FEATURE:
<223> OTHER INFORMATION: primer

<400> SEQUENCE: 1
cgaacgtcgc gcagagaaac agg                                           23

<210> SEQ ID NO 2
<211> LENGTH: 20
<212> TYPE: DNA
<213> ORGANISM: artificial
<220> FEATURE:
<223> OTHER INFORMATION: primer

<400> SEQUENCE: 2
cctgctctgc cgcttcacgc                                               20

<210> SEQ ID NO 3
<211> LENGTH: 25
<212> TYPE: DNA
<213> ORGANISM: artificial
<220> FEATURE:
<223> OTHER INFORMATION: primer
```

<400> SEQUENCE: 3
tttttagcaa tacactacac agcaa                                          25

<210> SEQ ID NO 4
<211> LENGTH: 19
<212> TYPE: DNA
<213> ORGANISM: artificial
<220> FEATURE:
<223> OTHER INFORMATION: primer

<400> SEQUENCE: 4
attacgccaa tcgatcacg                                                 19

<210> SEQ ID NO 5
<211> LENGTH: 27
<212> TYPE: DNA
<213> ORGANISM: artificial
<220> FEATURE:
<223> OTHER INFORMATION: primer

<400> SEQUENCE: 5
gcacagaagc tattatgcgt ccccagg                                        27

<210> SEQ ID NO 6
<211> LENGTH: 25
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (6)..(6)
<223> OTHER INFORMATION: 8-oxo-Guanine
<220> FEATURE:
<221> NAME/KEY: misc_feature
<222> LOCATION: (18)..(18)
<223> OTHER INFORMATION: m=c or a

<400> SEQUENCE: 6 gggggggagag tttgatcmtg gctca                                         25

<210> SEQ ID NO 7
<211> LENGTH: 28
<212> TYPE: DNA
<213> ORGANISM: artificial
<220> FEATURE:
<223> OTHER INFORMATION: primer
<220> FEATURE:
<221> NAME/KEY: misc_feature
<222> LOCATION: (6)..(6)
<223> OTHER INFORMATION: 8-oxo-Guanine
<220> FEATURE:
<221> NAME/KEY: misc_feature
<222> LOCATION: (12)..(12)
<223> OTHER INFORMATION: y=c or t

<400> SEQUENCE: 7 gggggggtacg gytaccttgt tacgactt                                      28

<210> SEQ ID NO 8
<211> LENGTH: 24
<212> TYPE: DNA
<213> ORGANISM: artificial
<220> FEATURE:
<223> OTHER INFORMATION: primer

<400> SEQUENCE: 8
ccatgattca gtgtgcccgt ctgg                                           24

<210> SEQ ID NO 9
<211> LENGTH: 29
<212> TYPE: DNA
<213> ORGANISM: artificial
<220> FEATURE:
<223> OTHER INFORMATION: primer

<400> SEQUENCE: 9
tgtcgatcag gatgatctgg acgaagagc                                         29

<210> SEQ ID NO 10
<211> LENGTH: 33
<212> TYPE: DNA
<213> ORGANISM: artificial
<220> FEATURE:
<223> OTHER INFORMATION: primer

<400> SEQUENCE: 10
cgaaagcttt caaggatctt accgctgttg aga                                    33

<210> SEQ ID NO 11
<211> LENGTH: 813
<212> TYPE: DNA
<213> ORGANISM: unknown
<220> FEATURE:
<223> OTHER INFORMATION: Thermus thermophilus endonuclease IV

<400> SEQUENCE: 11
atgccgcgct acgggttcca cctttccatc gccgggaaaa agggcgtggc cggggcggtg        60
gaggaggcca ccgccctcgg cctcaccgct ttccagatct cgccaaaag cccgcggagc        120 tggcgcccaa gggccctctc cccggccgag gtggaggcct ccgcgccttt aaggaggcc        180 tccgggggcc tccccgccgt gatccacgcc tcctacctgg tcaacctggg ggcggagggg       240
gagctttggg agaagagcgt ggcgagcctg cggacgacc tggagaaggc cgccctcctc        300
ggggtggagt acgtggtcgt ccaccccggc tcggccgcc ccgagcgggt caaggaaggg        360
gccctcaagg ccctgcgcct cgccggcgtc cgctcccgcc ccgtcctcct cgtggagaac       420
accgccgggg gcggggagaa ggtgggggcg cggtttgagg agctcgcctg gctcgtggcg       480
gacacccccc tccaggtctg cctggacacc tgccacgcct acgccgccgg gtacgacgtg       540
gccgaggacc ccttgggggt cctggacgcc ctggaccggg ccgtgggcct ggagcgggtg       600
cccgtggtcc acctcaacga ctccgtgggc ggcctcggaa gccgcgtgga ccaccacgcc       660
cacctcctcc agggaaagat cggggagggg ctcaagcgcg tcttcttgga cccgaggctc       720
aaggaccggg tcttcatcct ggaaacccccc aggggaccgg aggaggacgc ctggaacctc     780
cgggtcctca gggcctggct cgaggaggcc taa                                    813

<210> SEQ ID NO 12
<211> LENGTH: 24
<212> TYPE: DNA
<213> ORGANISM: artificial
<220> FEATURE:
<223> OTHER INFORMATION: primer

<400> SEQUENCE: 12
cgccagggtt ttcccagtca cgac                                              24

<210> SEQ ID NO 13
<211> LENGTH: 24
<212> TYPE: DNA
<213> ORGANISM: artificial

```
<220> FEATURE:
<223> OTHER INFORMATION: primer

<400> SEQUENCE: 13
agcggataac aatttcacac agga                                      24

<210> SEQ ID NO 14
<211> LENGTH: 45
<212> TYPE: DNA
<213> ORGANISM: unknown
<220> FEATURE:
<223> OTHER INFORMATION: synthetic oligo

<400> SEQUENCE: 14
ggcggcctcg aggcgaaacg ccgcaactgc tttccgggcg atacc                45

<210> SEQ ID NO 15
<211> LENGTH: 45
<212> TYPE: DNA
<213> ORGANISM: unknown
<220> FEATURE:
<223> OTHER INFORMATION: synthetic oligo

<400> SEQUENCE: 15
cggcacgcca tcaatctgca ccagaatgcg ggtatcgccc ggaaa                45

<210> SEQ ID NO 16
<211> LENGTH: 45
<212> TYPE: DNA
<213> ORGANISM: unknown
<220> FEATURE:
<223> OTHER INFORMATION: synthetic oligo

<400> SEQUENCE: 16
attgatggcg tgccgcagaa aattaccctg cgcgaactgt atgaa                45

<210> SEQ ID NO 17
<211> LENGTH: 45
<212> TYPE: DNA
<213> ORGANISM: unknown
<220> FEATURE:
<223> OTHER INFORMATION: synthetic oligo

<400> SEQUENCE: 17
catgttttca tagcgttcat cttcaaacag ttcatacagt tcgcg                45

<210> SEQ ID NO 18
<211> LENGTH: 45
<212> TYPE: DNA
<213> ORGANISM: unknown
<220> FEATURE:
<223> OTHER INFORMATION: synthetic oligo

<400> SEQUENCE: 18
cgctatgaaa acatggtgta tgtgcgcaaa aaccgaaaac gcgaa                45

<210> SEQ ID NO 19
<211> LENGTH: 45
<212> TYPE: DNA
<213> ORGANISM: unknown
<220> FEATURE:
<223> OTHER INFORMATION: synthetic oligo

<400> SEQUENCE: 19
ggtttccagg tcaatgctat acactttaat ttcgcgtttc ggttt                45
```

```
<210> SEQ ID NO 20
<211> LENGTH: 46
<212> TYPE: DNA
<213> ORGANISM: unknown
<220> FEATURE:
<223> OTHER INFORMATION: synthetic oligo

<400> SEQUENCE: 20
attgacctgg aaaccggcaa agtggtgctg accgatatta gaagat           46

<210> SEQ ID NO 21
<211> LENGTH: 45
<212> TYPE: DNA
<213> ORGANISM: unknown
<220> FEATURE:
<223> OTHER INFORMATION: synthetic oligo

<400> SEQUENCE: 21
cagatgatcg gtcgccggcg cttta atcac atcttcaata tcggt            45

<210> SEQ ID NO 22
<211> LENGTH: 45
<212> TYPE: DNA
<213> ORGANISM: unknown
<220> FEATURE:
<223> OTHER INFORMATION: synthetic oligo

<400> SEQUENCE: 22
gcgaccgatc atctgattcg ctttgaactg gaagatggcc gcagc             45

<210> SEQ ID NO 23
<211> LENGTH: 45
<212> TYPE: DNA
<213> ORGANISM: unknown
<220> FEATURE:
<223> OTHER INFORMATION: synthetic oligo

<400> SEQUENCE: 23
cagcaccgga tgatccacgg tggtttcaaa gctgcggcca tcttc             45

<210> SEQ ID NO 24
<211> LENGTH: 45
<212> TYPE: DNA
<213> ORGANISM: unknown
<220> FEATURE:
<223> OTHER INFORMATION: synthetic

<400> SEQUENCE: 24
gatcatccgg tgctggtgta tgaaaacggc cgctttattg aaaaa             45

<210> SEQ ID NO 25
<211> LENGTH: 45
<212> TYPE: DNA
<213> ORGANISM: unknown
<220> FEATURE:
<223> OTHER INFORMATION: synthetic oligo

<400> SEQUENCE: 25
tttatcgcct tctttcactt caaacgcgcg ttttt caata aagcg             45

<210> SEQ ID NO 26
<211> LENGTH: 45
<212> TYPE: DNA
<213> ORGANISM: unknown
<220> FEATURE:
<223> OTHER INFORMATION: synthetic oligo

<400> SEQUENCE: 26
```
aaagaaggcg ataaagtgct ggtgagcgaa ctggaactgg tggaa                45

<210> SEQ ID NO 27
<211> LENGTH: 45
<212> TYPE: DNA
<213> ORGANISM: unknown
<220> FEATURE:
<223> OTHER INFORMATION: synthetic oligo

<400> SEQUENCE: 27
tttcgggtta tcctggctgc tgctgctctg ttccaccagt tccag                45

<210> SEQ ID NO 28
<211> LENGTH: 45
<212> TYPE: DNA
<213> ORGANISM: unknown
<220> FEATURE:
<223> OTHER INFORMATION: synthetic oligo

<400> SEQUENCE: 28
caggataacc cgaaaaacga aaacctgggc agcccggaac atgat                45

<210> SEQ ID NO 29
<211> LENGTH: 45
<212> TYPE: DNA
<213> ORGANISM: unknown
<220> FEATURE:
<223> OTHER INFORMATION: synthetic oligo

<400> SEQUENCE: 29
atatttaatg tttttaattt ccagcagctg atcatgttcc gggct                45

<210> SEQ ID NO 30
<211> LENGTH: 48
<212> TYPE: DNA
<213> ORGANISM: unknown
<220> FEATURE:
<223> OTHER INFORMATION: synthetic oligo

<400> SEQUENCE: 30
aaaaacatta aatatgtgcg cgcgaacgat gattttgtgt ttagcctg             48

<210> SEQ ID NO 31
<211> LENGTH: 47
<212> TYPE: DNA
<213> ORGANISM: unknown
<220> FEATURE:
<223> OTHER INFORMATION: synthetic oligo

<400> SEQUENCE: 31
ttaataatca cgttatgata tttttcgcg ttcaggctaa acacaaa                47

<210> SEQ ID NO 32
<211> LENGTH: 44
<212> TYPE: DNA
<213> ORGANISM: unknown
<220> FEATURE:
<223> OTHER INFORMATION: synthetic oligo

<400> SEQUENCE: 32
taacgtgatt attaacgaaa acattgtgac ccatgcgtgc gatg                 44

<210> SEQ ID NO 33
<211> LENGTH: 47
<212> TYPE: DNA
<213> ORGANISM: unknown

```
<220> FEATURE:
<223> OTHER INFORMATION: synthetic oligo

<400> SEQUENCE: 33
gccgccctgc agaccggtca gatcttcatc gccatcgcac gcatggg                    47

<210> SEQ ID NO 34
<211> LENGTH: 24
<212> TYPE: DNA
<213> ORGANISM: artificial
<220> FEATURE:
<223> OTHER INFORMATION: primer

<400> SEQUENCE: 34
ggggcacctt ctccaactca tact                                             24

<210> SEQ ID NO 35
<211> LENGTH: 23
<212> TYPE: DNA
<213> ORGANISM: artificial
<220> FEATURE:
<223> OTHER INFORMATION: primer

<400> SEQUENCE: 35
cctcatttgg ggaggggtta tct                                              23

<210> SEQ ID NO 36
<211> LENGTH: 24
<212> TYPE: DNA
<213> ORGANISM: artificial
<220> FEATURE:
<223> OTHER INFORMATION: primer

<400> SEQUENCE: 36
cctgaaacaa ggttgtggca tagc                                             24

<210> SEQ ID NO 37
<211> LENGTH: 25
<212> TYPE: DNA
<213> ORGANISM: artificial
<220> FEATURE:
<223> OTHER INFORMATION: primer

<400> SEQUENCE: 37
gagtgagttg aaagtgctcc ataca                                            25

<210> SEQ ID NO 38
<211> LENGTH: 27
<212> TYPE: DNA
<213> ORGANISM: artificial
<220> FEATURE:
<223> OTHER INFORMATION: primer

<400> SEQUENCE: 38
ctatttaaac tattccctgg tacatac                                          27

<210> SEQ ID NO 39
<211> LENGTH: 18
<212> TYPE: DNA
<213> ORGANISM: artificial
<220> FEATURE:
<223> OTHER INFORMATION: primer

<400> SEQUENCE: 39
ggagcgagag gtacacgt                                                    18
```

-continued

```
<210> SEQ ID NO 40
<211> LENGTH: 27
<212> TYPE: DNA
<213> ORGANISM: artificial
<220> FEATURE:
<223> OTHER INFORMATION: primer

<400> SEQUENCE: 40
ctatttaaac tattccctgg tacatac                                            27

<210> SEQ ID NO 41
<211> LENGTH: 20
<212> TYPE: DNA
<213> ORGANISM: artificial
<220> FEATURE:
<223> OTHER INFORMATION: primer

<400> SEQUENCE: 41
gccccatgca tataagcatg                                                    20

<210> SEQ ID NO 42
<211> LENGTH: 3474
<212> TYPE: DNA
<213> ORGANISM: unknown
<220> FEATURE:
<223> OTHER INFORMATION: plasmid pNEB0.92U

<400> SEQUENCE: 42
gacgaaaggg cctcgtgata cgcctatttt tataggttaa tgtcatgata ataatggttt      60
cttagacgtc aggtggcact tttcggggaa atgtgcgcgg aaccccatt tgtttatttt      120 tctaaataca ttcaaatatg tatccgctca tgagacaata accctgataa atgcttcaat      180
aatattgaaa aaggaagagt atgagtattc aacatttccg tgtcgccctt attccctttt      240
ttgcggcatt ttgccttcct gttttttgctc acccagaaac gctggtgaaa gtaaaagatg      300
ctgaagatca gttgggtgca cgagtgggtt acatcgaact ggatctcaac agcggtaaga      360
tccttgagag ttttcgcccc gaagaacgtt ttccaatgat gagcactttt aaagttctgc      420
tatgtggcgc ggtattatcc cgtattgacg ccgggcaaga gcaactcggt cgccgcatac      480
actattctca gaatgacttg gttgagtact caccagtcac agaaaagcat cttacggatg      540
gcatgacagt aagagaatta tgcagtgctg ccataaccat gagtgataac actgcggcca      600
acttacttct gacaacgatc ggaggaccga aggagctaac cgcttttttg cacaacatgg      660
gggatcatgt aactcgcctt gatcgttggg aaccggagct gaatgaagcc ataccaaacg      720
acgagcgtga caccacgatg cctgtagcaa tggcaacaac gttgcgcaaa ctattaactg      780
gcgaactact tactctagct tcccggcaac aattaataga ctggatggag gcggataaag      840
ttgcaggacc acttctgcgc tcggcccttc cggctggctg gtttattgct gataaatctg      900
gagccggtga gcgtgggtct cgcggtatca ttgcagcact ggggccagat ggtaagccct      960
cccgtatcgt agttatctac acgacgggga gtcaggcaac tatggatgaa cgaaatagac      1020
agatcgctga gataggtgcc tcactgatta agcattggta actgtcagac caagtttact      1080
catatatact ttagattgat ttaaaacttc atttttaatt taaaaggatc taggtgaaga      1140
tcctttttga taatctcatg accaaaatcc cttaacgtga gttttcgttc cactgagcgt      1200 cagacccgt agaaaagatc aaaggatctt cttgagatcc ttttttctg cgcgtaatct      1260 gctgcttgca acaaaaaaa ccaccgctac cagcggtggt ttgtttgccg gatcaagagc      1320
taccaactct ttttccgaag gtaactggct tcagcagagc gcagatacca aatactgttc      1380
ttctagtgta gccgtagtta ggccaccact tcaagaactc tgtagcaccg cctacatacc      1440
```

```
tcgctctgct aatcctgtta ccagtggctg ctgccagtgg cgataagtcg tgtcttaccg    1500
ggttggactc aagacgatag ttaccggata aggcgcagcg gtcgggctga acgggggtt    1560 cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag    1800 gggggcggag cctatggaaa aacgccagca acgcggcctt tttacggttc ctggcctttt    1860
gctggccttt tgctcacatg ttctttcctg cgttatcccc tgattctgtg ataaccgta    1920 ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcaccca ggctttacac tttatgcttc    2160
cggctcgtat gttgtgtgga attgtgagcg gataacaatt tcacacagga aacagctatg    2220
accatgatta cgccaagctt cctgcagggt taaacgctg aggagacata tggccgccga    2280
gtctcagtta aaacgtgtga tcgaaacgct gcgccgtctg ggtattgaag aggtgctgaa    2340 actgaacgt cgtgatcctc agtatcgcgc tgtttgcaat gtggtcaagc gtcatgcga    2400 aactgtgggc agccgtttag ctatgttaaa cgccctgatt tcatatcgcc tgaccggtaa    2460
gggtgaggag cattgggaat atatttcggcaa atatttcagt cagttagaag tgattgatct    2520
gtgccgtgat ttcttaaaat atattgagac cagcccgttc ctgaaaatcg gtgtcgaggc    2580
gcgcaagaaa cgcgcgttaa aggcctgcga ctacgtccct aacttggaag acttgggcct    2640
gaccctgcgt caattaagcc acatcgttgg tgcacgccgt gagcagaaga cgttggtctt    2700
cacaatcaag atcctgaact atgcatatat gtgcagccgc ggtgttatcg cgtgttgccg    2760
ttcgatattc caattcctgt ggattaccgt gttgcacgct tgacctggtg cgccggtctg    2820
atcgatttcc cgccggagga ggccttgcgc cgctacgagg ctgtgcagaa aatctgggat    2880
gccgtggcgc gcgaaactgg tattcctcca ttgcacttgg acaccctgtt atggttggcc    2940
ggtcgcgcgg tgctgtatgg tgaaaaacctg catggtgtgc cgaaagaggt catcgctctg    3000
ttccaatggc gcggcggctg ccgtccgcct agcgagtaaa ccccctcagc ttaattaagg    3060
cgcgcctgag ctcgaattca ctggccgtcg ttttacaacg tcgtgactgg gaaaaccctg    3120
gcgttaccca acttaatcgc cttgcagcac atcccccttt cgccagctgg cgtaatagcg    3180
aagaggcccg caccgatcgc ccttcccaac agttgcgcag cctgaatggc gaatggcgcc    3240
tgatgcggta ttttctcctt acgcatctgt gcggtatttc acaccgcata tggtgcactc    3300
tcagtacaat ctgctctgat gccgcatagt taagccagcc ccgacacccg ccaacacccg    3360
ctgacgcgcc ctgacgggct tgtctgctcc cggcatccgc ttacagacaa gctgtgaccg    3420
tctccgggag ctgcatgtgt cagaggtttt caccgtcatc accgaaacgc gcga          3474
```

<210> SEQ ID NO 43
<211> LENGTH: 22
<212> TYPE: DNA
<213> ORGANISM: artificial
<220> FEATURE:
<223> OTHER INFORMATION: primer

<400> SEQUENCE: 43
aaaatgccct ttggatctta aa                                              22

```
<210> SEQ ID NO 44
<211> LENGTH: 18
<212> TYPE: DNA
<213> ORGANISM: artificial
<220> FEATURE:
<223> OTHER INFORMATION: primer

<400> SEQUENCE: 44
actgctgtat cccgtggg                                                    18
```